US011841468B2

(12) United States Patent
Shirley

(10) Patent No.: US 11,841,468 B2
(45) Date of Patent: Dec. 12, 2023

(54) PHOTON SENSOR

(71) Applicant: Kairos Sensors LLC, Corvallis, OR (US)

(72) Inventor: Kendon Robert Shirley, Corvallis, OR (US)

(73) Assignee: Kairos Sensors LLC, Corvallis, OR (US)

( * ) Notice: Subject to any disclaimer, the term of this patent is extended or adjusted under 35 U.S.C. 154(b) by 0 days.

(21) Appl. No.: 17/498,937

(22) Filed: Oct. 12, 2021

(65) Prior Publication Data

US 2022/0291400 A1  Sep. 15, 2022

Related U.S. Application Data

(60) Provisional application No. 63/200,484, filed on Mar. 10, 2021.

(51) Int. Cl.
| | | |
|---|---|---|
| *H01L 27/146* | (2006.01) | |
| *G01T 1/24* | (2006.01) | |
| *A61B 6/00* | (2006.01) | |
| *G01N 23/046* | (2018.01) | |

(52) U.S. Cl.
CPC ............ *G01T 1/247* (2013.01); *A61B 6/4208* (2013.01); *G01N 23/046* (2013.01); *H01L 27/14658* (2013.01)

(58) Field of Classification Search
CPC .... G01T 1/247; A61B 6/4208; G01N 23/046; H01L 27/14658; Y02E 10/549
See application file for complete search history.

(56) References Cited

U.S. PATENT DOCUMENTS

| | | | |
|---|---|---|---|
| 10,770,239 B1 | 9/2020 | Mohite et al. | |
| 11,581,359 B2 | 2/2023 | Deumel et al. | |
| 2010/0051897 A1* | 3/2010 | Chen ................. | H01L 29/78684 438/105 |
| 2013/0065022 A1* | 3/2013 | Seo ..................... | H01L 29/1606 428/167 |
| 2013/0248823 A1* | 9/2013 | Bol .................. | H01L 29/41733 257/29 |
| 2020/0225367 A1 | 7/2020 | Kanatzidis et al. | |
| 2020/0264038 A1* | 8/2020 | Shimatani ................ | G01J 1/42 |

(Continued)

OTHER PUBLICATIONS

Kim et al. "Halide Perovskites for Application beyond Photovoltaics", Wiley-VCH Veriag GmbH & Co. KGaA, Weinheim, Small Methods 2018, 2, 1700310, p. 1-20 (Year: 2018).*

(Continued)

*Primary Examiner* — David P Porta
*Assistant Examiner* — Mamadou Faye
(74) *Attorney, Agent, or Firm* — CASIMIR JONES S.C.; Thomas A. Isenbarger

(57) ABSTRACT

Provided herein are technologies relating to detecting x-rays and particularly, but not exclusively, to compositions, devices, systems, and methods for x-ray imaging using a direct-conversion x-ray sensor comprising a perovskite composition that minimizes and/or eliminates in-sensor k-fluorescence in photon energy channels used for medical imaging. Exemplary perovskite compositions described are those that comprise a structure of $ABX_3$, in which A represents an inorganic and/or organic cation, B represents a heavy metal cation, and X represents a halide.

21 Claims, 17 Drawing Sheets

(56) References Cited

U.S. PATENT DOCUMENTS

| | | | |
|---|---|---|---|
| 2020/0379131 A1* | 12/2020 | Saliba | G01T 1/2985 |
| 2020/0381573 A1 | 12/2020 | Kanatzidis et al. | |
| 2021/0020797 A1* | 1/2021 | Fukushima | G01J 1/0295 |
| 2021/0239859 A1* | 8/2021 | Deumel | G01T 1/2023 |

OTHER PUBLICATIONS

Zhao et al. "Ultrasensitive Heterojunctions of Graphene and 2D Perovskites Reveal Spontaneous Iodide Loss", Joule 2, CellPress, Elsevier Inc, 2018, p. 2133-2144. (Year: 2018).*
Alarousu et al., Ultralong Radiative States in Hybrid Perovskite Crystals: Compositions for Submillimeter Diffusion Lengths. J Phys Chem Lett. Sep. 21, 2017;8(18):1-16.
Arnab et al., A Novel Amorphous Selenium Avalanche Detector Structure for Low Dose Medical X-Ray Imaging. IEEE Trans. Radiat. Plasma Med. Sci., 2019; vol. 4, No. 3, pp. 1-10.
Arnab et al., Impact of charge carrier trapping on amorphous selenium direct conversion avalanche X-ray detectors. J. Appl. Phys., 2017; vol. 122, No. 13: 9 pages.
Ballabriga et al., The Medipix3RX: a high resolution, zero dead-time pixel detector readout chip allowing spectroscopic imaging. IOP Publishing for Sissa Medialab. 2013. 17 pages.
Basiricò et al., Direct X-ray photoconversion in flexible organic thin film devices operated below 1 V. Nat Commun. Oct. 6, 2016;7:13063. 1-9.
Berger et al., XCOM: Photon Cross-section Database (Version 3.1), NIST Physical Measurement Laboratory. 2010. www.nist.gov/pml/xcom-photon-cross-sections-database. 2 pages.
Birowosuto et al., "X-ray Scintillation in Lead Halide Perovskite X-ray Scintillation in Lead Halide Perovskite Crystals," Nat. Publ. Gr., No. Nov. 2016. 32 pages.
Chang et al., Ultrahigh Responsivity and Detectivity Graphene-Perovskite Hybrid Phototransistors by Sequential Vapor Deposition. Sci Rep. Apr. 19, 2017;7:46281. 1-10.
De Fazio et al., Graphene-Quantum Dot Hybrid Photodetectors with Low Dark-Current Readout. ACS Nano. Sep. 22, 2020;14(9):11897-11905.
De Fazio et al., High Responsivity, Large-Area Graphene/MoS2 Flexible Photodetectors. ACS Nano. Sep. 27, 2016;10(9):8252-62.
Dirin et al., Solution-Grown CsPbBr3 Perovskite Single Crystals for Photon Detection. Chem Mater. Dec. 13, 2016;28(23):8470-8474.
Dong et al., Solar cells. Electron-hole diffusion lengths > 175 μm in solution-grown CH3NH3PbI3 single crystals. Science. Feb. 27, 2015;347(6225):967-70.
Frey et al., Dark current in multilayer stabilized amorphous selenium based photoconductive x-ray detectors. J. Appl. Phys., 2012; vol. 112, No. 1, pp. 1-10.
Gill et al., Flexible perovskite based X-ray detectors for dose monitoring in medical imaging applications. Phys. Med., 2018; vol. 5, No. May 2018, pp. 20-23.
He et al., High spectral resolution of gamma-rays at room temperature by perovskite CsPbBr3 single crystals. Nat Commun. Apr. 23, 2018;9(1):1609. 1-8.
Heo et al., High-Performance Next-Generation Perovskite Nanocrystal Scintillator for Nondestructive X-Ray Imaging. Adv Mater. Aug. 23, 2018;e1801743. 1-6.
Huang et al., Recent Developments of Amorphous Selenium-Based X-Ray Detectors: A Review. IEEE Sens. J., 2020; vol. 20, No. 4, pp. 1694-1704.
Hunt et al., X-ray imaging using avalanche multiplication in amorphous selenium: investigation of intrinsic avalanche noise. Med Phys. Dec. 2007;34(12):4654-63.
Kabir et al., "Photoconductors for X-Ray Image Detectors," in Springer Handbook of Electronic and Photonic Materials, 2017, pp. 1125-1147.
Kakavelakis et al., Metal Halide Perovskites for High-Energy Radiation Detection. Adv Sci (Weinh). Oct. 11, 2020;7(22):2002098. 1-33.

Kim et al., Printable organometallic perovskite enables large-area, low-dose X-ray imaging. Nature. Oct. 4, 2017;550(7674):87-91.
Knoll, "Radiation Detection and Measurement," 4th ed. John Wiley & Sons, Inc. 2010. TOC only. 6 pages.
Lee et al., High-performance perovskite-graphene hybrid photodetector. Adv Mater. Jan. 7, 2014;27(1):1-6.
Li et al., Scintillation Properties of Perovskite Single Crystals. J. Phys. Chem. C, 2019, 123(28), 17449-17453.
Li et al., The Effect of Thermal Annealing on Charge Transport in Organolead Halide Perovskite Microplate Field-Effect Transistors. Adv Mater. Jan. 2016;29(4).7 pages.
Lille. Chapter 15 Creating the Digital Image, in Mammographic Imaging A Pract. Guid., 2018; pp. 326-357.
Liu et al., The working principle of hybrid perovskite gamma-ray photon counter. Mater. Today, 2020. vol. 37, pp. 27-34.
Liu et al., Triple-Cation and Mixed-Halide Perovskite Single Crystal for High-Performance X-ray Imaging. Adv Mater. Feb. 2021;33(8):e2006010. 1-10.
Maddalena et al., Inorganic, Organic, and Perovskite Halides with Nanotechnology for High—Light Yield X- and γ-ray Scintillators, Crystals, 2019; vol. 9, 88, 1-29.
Murty. Effective Atomic Numbers of Heterogeneous Materials. Nature 1965; 207 (4995): 398-99.
Mykhaylyk et al., Bright and fast scintillation of organolead perovskite MAPbBr 3 at low temperatures. Mater. Horizons, 2019, 6, 1740-1747.
Náfrádi et al., Methylammonium Lead Iodide for Efficient X-ray Energy Conversion. J. Phys. Chem. C 2015, 119, 45, 18 pages.
Nazarenko et al., Single crystals of caesium formamidinium lead halide perovskites: Solution growth and gamma dosimetry. NPG Asia Mater., 2017; vol. 9, No. 4, e373; 8 pages.
Pan et al., Cs2AgBiBr6 single-crystal X-ray detectors with a low detection limit. Nat. Photonics, 2017; vol. 11, No. 11, pp. 726-732.
Panneerselvam. Evaluation of organic perovskite photoconductors for x-ray imaging detectors Dhilippan Mamsapuram Panneerselvam A Thesis in the Department of Electrical and Computer Engineering. Concordia University, 2017. 71 pages.
Park. Halide perovskite photovoltaics: History, progress, and perspectives. MRS Bull., 2018; vol. 43, No. 7, pp. 527-533.
Qian. Fundamentals of digital mammography. Phys. Mammographic Imaging, 2012, pp. 3-10.
Roberts. Lanthanum Halide and Cerium Bromide Scintillators, in Solid-State Radiation Detectors: Technology and Applications., Devices, C. CRC Press, 2015. pp. 261-284.
Saidaminov et al., High-quality bulk hybrid perovskite single crystals within minutes by inverse temperature crystallization. Nat Commun. Jul. 6, 2015;6:7586. pp. 1-6.
Sassi et al., Graphene-based mid-infrared room-temperature pyroelectric bolometers with ultrahigh temperature coefficient of resistance. Nat Commun. Jan. 31, 2017;8:14311. 1-10.
Scheuermann et al., Low dose digital X-ray imaging with avalanche amorphous selenium. Phys. Med. Imaging, 2015. vol. 9412, No. 1, p. 94120E. 1-9.
Scheuermann et al., Toward Scintillator High-Gain Avalanche Rushing Photoconductor Active Matrix Flat Panel Imager (SHARP-AMFPI): Initial fabrication and characterization. Med Phys. Feb. 2018;45(2):794-802. 23 pages.
Schulman, Si , CdTe and CdZnTe radiation detectors for imaging applications, Dissertation, Department of Physics, University of Helsinki, 2006. 82 pages.
Shao et al., Stable Graphene-Two-Dimensional Multiphase Perovskite Heterostructure Phototransistors with High Gain. Nano Lett. Dec. 13, 2017;17(12): 29 pages.
Shi et al., Low trap-state density and long carrier diffusion in organolead trihalide perovskite single crystals. Science. Jan. 30, 2015;347(6221):519. 31 pages.
Shrestha et al., High-performance direct conversion X-ray detectors based on sintered hybrid lead triiodide perovskite wafers. Nat. Photonics, 2017; vol. 11, No. 7, pp. 436-440.
Shrestha et al., Role of the Metal-Semiconductor Interface in Halide Perovskite Devices for Radiation Photon Counting. ACS Appl Mater Interfaces. Oct. 7, 2020;12(40): 9 pages.

(56) References Cited

OTHER PUBLICATIONS

Taylor et al., Electron interaction with gel dosimeters: effective atomic numbers for collisional, radiative and total interaction processes. Radiat Res. Jan. 2009;171(1):123-6.
Taylor et al., Robust calculation of effective atomic numbers: the Auto-Z(eff) software. Med Phys. Apr. 2012;39(4):1769-78.
Taylor et al., The effective atomic number of dosimetric gels. Australas Phys Eng Sci Med. Jun. 2008;31(2):131-8.
Taylor. Robust determination of effective atomic numbers For electron interactions with TLD-100 and TLD-100H thermoluminescent dosimeters. Nuclear Instruments and Methods in Physics Research Section B: 2011; vol. 269(8): pp. 770-773.
Tisdale et al., Methylammonium Lead Tribromide Single Crystal Detectors towards Robust Gamma-Ray Photon Sensing. Adv. Opt. Mater., 2020; vol. 8, No. 10, pp. 1-9.
Wang et al., Hybrid Graphene-Perovskite Phototransistors with Ultrahigh Responsivity and Gain. Adv. Opt. Mater., 2015; vol. 3, No. 10, pp. 1389-1396.
Wei et al., Halide lead perovskites for ionizing radiation detection. Nat Commun. Mar. 6, 2019;10(1):1066.1-12.
Wei et al., Monolithic integration of hybrid perovskite single crystals with heterogenous substrate for highly sensitive X-ray imaging. Nat. Photonics, 2017; vol. 11, No. 5, pp. 315-321.
Wei et al., Sensitive X-ray detectors made of methylammonium lead tribromide perovskite single crystals. Nat. Photonics, 2016; vol. 10, No. 5, pp. 333-339.
Willemink et al., Photon-counting CT: Technical Principles and Clinical Prospects. Radiology. Nov. 2018;289(2):293-312.
Wu, "X-ray Imaging: Mammography." radiologykey.com/x-ray-imaging-mammography/. Retrieved from the internet Nov. 4, 2022. 1 page.
Yaffe et al., Detectors for digital mammography. Technol. Cancer Res. Treat., 2004; vol. 3, No. 4, pp. 309-324.
Yakunin et al., Detection of gamma photons using solution-grown single crystals of hybrid lead halide perovskites. Nat. Photonics, 2016; vol. 10, pp. 585-589.
Yakunin et al., Detection of X-ray photons by solution-processed organic-inorganic perovskites. Nat Photonics. Jul. 2015;9(7):444-449. 13 pages.
Zambon et al., Spectral response characterization of CdTe sensors of different pixel size with the IBEX ASIC. Nucl. Instruments Methods Phys. Res. Sect. A: Accel. Spectrometers, Detect. Assoc. Equip., 2018; vol. 892, No. February, pp. 106-113.
Zhang et al., Metal Halide Perovskite Nanosheet for X-ray High-Resolution Scintillation Imaging Screens. ACS Nano, 2019; 13, 2, 2520-2525.
Zhuge et al., Lead-free perovskites for X-ray detecting. Sci. Bull., 2017; vol. 62, No. 22, pp. 1491-1493.
Zhumekenov et al., Formamidinium Lead Halide Perovskite Crystals with Unprecedented Long Carrier Dynamics and Diffusion Length. ACS Energy Lett. 2016, 1, 1, 32-37.

\* cited by examiner

PHOTON SENSOR

This application claims priority to U.S. provisional patent application Ser. No. 63/200,484, filed Mar. 10, 2021, which is incorporated herein by reference in its entirety.

STATEMENT REGARDING FEDERALLY SPONSORED RESEARCH OR DEVELOPMENT

This invention was made with government support under 1R43EB032694-01 awarded by the National Institutes of Health. The government has certain rights in the invention.

FIELD

Provided herein is technology relating to detecting x-rays and particularly, but not exclusively, to compositions, devices, systems, and methods for x-ray imaging using a direct-conversion x-ray sensor comprising a perovskite composition.

BACKGROUND

Radiological imaging using x-rays is an important component of medical diagnosis and treatment. However, conventional x-ray sensor technologies used in commercial x-ray detectors are expensive and impose inherent limits on the diagnostic power of x-ray imaging techniques. Accordingly, new x-ray sensing technologies are needed to improve the sensitivity and accuracy of x-ray imaging and to increase patient access to x-ray imaging.

SUMMARY

Accordingly, provided herein are embodiments of an x-ray sensor technology that improves the sensitivity and diagnostic accuracy of x-ray detectors. In some embodiments, the technology provides a perovskite-graphene direct conversion imaging sensor having improved sensitivity relative to conventional sensors. In some embodiments, the technology provides a perovskite photon-counting x-ray sensor with minimized and/or eliminated interference from K-shell fluorescence in the x-ray energy ranges used for medical diagnosis.

For example, in some embodiments, the technology provides an x-ray sensor comprising a metal halide perovskite (organic, inorganic, or combinations thereof). In some embodiments, methods comprise producing the metal halide perovskite using solution methods at room temperature. In some embodiments, the x-ray sensor comprises a graphene substrate layer. In some embodiments, the graphene substrate layer is patterned. In some embodiments, the patterned graphene patterns the perovskite pixel/pad shape and provides an optically transparent electrical pathway. In embodiments of the 1-step processing methods described herein, an x-ray sensor is produced in which graphene is the only material in direct electrical contact with the perovskite surface. In particular, metal electrical materials that contact the graphene are encapsulated from the perovskite layer so that metal degradation does not happen within the perovskite absorbing layer. Asymmetric work-function metals are used to provide an asymmetric electrode system from the source/drain/cathode/anode electrodes in contact with each graphene pixel. In this configuration, graphene simultaneously acts as the nucleation site for perovskite growth, shapes the perovskite, amplifies the signal thru a photoconductive gain mechanism, and performs as the organic electrodes for charge collection without compromising perovskite durability due to metal migration. In some embodiments, both the perovskite photon counter and the perovskite-graphene structure are structured on existing silicon wafer/fabrication-based technologies.

For example, embodiments of the technology provide a photon-counting sensor. In some embodiments, the photon counting sensor comprises a perovskite composition that is compositionally tuned to minimize and/or eliminate k-fluorescence from 20 to 140 keV; a first electrode in electrical communication with the perovskite; and a second electrode in electrical communication with the perovskite. In some embodiments, the first electrode is a through-silicon-via electrode and the second electrode is a common electrode. In some embodiments, the perovskite has a formula $ABX_3$. In some embodiments, A has no k-edge, B is a high-Z material, and X has a k-edge at an energy less than 60 keV (e.g., less than 60, 55, 50, 45, 40, 35, 30, 25, 20, 15, or 10 keV). In some embodiments, X is a halide. In some embodiments, X is bromide, iodide, or chloride. In some embodiments, X comprises a fractional composition of a plurality of halides. In some embodiments, A is an organic cation. In some embodiments, A is an inorganic cation. In some embodiments, A is methylammonium. In some embodiments, A is formamidinium. In some embodiments, A is cesium ion, cadmium ion, or rubidium ion. In some embodiments, A comprises a fractional composition of a plurality of organic and/or inorganic cations. In some embodiments, B is a heavy metal. In some embodiments, B is lead. In some embodiments, B is tin. In some embodiments, the perovskite comprises formamidinium lead tribromide ($FAPbBr_3$). In some embodiments, the perovskite comprises methylammonium lead triiodide ($MAPbI_3$). In some embodiments, the perovskite comprises a single perovskite crystal. In some embodiments, the perovskite is 1 to 5 mm thick (e.g., 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mm thick). In some embodiments, the perovskite has a thickness that varies less than 100 μm (e.g., less than 100, 95, 90, 85, 80, 75, 70, 65, 60, 55, 50, 45, 40, 35, 30, 25, 20, 15, 10, or 5 μm). In some embodiments, the photon-counting sensor provides a single pixel having dimensions of less than 500 μm×less than 500 μm (e.g., less than 500, 450, 400, 350, 300, 250, 200, 150, 100, or 50×less than 500, 450, 400, 350, 300, 250, 200, 150, 100, or 50 μm). In some embodiments, the photon-counting sensor further comprises a photon-counting application-specific integrated circuit (ASIC). In some embodiments, the photon-counting sensor further comprises a photon-counting multi-channel analyzer application-specific integrated circuit (ASIC).

In some embodiments, the technology provides a photon-counting sensor comprising a first perovskite composition; a second perovskite composition; a common electrode in electrical communication with the first perovskite composition and the second perovskite composition; a first sensor electrode in electrical communication with the first perovskite composition; and a second sensor electrode in electrical communication with the second perovskite composition. In some embodiments, the first perovskite composition and/or the second perovskite composition is compositionally tuned to minimize and/or eliminate k-fluorescence from 20 to 140 keV (e.g., approximately 15 to 25 keV (e.g., 15, 16, 17, 18, 19, 20, 21, 22, 23, 24, or 25 keV) to approximately 130 to 150 keV (e.g., 130, 131, 132, 133, 134, 135, 136, 137, 138, 139, 140, 141, 142, 143, 144, 145, 146, 147, 148, 149, or 150 keV)). In some embodiments, the first sensor electrode is electrically isolated from the second perovskite composition. In some embodiments, the second sensor electrode is electrically isolated from the first perovskite composition. In some embodiments, the first perovskite layer absorbs x-ray photons of 60 keV or less (e.g., less than 60, 55, 50, 45, 40, 35, 30, 25, 20, 15, or 10 keV). In some embodiments, the second perovskite layer absorbs x-ray photons of 120 keV or less (e.g., less than 120, 115, 110, 105, 100, 95, 90, 85, 80, 75, 70, 65, 60, 55, or 50 keV). In some embodiments, the first sensor electrode is a through-silicon-via electrode and/or the second sensor electrode is a through-silicon-via electrode. In some embodiments, the first perovskite composition has a formula $ABX_3$. In some embodiments, A of the first perovskite composition has no k-edge, B of the first perovskite composition is a high-Z material, and X of the first perovskite composition has a k-edge at an energy less than 60 keV (e.g., less than 60, 55, 50, 45, 40, 35, 30, 25, 20, 15, or 10 keV). In some embodiments, X of the first perovskite composition is a halide. In some embodiments, X of the first perovskite composition is bromide, iodide, or chloride. In some embodiments, X of the first perovskite composition comprises a fractional composition of a plurality of halides. In some embodiments, A of the first perovskite composition is an organic cation. In some embodiments, A of the first perovskite composition is an inorganic cation. In some embodiments, A of the first perovskite composition is methylammonium. In some embodiments, A of the first perovskite composition is formamidinium. In some embodiments, A of the first perovskite composition is cesium ion, cadmium ion, or rubidium ion. In some embodiments, A of the first perovskite composition comprises a fractional composition of a plurality of organic and/or inorganic cations. In some embodiments, B of the first perovskite composition is a heavy metal. In some embodiments, B of the first perovskite composition is lead. In some embodiments, B of the first perovskite composition is tin. In some embodiments, the first perovskite composition comprises formamidinium lead tribromide ($FAPbBr_3$). In some embodiments, the first perovskite composition comprises methylammonium lead triiodide ($MAPbI_3$). In some embodiments, the second perovskite composition has a formula $ABX_3$. In some embodiments, A of the second perovskite composition has no k-edge, B of the second perovskite composition is a high-Z material, and X of the second perovskite composition has a k-edge at an energy less than 60 keV (e.g., less than 60, 55, 50, 45, 40, 35, 30, 25, 20, 15, or 10 keV). In some embodiments, X of the second perovskite composition is a halide. In some embodiments, X of the second perovskite composition is bromide, iodide, or chloride. In some embodiments, X of the second perovskite composition comprises a fractional composition of a plurality of halides. In some embodiments, A of the second perovskite composition is an organic cation. In some embodiments, A of the second perovskite composition is an inorganic cation. In some embodiments, A of the second perovskite composition is methylammonium. In some embodiments, A of the second perovskite composition is formamidinium. In some embodiments, A of the second perovskite composition is cesium ion, cadmium ion, or rubidium ion. In some embodiments, A of the second perovskite composition comprises a fractional composition of a plurality of organic and/or inorganic cations. In some embodiments, B of the second perovskite composition is a heavy metal. In some embodiments, B of the second perovskite composition is lead. In some embodiments, B of the second perovskite composition is tin. In some embodiments, the second perovskite composition comprises formamidinium lead tribromide ($FAPbBr_3$). In some embodiments, the second perovskite composition comprises methylammonium lead triiodide ($MAPbI_3$). In some embodiments, the first perovskite composition comprises a single perovskite crystal and/or the second perovskite composition comprises a single crystal. In some embodiments, the first perovskite composition is 1 to 5 mm thick (e.g., 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mm thick) and/or the second perovskite composition is 1 to 5 mm thick. In some embodiments, the first perovskite composition has a thickness that varies less than 100 μm (e.g., less than 100, 95, 90, 85, 80, 75, 70, 65, 60, 55, 50, 45, 40, 35, 30, 25, 20, 15, 10, or 5 μm) and/or the second perovskite composition has a thickness that varies less than 100 μm (e.g., less than 100, 95, 90, 85, 80, 75, 70, 65, 60, 55, 50, 45, 40, 35, 30, 25, 20, 15, 10, or 5 μm). In some embodiments, the photon-counting sensor provides a single pixel having dimensions of less than 500 μm (e.g., less than 500, 450, 400, 350, 300, 250, 200, 150, 100, or 50×less than 500, 450, 400, 350, 300, 250, 200, 150, 100, or 50 μm)×less than 500 μm (e.g., less than 500, 450, 400, 350, 300, 250, 200, 150, 100, or 50×less than 500, 450, 400, 350, 300, 250, 200, 150, 100, or 50 μm). In some embodiments, the photon-counting sensor further comprises a photon-counting application-specific integrated circuit (ASIC). In some embodiments, the photon-counting sensor comprises a photon-counting multi-channel analyzer application-specific integrated circuit (ASIC).

The technology further provides embodiments of a detector comprising an array of photon-counting sensors as described herein (e.g., a photon counting sensor comprising a perovskite composition that is compositionally tuned to minimize and/or eliminate k-fluorescence from 20 to 140 keV; a first electrode (e.g., a through-silicon-via electrode) in electrical communication with the perovskite; and a second electrode (e.g., common electrode) in electrical communication with the perovskite; or a photon-counting sensor comprising a first perovskite composition; a second perovskite composition; a common electrode in electrical communication with the first perovskite composition and the second perovskite composition; a first sensor electrode in electrical communication with the first perovskite composition; and a second sensor electrode in electrical communication with the second perovskite composition). In some embodiments, the detector comprises at least 100 photon-counting sensors; at least 1000 photon-counting sensors; at least 10,000 photon-counting sensors; at least 100,000 photon-counting sensors; or at least 1,000,000 photon-counting sensors.

In some embodiments, the technology provides a direct conversion sensor comprising a graphene; and a perovskite provided directly on the graphene surface. In some embodiments, the direct conversion sensor is an energy integrating sensor. In some embodiments, a graphene field effect transistor comprises the graphene. In some embodiments, the perovskite is compositionally tuned to minimize and/or eliminate k-fluorescence from 20 to 140 keV (e.g., approximately 15 to 25 keV (e.g., 15, 16, 17, 18, 19, 20, 21, 22, 23, 24, or 25 keV) to approximately 130 to 150 keV (e.g., 130, 131, 132, 133, 134, 135, 136, 137, 138, 139, 140, 141, 142, 143, 144, 145, 146, 147, 148, 149, or 150 keV)). In some embodiments, the perovskite is a single crystal. In some embodiments, the perovskite is a single crystal grown on a surface of the graphene. In some embodiments, the graphene field effect transistor comprises a substrate; a back-gate; a gate dielectric, source-drain edge contacts; an encapsulant (e.g., $Al_2O_3$); and said graphene. In some embodiments, the graphene is patterned. In some embodiments, the direct conversion sensor further comprises a protective layer contacting the perovskite. In some embodiments, the direct conversion sensor is unbiased. In some embodiments, a perovskite-graphene interface between the perovskite and the graphene is unbiased. In some embodiments, a work function differential between the perovskite and graphene at the perovskite-graphene interface generates an internal field that moves electrons and/or holes. In some embodiments, the perovskite has a formula $ABX_3$. In some embodiments, A has no k-edge, B is a high-Z material, and X has a k-edge at an energy less than 60 keV (e.g., less than 60, 55, 50, 45, 40, 35, 30, 25, 20, 15, or 10 keV). In some embodiments, X is a halide. In some embodiments, X is bromide, iodide, or chloride. In some embodiments, X comprises a fractional composition of a plurality of halides. In some embodiments, A is an organic cation. In some embodiments, A is an inorganic cation. In some embodiments, A is methylammonium. In some embodiments, A is formamidinium. In some embodiments, A is cesium ion, cadmium ion, or rubidium ion. In some embodiments, A comprises a fractional composition of a plurality of organic and/or inorganic cations. In some embodiments, B is a heavy metal. In some embodiments, B is lead. In some embodiments, B is tin. In some embodiments, the perovskite comprises formamidinium lead tribromide ($FAPbBr_3$). In some embodiments, the perovskite comprises methylammonium lead triiodide ($MAPbI_3$). In some embodiments, the perovskite is 1 to 5 mm thick (e.g., 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mm thick). In some embodiments, the perovskite has a thickness that varies less than 100 µm (e.g., less than 100, 95, 90, 85, 80, 75, 70, 65, 60, 55, 50, 45, 40, 35, 30, 25, 20, 15, 10, or 5 µm). In some embodiments, the photon-counting sensor provides a single pixel having dimensions of less than 500 µm×less than 500 µm (e.g., less than 500, 450, 400, 350, 300, 250, 200, 150, 100, or 50×less than 500, 450, 400, 350, 300, 250, 200, 150, 100, or 50 µm). In some embodiments, the direct conversion sensor further comprises a photon-counting application-specific integrated circuit (ASIC). In some embodiments, the direct conversion sensor further comprises a photon-counting multi-channel analyzer application-specific integrated circuit (ASIC).

The technology further provides embodiments of a detector comprising an array of direct conversion sensors as described herein (e.g., a direct conversion sensor comprising a graphene; and a perovskite provided directly on the graphene surface). In some embodiments, the detector comprises at least 100 direct conversion sensors; at least 1000 direct conversion sensors; at least 10,000 direct conversion sensors; at least 100,000 direct conversion sensors; or at least 1,000,000 direct conversion sensors.

The technology further provides methods for producing a direct conversion sensor. In some embodiments, methods comprise depositing a perovskite directly on a graphene surface of a graphene field effect transistor. In some embodiments, depositing a perovskite directly on a graphene surface of a graphene field effect transistor comprises growing a perovskite crystal directly on the graphene surface of the graphene field effect transistor. In some embodiments, depositing a perovskite directly on a graphene surface comprises using spin coating, doctor blade coating, hot casting, printing deposition, tape casting, or an inverse temperature method. In some embodiments, methods comprise placing a back-gate on a substrate; depositing a gate dielectric on the back-gate and/or substrate; exposing a contact of the back-gate; depositing graphene and/or patterning graphene on the dielectric; producing contacts on the graphene; encapsulating the contacts in an encapsulant (e.g., $Al_2O_3$); and depositing a perovskite directly on a surface of a graphene (e.g., using spin coating, doctor blade coating, hot casting, printing deposition, tape casting, or an inverse temperature method). In some embodiments, the back-gate comprises Au or Cr/Au. In some embodiments, the substrate comprises a silicon wafer. In some embodiments, the substrate is covered with a layer of $SiO_2$. In some embodiments, the layer of $SiO_2$ is approximately 90 nm thick (e.g., 80, 81, 82, 83, 84, 85, 86, 87, 88, 89, 90, 91, 92, 93, 94, 95, 96, 97, 98, 99, or 100 nm thick). In some embodiments, placing a back-gate on a substrate comprises electrically isolating a plurality of back-gates from each other. In some embodiments, electrically isolating a plurality of back-gates from each other comprises using optical lithography and metallization of Cr/Au via thermal/e-beam evaporation. In some embodiments, the gate dielectric comprises $Al_2O_3$. In some embodiments, depositing a gate dielectric comprises use of atomic layer deposition. In some embodiments, exposing a back-gate contact comprises using optical lithography and wet etching of the dielectric. In some embodiments, depositing graphene and/or patterning graphene comprises using optical lithography and/or etching. In some embodiments, etching is $O_2$ reactive ion etching. In some embodiments, depositing graphene and/or patterning graphene produces channels in the graphene. In some embodiments, producing contacts on the graphene comprises using optical lithography and metallization of Cr/Au via thermal/e-beam evaporation. In some embodiments, the contacts on the graphene comprise source-drain edge contacts. In some embodiments, encapsulating the contacts comprises encapsulating the contacts in $Al_2O_3$. In some embodiments, depositing a perovskite directly on a surface of a graphene comprises using a hot-casting technique. In some embodiments, depositing a perovskite directly on a surface of a graphene comprises using spin coating, doctor blade coating, hot casting, printing deposition, tape casting, or an inverse temperature method. In some embodiments, methods further comprise patterning the perovskite to isolate the perovskite over each graphene pixel. In some embodiments, patterning the perovskite comprises using laser scribing. In some embodiments, methods further comprise depositing a protection layer on the perovskite. In some embodiments, the protection layer comprises $Al_2O_3$ or a polymer. In some embodiments, the polymer comprises polymethyl methacrylate. In some embodiments, methods further comprise attaching a chip carrier. In some embodiments, methods further comprise attaching a printed circuit board (PCB). In some embodiments, attaching a PCB comprises soldering. In some embodiments, methods further comprise wire bonding GFET electrodes to the PCB. In some embodiments, the PCB comprises connections for attachment to external components. In some embodiments, the connections comprise BNC connections. In some embodiments, methods further comprise electrically connecting said direct conversion sensor to an external data acquisition component. In some embodiments, the external data acquisition component is a digital acquisition component.

The technology further relates to systems. For example, in some embodiments, the technology provides a system comprising a perovskite-graphene direct conversion sensor or a perovskite photon-counting sensor. In some embodiments, the perovskite photon-counting sensor comprises: a perovskite composition that is compositionally tuned to minimize and/or eliminate k-fluorescence from 20 to 140 keV (e.g., approximately 15 to 25 keV (e.g., 15, 16, 17, 18, 19, 20, 21, 22, 23, 24, or 25 keV) to approximately 130 to 150 keV (e.g., 130, 131, 132, 133, 134, 135, 136, 137, 138, 139, 140, 141, 142, 143, 144, 145, 146, 147, 148, 149, or 150 keV)); a first electrode in electrical communication with the perovskite; and a second electrode in electrical communication with the perovskite. In some embodiments, the perovskite photon-counting sensor comprises a first perovskite composition; a second perovskite composition; a common electrode in electrical communication with the first perovskite composition and the second perovskite composition; a first sensor electrode in electrical communication with the first perovskite composition; and a second sensor electrode in electrical communication with the second perovskite composition. In some embodiments, the perovskite-graphene direct conversion sensor comprises a graphene; and a perovskite provided directly on the graphene surface. In some embodiments, the perovskite-graphene direct conversion sensor comprises a graphene field effect transistor comprising a graphene surface; and a perovskite provided directly on the graphene surface. In some embodiments, systems further comprise an external data acquisition component. In some embodiments, the external data acquisition component is a digital acquisition component. In some embodiments, systems further comprise a source; and a detector comprising said perovskite-graphene direct conversion sensor or a detector comprising said perovskite photon-counting sensor. In some embodiments, systems further comprise an object to be imaged. In some embodiments, the object is a patient. In some embodiments, systems further comprise an anti-scatter device. In some embodiments, systems further comprise an imaging display. In some embodiments, systems further comprise software. In some embodiments, the software comprises instructions for receiving x-ray intensity and/or energy information from the detector, converting the intensity and/or energy information into an image, and providing the image on a display.

Additional embodiments will be apparent to persons skilled in the relevant art based on the teachings contained herein.

BRIEF DESCRIPTION OF THE DRAWINGS

FIG. 1 is a schematic drawing of a single-layer perovskite sensor comprising electrodes and a perovskite composition that is compositionally tuned to minimize and/or eliminate k-fluorescence.

Figure 2:
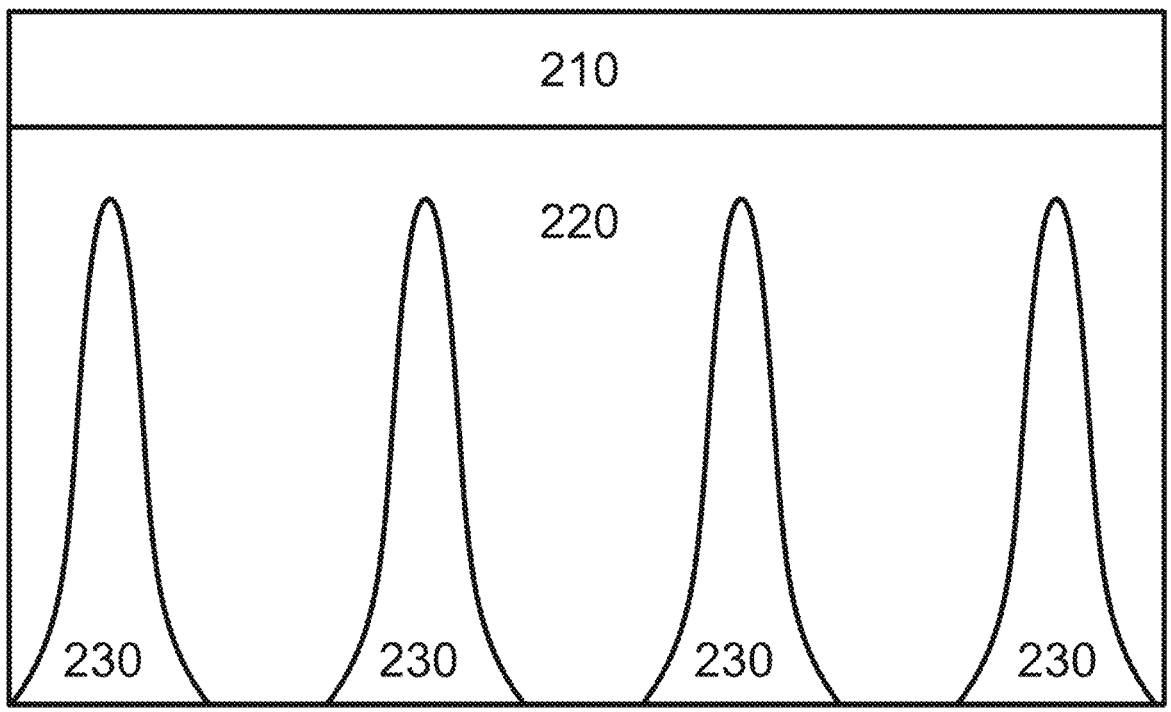
FIG. 2 is a schematic drawing of a single-layer perovskite sensor comprising through-silicon-via (TSV) electrodes for each pixel of a readout integrated circuit (ROIC) and a perovskite composition that is compositionally tuned to minimize and/or eliminate k-fluorescence.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

As described herein, the technology provides embodiments of an x-ray sensor technology that improves the sensitivity and accuracy of x-ray detectors. In some embodiments, the technology provides a perovskite-graphene direct conversion imaging sensor having improved sensitivity relative to conventional sensors. In some embodiments, the technology provides a photon-counting x-ray sensor with minimized and/or eliminated interference from K-shell fluorescence in the x-ray energy ranges used for medical diagnosis.

In some embodiments, the technology described herein finds use in spectral photon counting or energy integrating detection, e.g., for medical imaging. Accordingly, the technology finds use in radiography, x-ray imaging, tomography (e.g., computed tomography), nuclear medicine, mammography, and/or fluoroscopic imaging. In some embodiments, the technology finds use as a nuclide sensor for detecting and/or measuring nuclear materials or high energy charged particles. Thus, in some embodiments, the technology finds use in portable or benchtop radiation detectors. In some embodiments, the technology finds use in dosimetry.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used, "about" and "approximately" mean plus or minus less than or equal to 10% of the particular term and "substantially" and "significantly" mean plus or minus greater than 10% of the particular term.

As used herein, disclosure of ranges includes disclosure of all values and further divided ranges within the entire range, including endpoints and sub-ranges given for the ranges. As used herein, the disclosure of numeric ranges includes the endpoints and each intervening number therebetween with the same degree of precision. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "mixing-free" method does not comprise a mixing step, etc.

Although the terms "first", "second", "third", etc. may be used herein to describe various steps, elements, compositions, components, regions, layers, and/or sections, these steps, elements, compositions, components, regions, layers, and/or sections should not be limited by these terms, unless otherwise indicated. These terms are used to distinguish one step, element, composition, component, region, layer, and/or section from another step, element, composition, component, region, layer, and/or section. Terms such as "first", "second", and other numerical terms when used herein do not imply a sequence or order unless clearly indicated by the context. Thus, a first step, element, composition, component, region, layer, or section discussed herein could be termed a second step, element, composition, component, region, layer, or section without departing from technology.

As used herein, the word "presence" or "absence" (or, alternatively, "present" or "absent") is used in a relative sense to describe the amount or level of a particular entity (e.g., component, action, element). For example, when an entity is said to be "present", it means the level or amount of this entity is above a pre-determined threshold; conversely, when an entity is said to be "absent", it means the level or amount of this entity is below a pre-determined threshold. The pre-determined threshold may be the threshold for detectability associated with the particular test used to detect the entity or any other threshold. When an entity is "detected" it is "present"; when an entity is "not detected" it is "absent".

As used herein, an "increase" or a "decrease" refers to a detectable (e.g., measured) positive or negative change, respectively, in the value of a variable relative to a previously measured value of the variable, relative to a pre-established value, and/or relative to a value of a standard control. An increase is a positive change preferably at least 10%, more preferably 50%, still more preferably 2-fold, even more preferably at least 5-fold, and most preferably at least 10-fold relative to the previously measured value of the variable, the pre-established value, and/or the value of a standard control. Similarly, a decrease is a negative change preferably at least 10%, more preferably 50%, still more preferably at least 80%, and most preferably at least 90% of the previously measured value of the variable, the pre-established value, and/or the value of a standard control. Other terms indicating quantitative changes or differences, such as "more" or "less," are used herein in the same fashion as described above.

As used herein, the term "radiation source" or "source" refers to an apparatus that produces radiation (e.g., ionizing radiation) in the form of photons (e.g., described as particles or waves). In some embodiments, a radiation source is a linear accelerator ("linac") that produces x-rays. In some embodiments, the source produces particles (e.g., photons, electrons, neutrons, hadrons, ions (e.g., protons, carbon ions, other heavy ions)). In some embodiments, the source produces electromagnetic waves (e.g., x-rays and gamma rays having a wavelength in the range of approximately 1 pm to approximately 1 nm). While it is understood that radiation can be described as having both wave-like and particle-like aspects, it is sometimes convenient to refer to radiation in terms of waves and sometimes convenient to refer to radiation in terms of particles. Accordingly, both descriptions are used throughout without limiting the technology and with an understanding that the laws of quantum mechanics provide that every particle or quantum entity may be described as either a particle or a wave.

As used herein, the term "stopping power" refers to the retarding force acting on a charged particle due to the interaction of the particle with matter, which results in the particle losing energy. Stopping power can be defined as the rate of energy lost per unit of path length (x) by a charged particle with kinetic energy (E) in a medium having an atomic number of $Z_{eff}$.

As used herein, the term "in-sensor fluorescence" refers to the fluorescence of elements in a photon sensor (e.g., x-ray sensor) caused by the emission of secondary x-rays (also known as "characteristic x-rays") from a sensor material that has been excited by high-energy particles (e.g., x-ray photons). When an incident particle (e.g., an x-ray photon from the primary beam produced by a radiological imaging x-ray source) ejects a bound electron from an inner energy shell of an atom, a vacant energy level remains. Outer-shell electrons fill the vacancy in the inner energy shell, emitting photons at a quantized energy level that is the energy difference between the energy of the outer shell and inner shell. Each element has a unique set of energy levels (e.g., designated in Siegbahn notation using letters such as K, L, and M), and thus the energy difference between the energy of the outer electron shell (e.g., M, L) and the inner electron shell (e.g., K) produces x-rays with frequencies that are characteristic to each element ("characteristic x-rays"). In particular, as used herein, the term "k-fluorescence" refers to the characteristic x-rays emitted by an element when electrons fill a vacant K-shell (e.g., after transitioning from a higher-energy shell (e.g., an M shell, an L shell)). The National Institute of Standards and Technology provides databases of calculated and empirically determined x-ray transition energies and characteristic x-ray energies for most elements (e.g., at physics.nist.gov).

As used herein, the term "informative" (e.g., "informative photons", "informative x-rays", "informative energy channels") refers to photons (e.g., x-ray photons) that may be used to produce an accurate image of an object being imaged (e.g., a patient) using x-ray imaging. For example, photons or x-rays produced by the beam of an x-ray imaging apparatus that are attenuated by passage through the object being imaged (e.g., a patient) provide informative photons or informative x-rays. The energies of informative photons may be referred to as "informative energy channels". Informative energy channels for medical imaging are typically in the range of approximately 20 keV to 140 keV (e.g., 20, 30, 40, 50, 60, 80, 100, 120, and 140 keV). Energy channels that are obscured or that have minimized utility for imaging are not informative energy channels. For instance, energy channels in which sensor materials produce k-fluorescence are not informative energy channels if the k-fluorescence overlaps and/or obscures the energy channels of the signal produced by photons or x-rays produced by the beam of an x-ray imaging apparatus that are attenuated by passage through the object being imaged (e.g., a patient) and detected by the detector.

As used herein, the term "spectral efficiency" refers to the fraction of informative photons originating from the source, passing through the patient, and detected by the detector as a fraction of the total number of photons detected by the detector. Photons produced by k-fluorescence in a detector and detected by the detector are not informative photons and thus decrease spectral efficiency.

As used herein, the term "compositionally tuned to minimize and/or eliminate k-fluorescence" refers to a material having a controlled composition (e.g., a controlled composition of elements) so that the material does not produce k-fluorescence in informative energy channels (e.g., used for medical imaging). Some materials that are compositionally tuned to minimize and/or eliminate k-fluorescence produce k-fluorescence, but the k-fluorescence is produced in energy channels that are not used for the particular imaging tasks for which the compositionally tuned material was produced and used.

As used herein, the term "Z" refers to an atomic number (e.g., of an element and/or of a material comprising an element). As used herein, the "Z" of a material refers to the atomic number of the element or elements from which the material is made.

As used herein, the term "effective atomic number" or "$Z_{eff}$" refers to the effective or average atomic number for a compound or mixture of materials (e.g., an alloy). The $Z_{eff}$ may be determined experimentally or estimated according to calculations described by Murty (1965) "Effective Atomic Numbers of Heterogeneous Materials" Nature 207 (4995): 398-99; Taylor (2008) "The effective atomic number of dosimetric gels" Australasian Physics & Engineering Sciences in Medicine 31 (2): 131-38; Taylor (2009) "Electron Interaction with Gel Dosimeters: Effective Atomic Numbers for Collisional, Radiative and Total Interaction Processes" Radiation Research 171 (1): 123-26; Taylor (2011) "Robust determination of effective atomic numbers for electron interactions with TLD-100 and TLD-100H thermoluminescent dosimeters" Nuclear Instruments and Methods in Physics Research Section B: Beam Interactions with Materials and Atoms 269 (8): 770-73; and Taylor (2012) "Robust calculation of effective atomic numbers: The Auto-$Z_{eff}$ software" Medical Physics 39 (4): 1769-78, each of which is incorporated herein by reference. The Auto-$Z_{eff}$ software described by Taylor is freely available for use in calculating the $Z_{eff}$ of compounds or mixtures of materials.

As used herein, the term "high-Z element" refers to a chemical element that comprises a large number of protons in the nucleus, e.g., a chemical element having an atomic number that is 12 or more (e.g., 12 to 83). Exemplary high-Z chemical elements include, but are not limited to, copper (Cu), aluminum (Al), iron (Fe), titanium (Ti), tungsten (W), tantalum (Ta), lead (Pb), tin (Sn), antimony (Sb), and bismuth (Bi).

As used herein, the term "low-Z element" refers to a chemical element that comprises a small number of protons in the nucleus, e.g., a chemical element having an atomic number that is from 1 to 11. Exemplary low-Z chemical elements include but are not limited to beryllium (Be), boron (B), carbon (C), hydrogen (H), oxygen (O), and nitrogen (N).

As used herein, the term "high-Z material" refers to a material comprising a "high-Z" chemical element, e.g., a material that is a pure, substantially pure, and/or effectively pure high-Z chemical element; and/or a material comprising at least 50% by weight (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9%) of a high-Z chemical element. In some embodiments, a high-Z material is a mixture, composite, alloy, ceramic, oxide, and/or a polymer comprising at least 50% by weight (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9%) of a high-Z chemical element. In some embodiments, a high-Z material comprises embedded particles of a high-Z chemical element or a combination of high-Z chemical elements. In some embodiments, a high-Z material comprises a combination of two or more high-Z chemical elements, e.g., a material comprising two or more pure, substantially pure, and/or effectively pure high-Z chemical elements; or a material comprising at least 50% by weight (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9%) of a combination of two or more high-Z chemical elements (e.g., in a mixture, composite, alloy, ceramic, oxide, and/or a polymer). A "high-Z material" may also be a material (e.g., a compound or mixture (e.g., an alloy)) that has a $Z_{eff}$ similar to a high-Z element, e.g., a $Z_{eff}$ that is 12 or more (e.g., 12 to 83).

As used herein, the term "low-Z material" refers to a material comprising a "low-Z" chemical element, e.g., a material that is a pure, substantially pure, and/or effectively pure low-Z chemical element; a molecule comprising low-Z chemical elements connected by chemical bonds; and/or a material comprising at least 50% by weight (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9%) of a low-Z chemical element or a molecule comprising low-Z chemical elements connected by chemical bonds. In some embodiments, a low-Z material is a mixture, composite, ceramic, oxide, and/or a polymer comprising at least 50% by weight (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9%) of a low-Z chemical element or a molecule comprising low-Z chemical elements connected by chemical bonds. In some embodiments, a low-Z material comprises embedded particles of a low-Z chemical element or a molecule comprising low-Z chemical elements connected by chemical bonds; or comprises embedded particles comprising a combination of low-Z chemical elements or molecules comprising low-Z chemical elements connected by chemical bonds. In some embodiments, a low-Z material comprises a combination of two or more low-Z chemical elements or molecules comprising low-Z chemical elements connected by chemical bonds, e.g., a material comprising two or more pure, substantially pure, and/or effectively pure low-Z chemical elements or molecules comprising low-Z chemical elements connected by chemical bonds; or a material comprising at least 50% by weight (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9%) of a combination of two or more low-Z chemical elements or molecules comprising low-Z chemical elements connected by chemical bonds (e.g., in a mixture, composite, alloy, ceramic, oxide, and/or a polymer). A "low-Z material" may also be a material (e.g., a compound or mixture (e.g., an alloy)) that has a $Z_{eff}$ similar to a low-Z element, e.g., a $Z_{eff}$ that is from 1 to 11.

As used herein, the term "electrical communication" refers to a connection and/or contact between a first component and a second component that allows flow of electrons between the first component and the second component (e.g., from the first component to the second component and/or from the second component to the first component), and this means that electrons can flow between components in electrical communication with each other. Two components that are in "electrical communication" may include additional components (e.g., conductors, contacts, wires, circuits, resistors, capacitors, transistors, semiconductors, etc.) located in the electrical path between the two components. Thus, the term "electrical communication" encompasses both direct electron flow between two components or end points and indirect electron flow that includes passing through one or more intermediate components. Two components that are in "direct electrical communication" may be in "electrical communication" with one another and in physical contact with one another.

As used herein, the term "electrically isolated" refers to a component that is not in electrical communication. For example, a first component that is electrically isolated from a second component does not electrically communicate (e.g., does not effectively and/or substantially electrically communicate) with the second component. An electrical insulator or a dielectric material may be placed between two components to electrically isolate the two components from one another.

As used herein, a "system" refers to a plurality of real and/or abstract components operating together for a common purpose. In some embodiments, a "system" is an integrated assemblage of hardware and/or software components. In some embodiments, each component of the system interacts with one or more other components and/or is related to one or more other components. In some embodiments, a system refers to a combination of components and software for controlling and directing methods. For example, a "system" or "subsystem" may comprise one or more of, or any combination of, the following: mechanical devices, hardware, components of hardware, circuits, circuitry, logic design, logical components, software, software modules, components of software or software modules, software procedures, software instructions, software routines, software objects, software functions, software classes, software programs, files containing software, etc., to perform a function of the system or subsystem. Thus, the methods and apparatus of the embodiments, or certain aspects or portions thereof, may take the form of program code (e.g., instructions) embodied in tangible media, such as floppy diskettes, CD-ROMs, hard drives, flash memory, or any other machine-readable storage medium wherein, when the program code is loaded into and executed by a machine, such as a computer, the machine becomes an apparatus for practicing the embodiments. In the case of program code execution on programmable computers, the computing device generally includes a processor, a storage medium readable by the processor (e.g., volatile and non-volatile memory and/or storage elements), at least one input device, and at least one output device. One or more programs may implement or utilize the processes described in connection with the embodiments, e.g., through the use of an application programming interface (API), reusable controls, or the like. Such programs are preferably implemented in a high-level procedural or object-oriented programming language to communicate with a computer system. However, the program(s) can be implemented in assembly or machine language, if desired. In any case, the language may be a compiled or interpreted language, and combined with hardware implementations.

Perovskite

Embodiments of the technology relate to x-ray sensors comprising a perovskite semiconductor. A perovskite is a compound having a general formula $ABX_3$ and that forms a nearly cubic (e.g., orthorhombic) crystal structure similar to the crystal structure of the mineral named perovskite ($CaTiO_3$), which was the first member identified in this class of compounds and for which the class of perovskite compounds is named. In the crystal, A is a cation that resides at the cube corner of the crystal unit cell, B is a cation that resides at the body center of the crystal unit cell, and X is an anion that resides at a face centered position in the unit cell and bonds to both cations. While the A cation is typically an alkaline earth metal or rare-earth element, the B cation is typically a transition metal, and X is typically an oxygen, perovskites as described herein are not limited to these particular types of ions in the A, B, and/or X positions. For example, embodiments of the technology provided herein relate to perovskites having a formula $ABX_3$ in which A is an organic cation (e.g., methylammonium ("MA"), formamidinium ("FA")), B is a lead cation, and X is a halide anion (e.g., chloride, bromide, iodide).

Perovskites have characteristics appropriate for x-ray sensors and x-ray detectors, e.g., high x-ray stopping power, efficient charge transfer, and easy synthesis [36]. The x-ray stopping power of a perovskite depends on the effective atomic number ($Z_{eff}$) of the perovskite, which in turn depends on the composition (e.g., the A, B, and X components) of the perovskite [36]. However, while the $Z_{eff}$ of a perovskite varies with the composition of the perovskite, the $Z_{eff}$ of perovskites is generally significantly greater than that the $Z_{eff}$ of conventional materials used for X-ray detection. For instance, the $Z_{eff}$ of methylammonium lead halide perovskites (e.g., $MAPbI_3$ and $MAPbBr_3$) is approximately 67, which is greater than the $Z_{eff}$ of silicon ($Z_{eff}$=14), amorphous selenium ($Z_{eff}$=34), cadmium zinc telluride ($Z_{eff}$=49), and thallium-doped sodium iodide ($Z_{eff}$=51). Accordingly, embodiments of the technology provide perovskites with a $Z_{eff}$ greater than 50 (e.g., $Z_{eff}$ greater than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80); embodiments of the technology provide perovskites with a $Z_{eff}$ greater than 60 (e.g., $Z_{eff}$ greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90); and embodiments of the technology provide perovskites with a $Z_{eff}$ greater than 70 (e.g., $Z_{eff}$ greater than 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100).

Further, mobility and charge recombination lifetime measurements show a sizeable mu-tau product of $1.2 \times 10^{-2}$ $cm^2 \times V^{-1}$ and thus a long diffusion length of up to 175 µm [46]. High-quality perovskite single crystals can be grown from low-cost solution processes [51] at a temperature lower than temperatures used to produce conventional x-ray detector crystals such as amorphous selenium (a-Se) and cadmium zinc telluride (CZT). The material cost for 1 $cm^3$ of single-crystal perovskite is approximately \$0.50 to \$1.00 [33]. Without considering economy of scale, single-crystal perovskite production is approximately three orders of magnitude less expensive than the cost of producing CZT crystals.

For instance, U.S. patent application Ser. Nos. 16/649,862 and 16/644,404, each of which is incorporated herein by reference, describe perovskite compositions for use in x-ray imaging. In contrast to previously described perovskite compositions, embodiments of the technology described herein relate to perovskite compositions for x-ray imaging that are designed and synthesized to minimize and/or eliminate in-sensor K-edge fluorescence and/or to move K-edge fluorescence to energies outside the informative energy channels of interest for medical imaging, e.g., energy channels used to detect imaging contrast agents, ligand assisted encapsulated heavy metal nanoparticles, or human tissue types of interest in x-ray photon counting imaging. Further, in contrast to previous sensors comprising perovskites, embodiments of the technology described herein relate to sensors comprising a single-layer perovskite composition or a dual-layer perovskite composition including thru-silicon-via electrodes as described herein. Moreover, embodiments of the technology described herein provide sensors comprising a uniform layer of perovskite deposited on a surface or multiple uniform layers of perovskite provided on a surface. In some embodiments, embodiments of the technology described herein provide sensors comprising a uniform layer of perovskite (e.g., a perovskite crystal) grown directly on a graphene substrate (e.g., a GFET). In some embodiments, growing a perovskite crystal directly on the graphene surface of the graphene field effect transistor comprises using a doctor blade method, tape casting, or an inverse temperature method.

Embodiments of the technology provided herein relate to a perovskite composition, having a general formula $ABX_3$. In some embodiments, X has a relatively low energy K-edge (e.g., bromide, chloride, and/or iodide) that places the x-ray in-sensor k-fluorescence energy relatively close to the incident x-ray photon energy. In some embodiments, X is a fractional combination of one or more X anions to provide a specific sensor having minimized and/or eliminated k-fluorescence in a specific energy channel of interest for a particular imaging task. For example, embodiments comprise a perovskite composition having a formula $AB(XX')_3$ where the fractional composition of X ranges from 0 to 1 and the fractional composition of X' ranges concomitantly from 1 to 0, e.g., $AB(X)_3$, $AB(X_{0.9}X'_{0.1})_3$, $AB(X_{0.8}X'_{0.2})_3$, $AB(X_{0.7}X'_{0.3})_3$, $AB(X_{0.6}X'_{0.4})_3$, $AB(X_{0.5}X'_{0.5})_3$, $AB(X_{0.4}X'_{0.6})_3$, $AB(X_{0.3}X'_{0.7})_3$, $AB((X_{0.2}X'_{0.8})_3$, $AB(X_{0.1}X'_{0.9})_3$, or $AB(X')_3$. A and B may also have fractional composition as described herein.

In some embodiments, A has no k-edge and/or has substantially or essentially no k-edge (e.g., an organic cation (e.g., methylammonium (MA), formamidinium (FA), or combinations thereof) or an inorganic cation (e.g., cesium (Cs) and/or rubidium (Rb)). In some embodiments, A is a fractional combination of one or more organic cations, one or more inorganic cations, or a fractional combination of one or more organic cations and one or more inorganic cations. For example, embodiments comprise a perovskite composition having a formula $AA'BX_3$ where the fractional composition of A ranges from 0 to 1 and the fractional composition of A' ranges concomitantly from 1 to 0, e.g., $ABX_3$, $A_{0.9}A'_{0.1}BX_3$, $A_{0.8}A'_{0.2}BX_3$, $A_{0.7}A'_{0.3}BX_3$, $A_{0.6}A'_{0.4}BX_3$, $A_{0.5}A'_{0.5}BX_3$, $A_{0.4}A'_{0.6}BX_3$, $A_{0.3}A'_{0.7}BX_3$, $A_{0.2}A'_{0.8}BX_3$, $A_{0.1}A'_{0.9}BX_3$, or $A'BX_3$. For example, in some embodiments, the technology provides a perovskite comprising a fraction of 0.1 Cs and a fraction of 0.9 FA for A and thus having formula such as $Cs_{0.1}FA_{0.9}PbX_3$. B and X may also have fractional composition as described herein.

In some embodiments, B is a heavy metal or high-Z material (e.g., lead, tin). In some embodiments, B is a fractional combination of one or more heavy metals and/or high-Z materials. For example, embodiments comprise a perovskite composition having a formula $ABB'X_3$ where the fractional composition of B ranges from 0 to 1 and the fractional composition of B' ranges concomitantly from 1 to 0, e.g., $ABX_3$, $AB_{0.9}B'_{0.1}X_3$, $AB_{0.8}B'_{0.2}X_3$, $AB_{0.7}B'_{0.3}X_3$, $AB_{0.6}B'_{0.4}X_3$, $AB_{0.5}B'_{0.5}X_3$, $AB_{0.4}B'_{0.6}X_3$, $AB_{0.3}B'_{0.7}X_3$, $AB_{0.2}B'_{0.8}X_3$, $AB_{0.1}AB'_{0.9}X_3$, or $AB'X_3$. A and X may also have fractional composition as described herein.

The technology also comprises embodiments relating to a perovskite composition having a formula $AA'BB'(XX')_3$ where the fractional composition of A ranges from 0 to 1 and the fractional composition of A' ranges concomitantly from 1 to 0, the fractional composition of B ranges from 0 to 1 and the fractional composition of B' ranges concomitantly from 1 to 0, and/or the fractional composition of X ranges from 0 to 1 and the fractional composition of X' ranges concomitantly from 1 to 0.

As described with respect to exemplary perovskite compositions herein, the technology is not limited in the elements or ions (e.g., cations or anions) that are indicated by A, B, and X in the $ABX_3$ structure. In some embodiments, A is an organic cation or an inorganic cation. In some embodiments, A is methylammonium, formamidinium, cadmium, cesium, or rubidium. In some embodiments, B is a heavy metal cation. In some embodiments, B is lead or tin. In some embodiments, X is a halide anion. In some embodiments, X is iodide, bromide, or chloride.

In some embodiments, the perovskite is provided in a single-layer perovskite composition. In some embodiments, the perovskite is provided in a dual-layer perovskite composition. In some embodiments, the technology provides a device comprising a perovskite dual-layer composition and thru-silicon-via electrodes. In some embodiments, the perovskite composition is deposited on a substrate and has a uniform thickness (e.g., a variation of thickness less than 1%).

Graphene

In some embodiments, perovskite is deposited on graphene. Graphene comprises a single layer of carbon atoms arranged in a hexagonal structure [52], [53]. Graphene comprises a continuous network of $sp^2$ hybridized carbon bonds. As a result, graphene materials have useful properties. For instance, graphene is a zero-bandgap material that absorbs light and generates charge carriers [54]-[56]. Further, graphene materials have field-effect sensitivity by which the electronic and optical properties of graphene may be tuned by applying an electric field [57], [58]. Also, graphene has an efficient mobility to silicon of more than two orders of magnitude [59]. Consequently, the efficient mobility of graphene provides efficient carrier dynamics and thus converts photons into electrical signals extremely fast [60]-[63]. Finally, the planar structure of graphene provides that graphene devices are easily integrated with conventional silicon electronics platforms [64]-[66]. Recent advances in graphene synthesis by chemical vapor deposition (CVD) have enabled graphene processing at the wafer scale. [67]

Photon-Counting Sensor

Conventional computed tomography (CT) systems use energy-integrating detectors (EID) comprising a scintillator that converts x-rays into light and a light detector that converts the light into an electrical signal. More recently, photon counting detectors (PCD) have been developed that use semiconductors to directly sense the energies of individual photons and output electrical (e.g., voltage or current) pulses proportional to photon energies. In particular, each pixel of a PCD outputs an electrical signal to an application-specific integrated circuit (ASIC) designed to provide a multi-channel analyzer (MCA), which discriminates photons based on photon energies, sorts photons into energy channels, and/or counts photons in the energy channels. Thus, the PCD quantifies photons in discrete energy channels to produce an energy spectrum. Accordingly, conventional CT scanners indirectly measure the total energy of photons deposited in a pixel during a fixed period of time using a scintillant intermediary and output a signal corresponding to an accumulated photon intensity. In contrast, photon counting computed tomography scanners directly measure individual photon energies and output an energy spectrum providing photon energy resolution. Consequently, CT-PCD provides a technology that distinguishes materials of differing density (e.g., different tissues in a body) from a singular x-ray scan. See, e.g., Willemink (2018) "Photon-counting CT: Technical Principles and Clinical Prospects" Radiology 289: 293-312, incorporated herein by reference.

Consequently, CT-PCD technologies provide advantages relative to indirect EID technologies such as dual energy CT. For instance, dual energy CT is limited to detecting photons in two energy ranges for identifying the atomic number of a material. In contrast, CT-PCD technologies detect photons in more than two energy ranges (e.g., in three or more energy channels), any of which may be near the k-edge of a high-Z material such as a contrast agent (e.g., an iodine contrast agent). Thus, multiple energy channels can be used to identify multiple types of materials within a body with a high level of specificity. Accordingly, CT-PCD provides a greater resolution imaging technology for identifying material types, e.g., in contrast imaging or other material identification. Further, CT-PCD technologies may be used with overall lower x-ray doses and thus reduces the exposure of patients to x-rays.

Conventional CT-PCD use direct conversion sensors comprising a semiconductor such as cadmium telluride (CdTe) or cadmium zinc telluride (CZT). While these materials provide a high energy resolution (e.g., a narrow full-width-half-max (FWHM) of the spectral peak) for accurate material identification in certain energy ranges, the cadmium and/or tellurium in these sensors produces a high yield of in-sensor k-edge fluorescence at approximately 25 keV to 35 keV (e.g., 27 keV and 32 keV from the Cd and Te, respectively). These k-fluorescence photons fall within an energy window (e.g., at approximately 30 keV) that is used in radiological imaging to identify tissues and other materials, e.g., to identify contrast agents present in tissue. For example, iodine contrast agents have a k-edge absorption of 33 keV and the energy window resolution is approximately 1-5 keV up to photon energies of 120 keV. Thus, in-sensor k-fluorescence photons produced in conventional CT-PCD interfere with detection of informative photons (e.g., from a contrast agent). As a consequence, CT-PCD using conventional sensor materials has inherent technological limitations for identifying materials (e.g., tissues and/or contrast agents) in radiological imaging.

In particular, k-fluorescence in PCD sensor materials reduces spectral efficiency; increases pixel pitch, which reduces spatial resolution; and increases pulse pile-up for high-count rates, which increases the radiological dose to the patient and increases scan time. Additionally, k-fluorescence in PCD sensor materials reduces quantum efficiency (QE), reduces energy resolution (ER), and reduces the specificity of identifying materials within the body, especially when the pixel pitch is less than the k-fluorescence travel path.

Accordingly, provided herein is a perovskite-based photon-counting sensor that does not emit k-fluorescence in energy channels of interest for use medical imaging. In other words, in some embodiments, the technology provides a photon-counting sensor comprising a perovskite material that minimizes and/or eliminates in-sensor k-fluorescence in energy channels used for medical imaging (e.g., between approximately 20 to 140 keV and/or in regions such as at approximately 30 keV used to detect contrast agents).

In some embodiments, the technology provides a photon-counting sensor comprising a perovskite composition comprising $FAPbBr_3$. In some embodiments, the technology provides a photon-counting sensor comprising a perovskite composition comprising a fractional composition of FA and Cs. In some embodiments, the technology provides a photon-counting sensor comprising a perovskite composition comprising a fractional composition of $Br_3$, $I_3$, and/or $Cl_3$. In some embodiments, the technology provides a photon-counting sensor comprising a perovskite composition comprising a fractional composition of FA and Cs and a fractional composition of $Br_3$, $I_3$, and/or $Cl_3$. For example, in some embodiments, the technology provides a photon-counting sensor comprising a perovskite composition comprising a fractional composition of FA ranging from 0 to 1 and a fractional composition of Cs ranging concomitantly from 1 to 0, e.g., $FAPbBr_3$, $FA_{0.9}Cs_{0.1}PbBr_3$, $FA_{0.8}Cs_{0.2}PbBr_3$, $FA_{0.7}Cs_{0.3}PbBr_3$, $FA_{0.6}Cs_{0.4}PbBr_3$, $FA_{0.5}Cs_{0.5}PbBr_3$, $FA_{0.4}Cs_{0.6}PbBr_3$, $FA_{0.3}Cs_{0.7}PbBr_3$, $FA_{0.2}Cs_{0.8}PbBr_3$, $FA_{0.1}Cs_{0.9}PbBr_3$, or $CsPbBr_3$. In some embodiments, the technology provides a photon-counting sensor comprising a perovskite composition comprising a fractional composition of FA ranging from 0 to 1 and a fractional composition of Cs ranging concomitantly from 1 to 0, e.g., $FAPbX_3$, $FA_{0.9}Cs_{0.1}PbX_3$, $FA_{0.8}Cs_{0.2}PbX_3$, $FA_{0.7}Cs_{0.3}PbX_3$, $FA_{0.6}Cs_{0.4}PbX_3$, $FA_{0.5}Cs_{0.5}PbX_3$, $FA_{0.4}Cs_{0.6}PbX_3$, $FA_{0.3}Cs_{0.7}PbX_3$, $FA_{0.2}Cs_{0.8}PbX_3$, $FA_{0.1}Cs_{0.9}PbX_3$, or $CsPbX_3$, where X is a fractional composition of $Br_3$, $I_3$, and/or $Cl_3$ in which the fractional composition of each of $Br_3$, $I_3$, and/or $Cl_3$ ranges from 0 to 1 and the sum of the fractional compositions of $Br_3$, $I_3$, and $Cl_3$ equals 1.

In some embodiments, a photon-counting sensor comprising a perovskite composition comprising $FAPbBr_3$; a fractional composition of FA and Cs; a fractional composition of $Br_3$, $I_3$, and/or $Cl_3$; or a fractional composition of FA and Cs and a fractional composition of $Br_3$, $I_3$, and/or $Cl_3$ as described herein finds use in a PCD for radiological imaging using an iodine contrast agent and a spectrum of x-ray energies up to approximately 140 keV or a virtual monoenergetic energy image at approximately 60 keV.

In some embodiments, a photon-counting sensor comprising a perovskite composition comprising $FAPbBr_3$; a fractional composition of FA and Cs; a fractional composition of $Br_3$, $I_3$, and/or $Cl_3$; or a fractional composition of FA and Cs and a fractional composition of $Br_3$, $I_3$, and/or $Cl_3$ as described herein comprises a single layer of perovskite (e.g., a single-layer sensor).

In some embodiments, the technology provided herein is an x-ray PCD that provides improved spectral efficiency and thus provides superior material identification and/or discrimination. During the development of embodiments of the technology described herein, perovskite compositions were identified that minimize and/or eliminate in-sensor k-fluorescence in regions of an x-ray spectrum that are informative for medical radiology and diagnosis. For example, in some embodiments, perovskite compositions were identified that shift in-sensor k-fluorescence to regions of an x-ray spectrum that are not informative for radiology and diagnosis. Thus, the technology provides a PCD that does not distort spectral information of importance by k-fluorescence photons.

Further, in contrast to conventional photon-counting sensor materials, the perovskite-based photon counting sensor described herein may be used to produce detectors with decreased pixel pitches relative to conventional PCD technologies for which lower limits on pixel pitch exist due to k-fluorescence interference within the sensor materials. Accordingly, embodiments of technology comprise a perovskite-based photon-counting sensor with a pixel pitch that is smaller relative to conventional PCD sensor technologies and that thus improves the spectral efficiency and/or the energy resolution of the perovskite-based photon-counting sensor relative to conventional PCD sensor technologies.

In some embodiments, the technology provides a photon-counting sensor comprising a perovskite composition. In some embodiments, the perovskite composition is deposited in a single layer on a surface. In some embodiments, a number of perovskite compositions is deposited in a plurality of layers (e.g., 2 layers, 3 layers, 4 layers, 5 layers, or more than 5 layers) on a surface. Accordingly, in some embodiments, the technology provides a photon-counting sensor comprising a surface and a layer of a perovskite composition deposited on the surface. In some embodiments, the technology provides a photon-counting sensor comprising a surface, a first layer of a perovskite composition deposited on the surface, and a second layer of a perovskite composition deposited on the first layer of the perovskite composition. In embodiments comprising a plurality of layers comprising a perovskite composition, each layer may comprise a perovskite composition that is the same or that is different that a composition of one or more different layer(s).

In some embodiments, the technology provides a photon-counting sensor comprising electrodes and a perovskite composition that is compositionally tuned to minimize and/or eliminate k-fluorescence. In some embodiments, the electrodes are thru-silicon-via (TSV) electrodes. In some embodiments, the TSV electrode is an anode; in some embodiments, the TSV electrode is a cathode. Accordingly, a TSV electrode that may be an anode or a cathode are referred to using the term "TSV anode/cathode". It is to be understood that an opposing electrode (e.g., a common electrode) is an anode when the sensing (e.g., TSV) electrode is a cathode and is a cathode when the sensing (e.g., TSV) electrode is an anode. In some embodiments, one TSV anode/cathode is designated per pixel in a single-layer perovskite sensor and a common anode/cathode is placed on the opposite side of the sensor.

Figure 1:
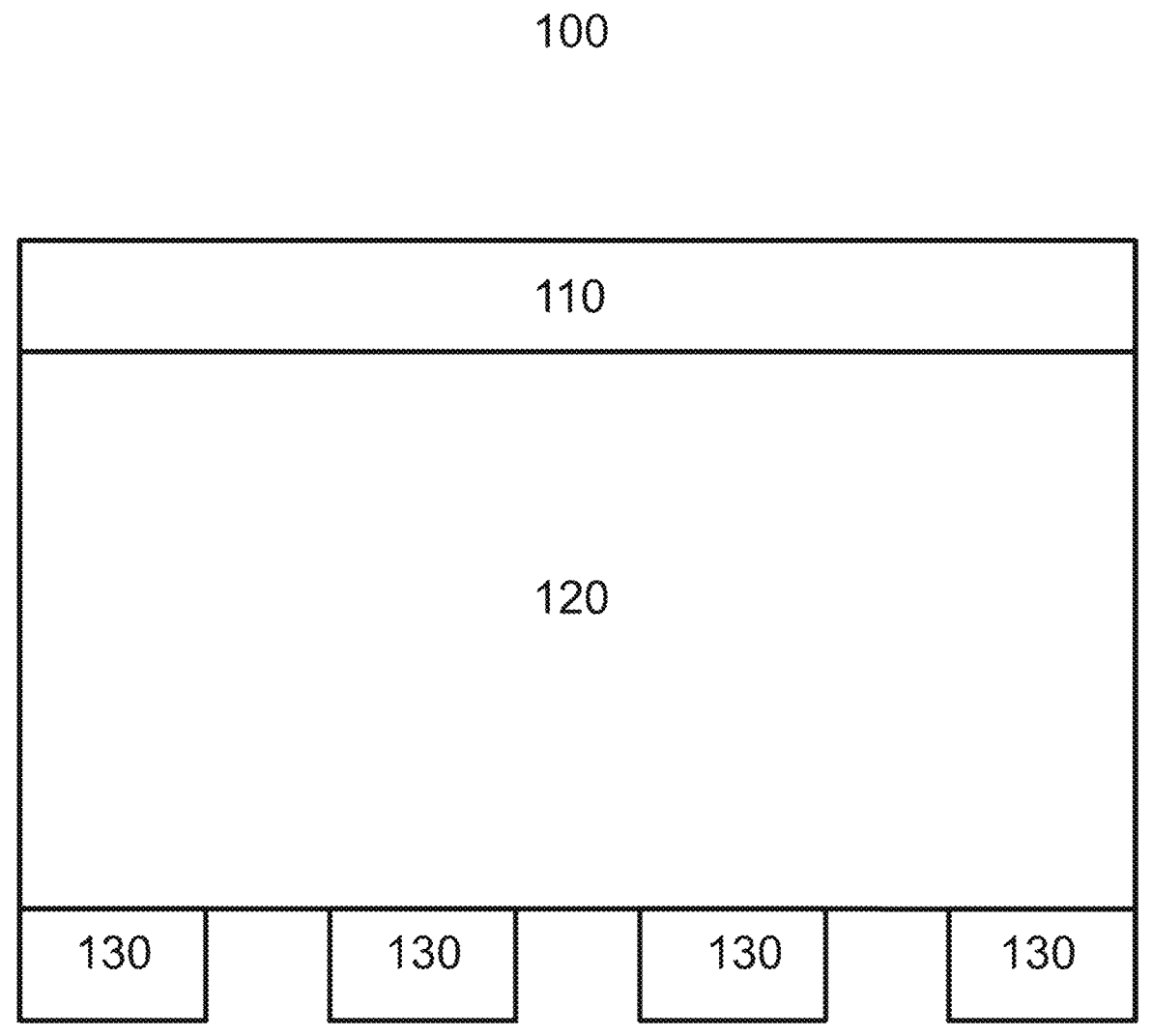

For example, in some embodiments, e.g., as shown in FIG. 1, the technology provides a single-layer perovskite sensor 100 that is compositionally tuned to minimize and/or eliminate k-fluorescence. As shown in FIG. 1, embodiments of a single-layer perovskite sensor 100 comprise a common anode/cathode 110, a perovskite composition 120 that is compositionally tuned to minimize and/or eliminate k-fluorescence, and a number of pixel anodes/cathodes 130. In some embodiments, e.g., as shown in FIG. 2, the technology provides a single-layer perovskite sensor 200 comprising through-silicon-via (TSV) electrodes 230 for each pixel of a readout integrated circuit (ROIC) (e.g., a high-speed counting ASIC (e.g., a Medipix3RX read-out board) or a multi-channel analyzer (MCA) ASIC), a common anode/cathode 210, and a perovskite composition 220 that is compositionally tuned to minimize and/or eliminate k-fluorescence.

In some embodiments, the technology provides a dual-layer perovskite sensor comprising two or more perovskite compositions that minimize and/or eliminate the in-sensor k-fluorescence within energy channels of relevance for medical imaging (e.g., energy channels useful to identify materials (e.g., tissues, contrast agents) of interest within the body using medical imaging). For example, in some embodiments, a dual-layer perovskite sensor comprises a first (e.g., top) perovskite layer (e.g., having a thickness of 600 to 1700 μm (e.g., 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, or 1700 μm) that absorbs x-rays from 1 to 60 keV (e.g., 1, 5, 10, 15, 20, 25, 30, 35, 40, 45, 50, 55, or 60 keV) that are used to image materials within the body having a low $Z_{eff}$ (e.g., $Z_{eff}$ of 2 to 20 (e.g., 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, 16.0, 16.1, 16.2, 16.3, 16.4, 16.5, 16.6, 16.7, 16.8, 16.9, 17.0, 17.1, 17.2, 17.3, 17.4, 17.5, 17.6, 17.7, 17.8, 17.9, 18.0, 18.1, 18.2, 18.3, 18.4, 18.5, 18.6, 18.7, 18.8, 18.9, 19.0, 19.1, 19.2, 19.3, 19.4, 19.5, 19.6, 19.7, 19.8, 19.9, or 20.0)) and a second (e.g., bottom) perovskite layer (e.g., having a thickness of 2 to 4 mm (e.g., 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 mm)) that absorbs x-rays from 60 to 120 keV (e.g., 60, 65, 70, 75, 80, 85, 90, 95, 100, 105, 110, 115, or 120 keV) that are used to image materials having a high $Z_{eff}$, such as a contrast agent (e.g., encapsulated gold (Au) nanoparticles with a k-edge of approximately 81 keV)) used to improve specificity for image reconstruction. In some embodiments, a dual-layer perovskite sensor comprising two or more perovskite compositions that minimize and/or eliminate the in-sensor k-fluorescence within energy channels of relevance for medical imaging is used for k-edge imaging techniques and non-k-edge imaging techniques, such as photoelectric and/or Compton scatter slope-of-the-line techniques used to identify materials having a low $Z_{eff}$ and/or to identify materials having a high $Z_{eff}$.

In some embodiments, the dual-layer perovskite sensor comprises electrodes, e.g., thru-silicon-via (TSV) anode(s)/cathode(s). In some embodiments, each pixel of the sensor comprises a pair of TSV anode(s)/cathode(s) dedicated to the pixel. In particular, a first TSV anode/cathode measures the electrical signal generated from the bottom perovskite layer and does not protrude into the top perovskite layer (e.g., the first TSV anode/cathode is electrically isolated from the top perovskite layer); and the second TSV anode/cathode measures the electrical signal generated from the top perovskite layer and is electrically insulated from the bottom perovskite layer (e.g., the second TSV anode/cathode is electrically isolated from the bottom perovskite layer). Accordingly, the dual-layer perovskite sensor provides enhanced discrimination of photon counts in the designated energy channels of interest. In some embodiments, the two electrical signals produced from the first and second TSV electrodes are measured in coincidence counting, and the signals are reconstructed and/or combined to provide a completed image. Specificity is provided by designating energy channels within each of the dual layers of the sensor to count photons providing information for relevant materials. The opposing anode/cathode is common to all pixels and is in contact with the sensor and faces the opposite side of the TSV anode(s)/cathode(s).

Figure 3:
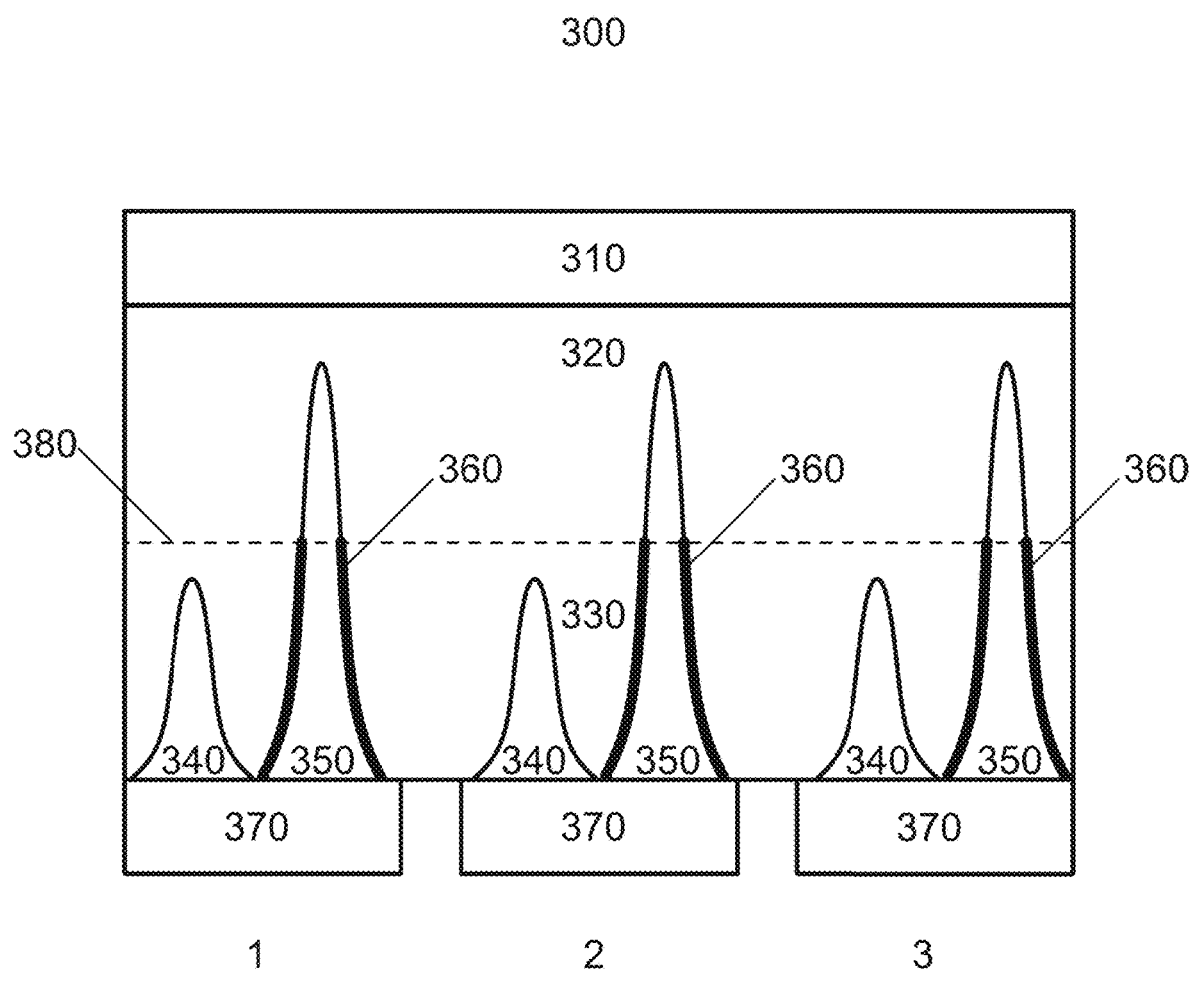
FIG. 3 is a schematic drawing of a dual-layer perovskite sensor comprising two TSV electrodes for each of three pixels (1, 2, 3) of a readout integrated circuit (ROIC) and two layers of perovskite that are compositionally tuned to minimize and/or eliminate k-fluorescence.

For example, e.g., as shown in FIG. 3, embodiments provide a dual-layer perovskite sensor 300 comprising two TSV electrodes 340, 350 for each pixel 1, 2, 3 of a readout integrated circuit (ROIC) (e.g., a high-speed counting ASIC (e.g., a Medipix3RX read-out board) or a multi-channel analyzer (MCA) ASIC) and two layers of perovskite 320, 330 that are compositionally tuned to minimize and/or eliminate k-fluorescence. As shown in FIG. 3, embodiments of the dual-layer perovskite sensor 300 comprise a common anode/cathode 310, a first (e.g., top) perovskite layer 320, and a second (e.g., bottom) perovskite layer 330. The first perovskite layer 320 and the second perovskite layer 330 are separated by a perovskite layer interface 380. The dual-layer perovskite sensor 300 further comprises a first TSV anode/cathode 340 for detecting signals produced by the bottom perovskite layer 330 and a second TSV anode/cathode 350 for detecting signals produced by the top perovskite layer 320. The first TSV anode/cathode 340 does not extend into and/or contact the top perovskite layer 320 and thus the first TSV anode/cathode 340 is electrically isolated from the top perovskite layer 320. The second TSV anode/cathode 350 comprises an electrical shielding 360 and thus the second TSV anode/cathode 350 is electrically isolated from the bottom perovskite layer 330 and the second TSV anode/cathode 350 does not electrically communicate the bottom perovskite layer 330. Further, as shown in FIG. 3, embodiments of the dual-layer perovskite sensor 300 comprise a common pixel read-out circuit (e.g., comprising a readout integrated circuit (ROIC) (e.g., a high-speed counting ASIC (e.g., a Medipix3RX read-out board) or a multi-channel analyzer (MCA) ASIC)) for each TSV pair (e.g., comprising each pair of the first TSV anode/cathode 340 for detecting signals produced by the bottom perovskite layer 330 and the second TSV anode/cathode 350 for detecting signals produced by the top perovskite layer 320) dedicated to each pixel 1, 2, 3.

Embodiments of the technology, e.g., as shown in FIG. 3, provide a technology for discriminating and/or identifying materials using x-rays. For example, the dual-layer perovskite sensor shown in FIG. 3 comprises a top perovskite layer 320 that absorbs most of the x-ray photon energies (e.g., approximately 60 keV) that are used to identify soft tissue and bone in an image while allowing higher energy photons (e.g., approximately 60 to 120 keV) to pass through to the bottom layer. The dual-layer perovskite sensor shown in FIG. 3 comprises a bottom perovskite layer 330 that absorbs x-ray photons having an energy of less than approximately 120 keV and thus provides a signal from detecting photons having an energy of approximately 60 to 120 keV because photons having an energy of 60 keV or less are absorbed by the top layer.

The top perovskite layer 320 is in electrical communication with a dedicated electrode 350 and the bottom perovskite layer 330 is in electrical communication with a dedicated electrode 340. A common multi-channel-analyzer (MCA) is provided for each electrode pair connected to each pixel 1, 2, 3. In some embodiments, the MCA is tunable to identify, select, and quantify photons in relevant energy channels, e.g., an energy channel for identifying photons in the upper (e.g., 60 to 120 keV) energy range to identify materials having a high $Z_{eff}$ and an energy channel for identifying photons in the lower energy range (e.g., less than 60 keV) to identify materials having a low $Z_{eff}$. Embodiments provide that data collected from the upper (e.g., 60 to 120 keV) energy range and the lower energy range are merged and/or combined to produce a complete image.

Figure 4:
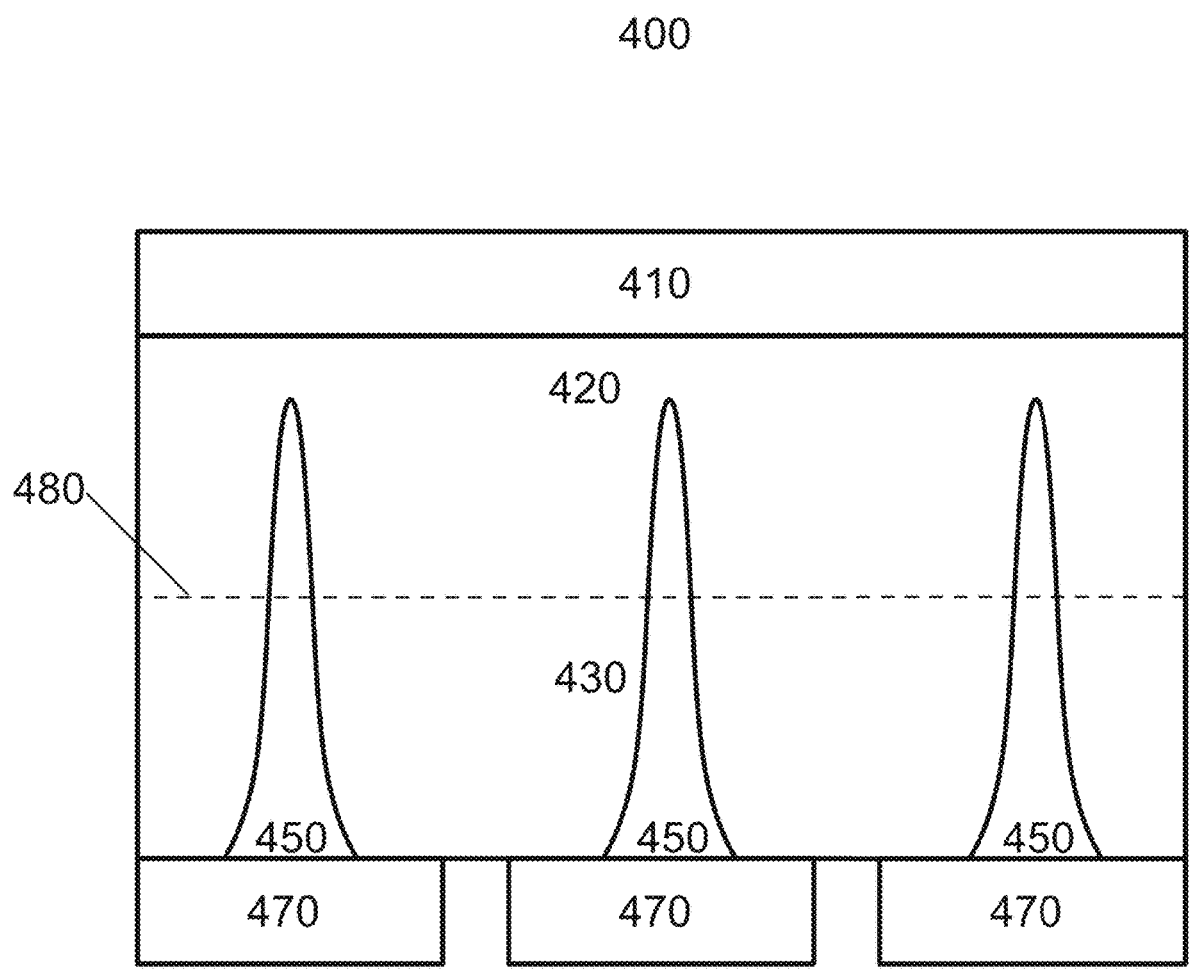
FIG. 4 is a schematic drawing showing a dual-layer perovskite sensor comprising a TSV electrode for each pixel of a readout integrated circuit (ROIC) and two layers of perovskite that are compositionally tuned to minimize and/or eliminate k-fluorescence.

In some embodiments, e.g., as shown in FIG. 4, the technology provides a dual-layer perovskite sensor 400 comprising a TSV electrode 450 for each pixel of a readout integrated circuit (ROIC) 470 (e.g., a high-speed counting ASIC (e.g., a Medipix3RX read-out board) or a multi-channel analyzer (MCA) ASIC) and two layers of perovskite 420, 430 that are compositionally tuned to minimize and/or eliminate k-fluorescence.

In some embodiments, a single-layer perovskite sensor that is compositionally tuned to minimize and/or eliminate k-fluorescence provides enhanced specificity for virtual-mono-energetic imaging used in a CT x-ray spectrum. In some embodiments, a dual-layer perovskite sensor that is compositionally tuned to minimize and/or eliminate k-fluorescence provides enhanced specificity for virtual-mono-energetic imaging used in a CT x-ray spectrum While FIGS. 1 to 4 show perovskite sensors comprising 1 to 4 pixels for convenience, the technology is not limited to embodiments of a perovskite sensor comprising 1, 2, 3, or 4 pixels. In some embodiments, the technology provides perovskite sensors comprising at least 10; at least 100; at least 1000; at least 10,000; at least 100,000; at least 1,000,000; at least 10,000,000; or at least 100,000,000 pixels. Further embodiments provide that the pixels may be arranged in a linear array or a two-dimensional array comprising rows and columns or in a hexagonal or other arrangement.

In some embodiments, the technology provides a photon-counting sensor comprising conventional electrodes and a perovskite composition that is compositionally tuned to minimize and/or eliminate k-fluorescence. That is, in some embodiments, conventional electrodes may be substituted for TSV electrodes. In some embodiments, the technology provides a dual-layer photon-counting sensor comprising a perovskite composition that is compositionally tuned to minimize and/or eliminate k-fluorescence and conventional electrodes that are, e.g., reverse biased coplanar pixelated electrodes (e.g., 2-terminal current matching electrodes or 4-terminal electrodes).

In some embodiments, the technology provides a photon-counting sensor comprising a transistor and a perovskite composition that is compositionally tuned to minimize and/or eliminate k-fluorescence. For example, in some embodiments, a photon-counting sensor comprising a perovskite composition that is compositionally tuned to minimize and/or eliminate k-fluorescence comprises a gate dielectric placed underneath the perovskite sensor layer and further comprises a substrate adjacent to the gate dielectric. In some embodiments, the perovskite sensor material is shaped and/or patterned, the gate dielectric is shaped and/or patterned, and/or the source and/or drain electrodes of the transistor are shaped and/or patterned. In some embodiments, a third electrode is in contact with the substrate to modulate the gain signal.

In some embodiments, the technology provides a photon-counting sensor comprising a perovskite composition that is compositionally tuned to minimize and/or eliminate k-fluorescence and a photoconductor, diode, a reverse bias diode, a resistor, a 2-point dual layer signal collection, a 4-point dual layer signal connection, a pixelated electrode, an inter-digitated electrode, and/or a thru-silicon-via electrode. In some embodiments, the photon-counting sensor comprises guard rings on the side of the cathode and/or anode.

In some embodiments, the technology comprises a photon-counting sensor comprising a perovskite composition that is patterned with techniques and/or materials such as parylene and/or orthogonal photoresist, e.g., permanent parylene structures that lay in place on the perovskite sensor layer with patterned openings to allow metal deposition for direct contact onto the perovskite sensor.

In some embodiments, the technology comprises a photon-counting sensor comprising an electrode that is patterned with techniques and/or materials such as parylene and/or orthogonal photoresist, e.g., permanent parylene structures that lay in place on the perovskite sensor layer with patterned openings to allow metal deposition for direct contact onto the perovskite sensor. In some embodiments comprising use of parylene layers, photolithography is used to deposit metal layers on a substrate.

In some embodiments, the technology comprises a photon-counting sensor comprising a perovskite composition that is produced using growth techniques such as Bridgman growth, solution processed inverse temperature method, spin casting, hot casting, printing, doctor blade methods, tape casting, an inverse temperature method, and the like. In some embodiments, Bridgman growth is used to provide high purity single crystal perovskite sensors. In some embodiments, growing a perovskite crystal directly on the graphene surface of the graphene field effect transistor comprises using a doctor blade method or tape casting. In some embodiments, growing a perovskite crystal directly on the graphene surface of the graphene field effect transistor comprises using an inverse temperature method. In some embodiments, an inorganic constituent is added to raise the in-phase temperature for crystal growth using Bridgman growth of perovskite crystals. In some embodiments, the A cation is entirely inorganic.

In some embodiments, the technology comprises a photon-counting sensor comprising a perovskite composition that is formed directly onto graphene. In some embodiments, the technology comprises a photon-counting sensor comprising a perovskite composition that is formed directly onto graphene using printing, spin casting, and/or hot casting the perovskite directly onto the graphene, e.g., using a one-step or in a 2-step process. In some embodiments, the graphene acts as a transparent electrode.

In some embodiments, the technology comprises a photon-counting sensor comprising a perovskite composition that is patterned directly onto a pre-patterned graphene using a technique for shaping the perovskite to provide pixels on the graphene. In some embodiments, the technique for shaping the perovskite to provide pixels on the graphene comprises printing, spin casting, and/or hot casting the perovskite directly onto the graphene, e.g., using a one-step or in a 2-step process. In some embodiments, the graphene acts as a transparent electrode.

In some embodiments, the perovskite layer provided on a graphene substrate is unbiased. In some embodiments, electrical signals (e.g., currents) are provided by the perovskite material charge carrier diffusion length (mu-tau product) and work function differences between the graphene and perovskite materials that drive electron movement.

In some embodiments, graphene is transferred to a perovskite composition using dry transfer techniques.

In some embodiments, a dual-layer photon-counting sensor comprising a perovskite composition that is compositionally tuned to minimize and/or eliminate k-fluorescence is formed from coupling two different perovskite materials.

In some embodiments, a dual-layer photon-counting sensor comprising a perovskite composition that is compositionally tuned to minimize and/or eliminate k-fluorescence is formed from growing two different perovskite materials as a singular material to maximize electronic transfer at the surface interface.

In some embodiments, a dual-layer photon-counting sensor comprising a perovskite composition that is compositionally tuned to minimize and/or eliminate k-fluorescence comprises two different perovskite materials and an electrically insulating material is provided between the two different perovskite materials to control electron cloud charge sharing at the interface between the two different perovskite materials.

Embodiments of the technology are provided that combine variations and components as described herein. For example, in some embodiments, a single-layer perovskite sensor comprises reverse biased co-planar pixelated electrodes. In some embodiments, reverse biased co-planar pixelated electrodes are suitable for low temperature bump bond processing. In some embodiments, a dual-layer perovskite sensor comprises thru-silicon-via (TSV) electrodes. In some embodiments, the TSV electrodes are electrically connected to an ASIC (e.g., an ASIC designed to provide a multi-spectral MCA).

In some embodiments, the perovskite sensor that is compositionally tuned to minimize and/or eliminate k-fluorescence finds use in photon counting multi-spectral x-ray imaging, e.g., for use in computed tomography.

Perovskite-Graphene Sensor

Direct conversion sensors (e.g., comprising a semiconductor such as amorphous selenium), provide more charge carriers per photon energy deposited for a given sensor thickness relative to indirect conversion sensors (e.g., comprising a scintillator such as cesium iodide). Accordingly, direct conversion sensors provide greater sensitivity than indirect conversion sensors at a given spatial resolution [1], [2]. However, conventional direct conversion sensors comprising amorphous selenium (a-Se) lack the sensitivity to distinguish between healthy and unhealthy tissue with high accuracy, in particular for imaging methods using a low exposure per frame (e.g., tomosynthesis [3]-[12]).

Accordingly, the technology described herein relates to a perovskite-graphene direct conversion sensor that provides increased sensitivity and image quality relative to conventional direct conversion sensors (e.g., conventional direct conversion sensors comprising a-Se). As described herein, embodiments of the perovskite composition are designed and synthesized to minimize and/or eliminate in-sensor K-edge fluorescence and/or to move K-edge fluorescence to energies outside the informative energy channels of interest for medical imaging, e.g., energy channels used to detect imaging contrast agents, ligand assisted encapsulated heavy metal nanoparticles, or human tissue types of interest in x-ray imaging (e.g., 20-45 keV). Thus, in some embodiments, the technology described herein relates to a perovskite-graphene direct conversion sensor that is fluorescence free between 20-45 keV.

In some embodiments, the perovskite-graphene sensor comprises multiple pixels and is thus a multi-pixel perovskite-graphene sensor. In some embodiments, the perovskite-graphene sensor is an energy integrating detector. As discussed herein, perovskite materials provide high stopping power of X-rays, efficient charge transfer properties, and ease of material synthesis. Further, graphene provides efficient carrier mobility, efficient photoconductive gain, and easy integration with conventional electronic platforms. In some embodiments, the technology provides a low bias sensor that can be produced at a lower cost than conventional sensors.

Figure 8A:
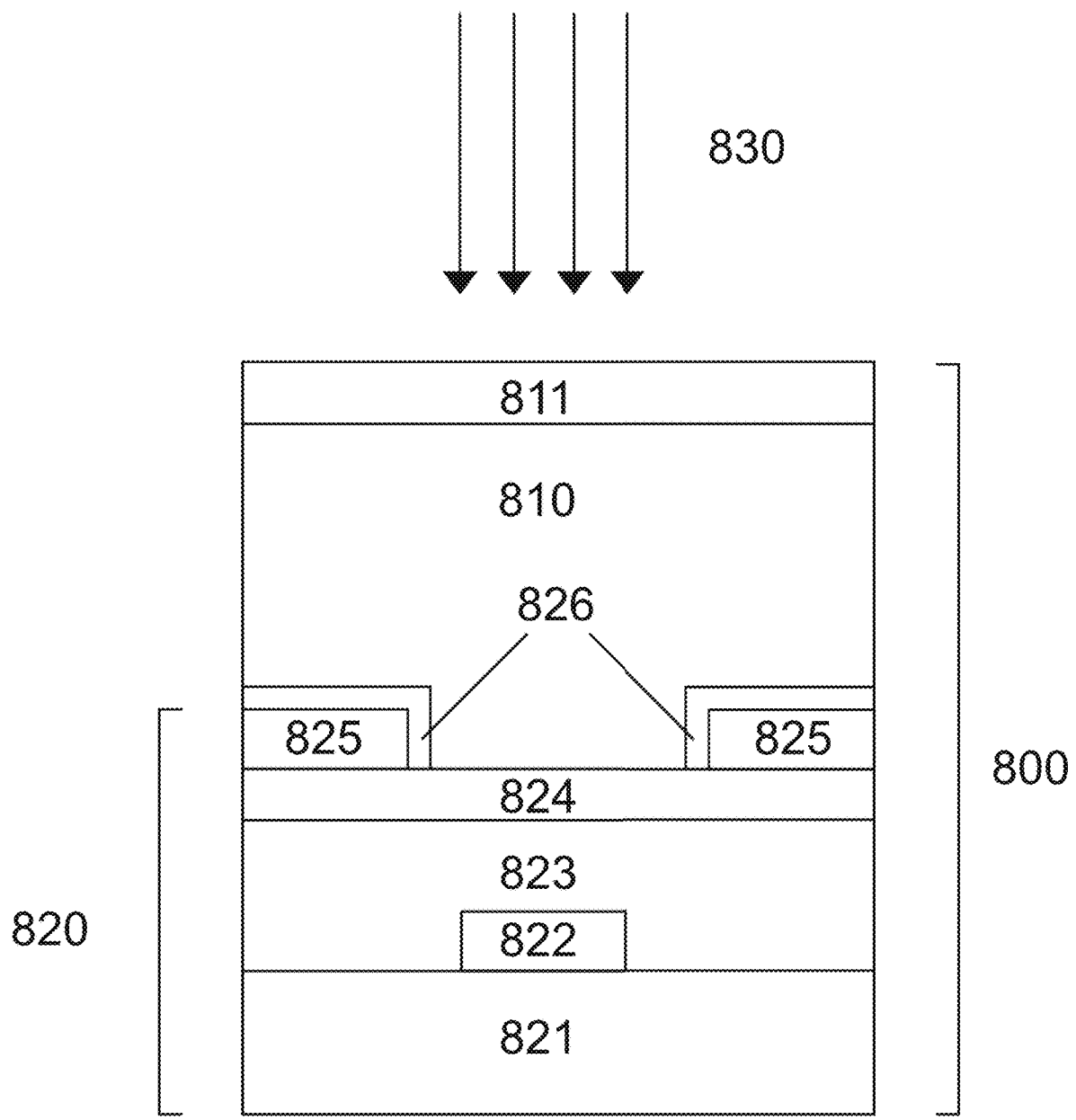
FIG. 8A is a schematic drawing showing a cross-sectional view of a perovskite-graphene pixel.

In some embodiments, the technology provides a solution-processed perovskite composition grown directly on a conductive graphene lattice. For example, e.g., as shown in FIG. 8A, embodiments of the technology provide a perovskite-graphene direct conversion sensor 800 comprising a perovskite composition 810 layered on a graphene field effect transistor (GFET) 820. In some embodiments, the perovskite composition 810 is fluorescence-free in energy channels used for medical imaging (e.g., 20-45 keV). In some embodiments, e.g., as shown in FIG. 8A, the GFET 820 comprises a substrate 821 (e.g., a substrate comprising a silicon wafer covered with a layer of $SiO_2$ (e.g., a 90-nm thick layer of $SiO_2$)); a back-gate 822 (e.g., an Au or Cr/Au back-gate); a gate dielectric 823 (e.g., comprising a thin film of $Al_2O_3$); a graphene layer 824; and source-drain edge contacts 825 (e.g., comprising Cr/Au). In some embodiments, the GFET 820 further comprises an encapsulant 826 (e.g., $Al_2O_3$) that encapsulates the source-drain edge contacts 825. In some embodiments, the encapsulant 826 (e.g., $Al_2O_3$) is applied to the source-drain edge contacts 825 using photomask photolithography. Accordingly, embodiments provide that the electrodes (source-drain edge contacts 825) are encapsulated so that the graphene layer 824 provides the only electrical connection with the perovskite composition 810. Thus, the metal of the electrodes does not diffuse into the perovskite material and performance of the sensor is maximized over time. In some embodiments, the graphene layer 824 comprises channels. Portions of the gate dielectric 823 are removed (e.g., by optical lithography and/or wet etching) to expose the contacts of the back-gate 822. In some embodiments, the graphene is patterned, e.g., to provide channels in the graphene layer.

In some embodiments, the GFET 820 further comprises an encapsulant 826 (e.g., $Al_2O_3$) that encapsulates the source-drain edge contacts 825. In some embodiments, the encapsulant 826 (e.g., $Al_2O_3$) is applied to the source-drain edge contacts 825 using photomask photolithography. Accordingly, embodiments provide that the electrodes (source-drain edge contacts 825) are encapsulated so that the graphene layer 824 provides the only electrical connection with the perovskite composition 810. Thus, the metal of the electrodes does not diffuse into the perovskite material and performance of the sensor is maximized over time. In some embodiments, the graphene layer 824 comprises channels. Portions of the gate dielectric 823 are removed (e.g., by optical lithography and/or wet etching) to expose the contacts of the back-gate 822. In some embodiments, the graphene is patterned, e.g., to provide channels in the graphene layer.

Figure 8B:
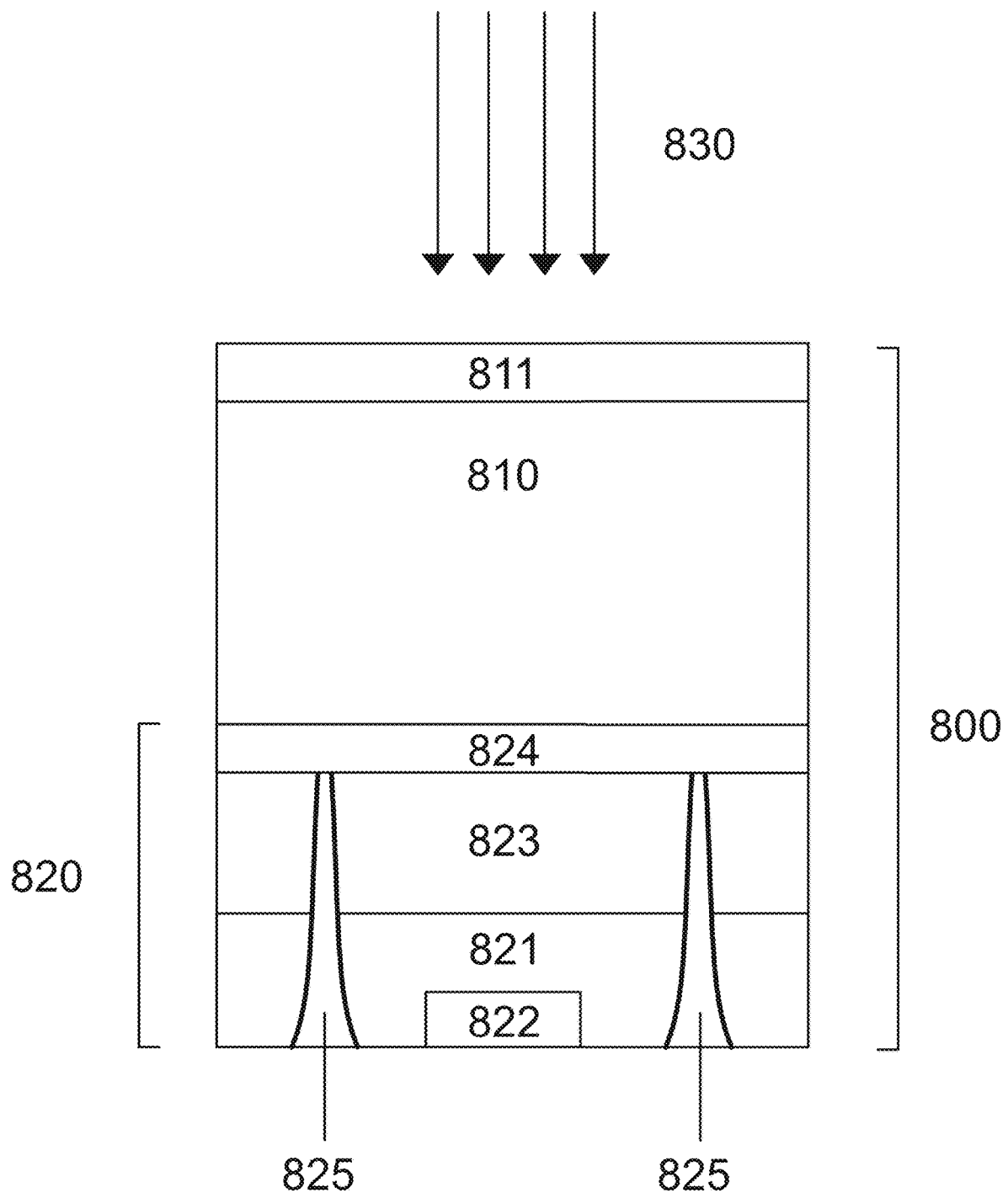
FIG. 8B is a schematic drawing showing a cross-sectional view of a perovskite-graphene pixel.

In some embodiments, e.g., as shown in FIG. 8B, embodiments of the technology provide a perovskite-graphene direct conversion sensor 800 comprising a perovskite composition 810 layered on a graphene field effect transistor (GFET) 820. In some embodiments, the perovskite composition 810 is fluorescence-free in energy channels used for medical imaging (e.g., 20-45 keV). In some embodiments, e.g., as shown in FIG. 8B, the GFET 820 comprises a substrate 821 (e.g., a substrate comprising a silicon wafer); a back-gate 822 (e.g., an Au or Cr/Au back-gate); a gate dielectric 823 (e.g., comprising a thin film of $SiO_2$ or $Al_2O_3$); a graphene layer 824; and a through-silicon-via electrode 825. In some embodiments, the through-silicon-via electrode 825 is encapsulated to electrically isolate it from the gate dielectric 823 and/or from the substrate 821. In some embodiments, the through-silicon-via electrode 825 is in electrical contact with a readout integrated circuit (ROIC). Accordingly, embodiments provide that a signal is produced at the bottom of the substrate, which is electrically connected to a ROIC, a PCB, and a chip carrier or FPGA. In some embodiments, e.g., as shown in FIG. 8B, the substrate 821 and gate dielectric 823 are provided by a ROIC (e.g., an ROIC comprises the substrate 821 and the gate dielectric 823) comprising appropriate wire tracing and peripheral electronics. Embodiments provide that the silicon wafer surface is polished and the TSV electrodes are flush with the silicon surface, the graphene is transferred onto the silicon for patterning, and the perovskite is deposited on the graphene. Accordingly, the signal is provided (e.g., pulled) through the silicon substrate. Further, in some embodiments, the bottom of the perovskite-graphene direct conversion sensor 800 is attached to a ROIC. For example, in some embodiments, a ROIC is bump-bonded (e.g., using low temperature bump bonding) to the bottom of the perovskite-graphene direct conversion sensor 800. In some embodiments, the perovskite-graphene direct conversion sensor 800 comprises a wire bonded from the side of the multiplexed pixel contact pads and the signal is passed through in-series storage capacitors for each pixel row.

Further, the perovskite-graphene direct conversion sensor 800 comprises a perovskite composition 810 deposited directly on the GFET 820. In some embodiments, e.g., as shown in FIG. 8A and FIG. 8B, a protective layer 811 (e.g., comprising $Al_2O_3$ or a polymer (e.g., polymethyl methacrylate)) is provided over the perovskite composition 810.

In some embodiments, the perovskite 810 comprises $MAPbBr_3$. In some embodiments, the perovskite comprises $FAPbBr_3$. In some embodiments, the perovskite is a perovskite composition described herein. In some embodiments, the perovskite 810 is grown as a single crystal upon the graphene surface of the GFET 820. In some embodiments, the perovskite 810 is grown as a single crystal upon the graphene surface of the GFET 820 using a hot-casting technology as described in U.S. Pat. No. 10,770,239, which is incorporated herein by reference. In some embodiments, the perovskite 810 is a polycrystalline perovskite film deposited on the graphene surface of the GFET 820 using spin coating, doctor blade coating, tape casting, or an inverse temperature method. In some embodiments, the perovskite has a thickness of 5 to 50 µm (e.g., 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0 µm). In some embodiments, the perovskite has a thickness of 5 to 50 µm (e.g., 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or 50.0 µm) with a variation in the thickness of the perovskite of less than 10% (e.g., less than 0.5 to 5 µm variation in thickness (e.g., less than 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 µm variation in the thickness). In some embodiments, a patterning process is used to isolate the perovskite over each graphene pixel, e.g., to reduce charge sharing effects. Further, in some embodiments, a patterning process is used to expose the conductive pads (e.g., source, drain, and gate) of the GFET for each pixel to provide electrical contacts.

Thus, each perovskite-graphene pixel (e.g., sensor) comprises a pair of source/drain electrodes for applied bias and charge collection and a third electrode for independent modulation of each pixel (e.g., sensor). This technology thus provides a programmable gain and a uniform pixel response.

In some embodiments, the electrical contacts are structured for wire-bonding to a chip carrier. In use, the perovskite-graphene direct conversion sensor is configured to detect x-rays 830 incident upon the perovskite composition 810. See FIG. 8A and FIG. 8B.

Previously, pixelating perovskite materials was challenging due to compatibility issues with the solvents used in the photolithography process [14]-[36]. The photolithography process is an important step in the preparation of conventional sensors that creates contact pads from the sensor material to a readout integrated circuit (ROIC).

However, during the development of the technology described, it was surprisingly discovered that the graphene surface is wettable by the perovskite composition. Thus, it was unexpected that depositing perovskite onto a graphene surface (e.g., by growing perovskite crystals directly on the graphene) would result in an interface between the perovskite and graphene that maximizes the efficiency of electron transfer between the perovskite and graphene, thus minimizing and/or eliminating scattering at the interface and minimizing and/or eliminating signal loss across the interface. Further, the technology provided herein does not require forming contact pads using a photolithography process because growing the perovskite directly on the pre-patterned graphene substrate provides both fine feature pixels and the electrical pathway in a 1-step process. Accordingly, the perovskite-graphene direct conversion sensors described herein provide advantages relative to conventional technologies, e.g., the perovskite-graphene direct conversion sensors described herein minimize and/or eliminate charge sharing among pixels; the perovskite-graphene direct conversion sensors described herein have an increased detector efficiency relative to conventional sensors; the perovskite-graphene direct conversion sensors described herein have an increased spatial resolution relative to conventional sensors; and the perovskite-graphene direct conversion sensors described herein have increased count rates relative to conventional sensors due to the "small-pixel-effect", which reduces patient scan time.

In addition, embodiments of the technology comprise an unbiased perovskite sensor. Accordingly, sensor performance is not impeded by dark currents. In contrast to technologies that apply a voltage to perovskite to move electrons, the present technology provides an unbiased perovskite-graphene sensor in which the long charge carrier diffusion length of perovskite [37] and the work function differential between the perovskite and graphene at the perovskite-graphene interface generates an internal field that pulls separated charge carriers (e.g., electrons and/or holes) into the graphene channel and produces a large photo-gain of the signal [38]-[41]. Thus, the internal photo-gain due to high mobility, low phonon scattering, and long charge carrier lifetime in the graphene film [42] provides high x-ray signal amplification and thus high x-ray sensitivity. As a consequence, the absorption of one x-ray photon in the perovskite results in multiple charge carriers contributing to the drain current response [43]. For example, in some embodiments, the perovskite-graphene sensor provides a sensitivity that is at least 10×, at least 100×, at least 1000×, at least 10,000×, or at least 100,000× more sensitive than conventional direct conversion energy integrating sensors.

Figure 9:
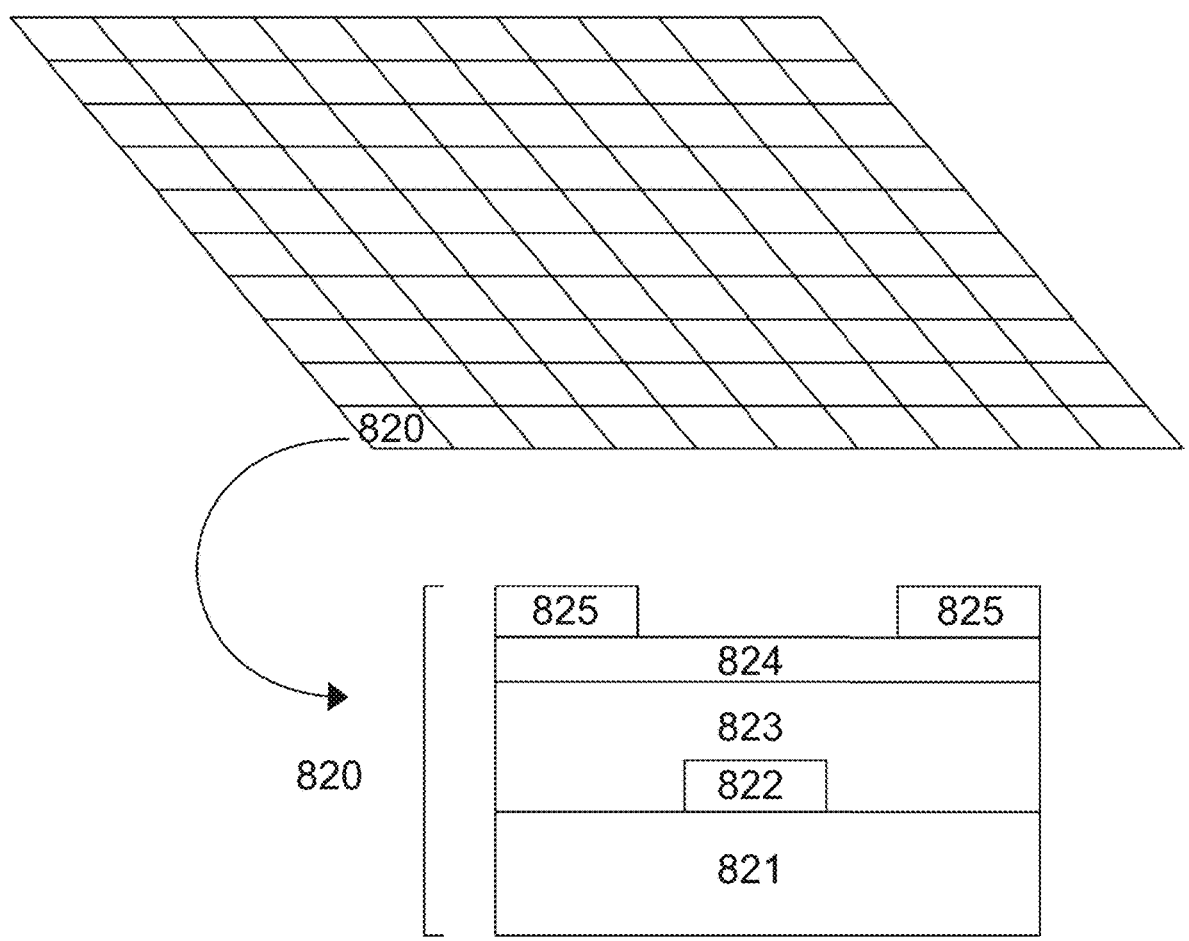
FIG. 9 is a schematic drawing showing an array of GFET and a GFET produced from the array.

In some embodiments, e.g., as shown in FIG. 9, the technology relates to an array of GFETs 900 for use in producing a plurality of GFETs 820 and a plurality of perovskite-graphene direct conversion sensors 800 by depositing perovskite compositions onto each of the GFETs 820 of the plurality of GFETs 820. Thus, in some embodiments, an array of GFETs 900 is produced, the array of GFETs is diced into a plurality of individual GFET chips 820, and a perovskite composition as described above is deposited upon each of the individual GFET chips. Accordingly, in some embodiments, the GFET array 900 comprises a substrate (e.g., a substrate comprising a silicon wafer (e.g., a 4-inch silicon wafer) covered with a layer of $SiO_2$ (e.g., a 90-nm thick layer of $SiO_2$)); and an array of back-gates (e.g., an array of Au or Cr/Au back-gates). In some embodiments, optical lithography and/or metallization of Cr/Au is used to deposit an array of electrically isolated back-gates. The array of GFETs 900 further comprises a gate dielectric (e.g., comprising a thin film of $Al_2O_3$); a graphene layer; and source-drain edge contacts (e.g., comprising Cr/Au). In some embodiments, the graphene layer comprises channels. Portions of the gate dielectric are removed (e.g., by optical lithography and/or wet etching) to expose the contacts of the back-gate 822. In some embodiments, the graphene is patterned, e.g., to provide channels in the graphene layer. In some embodiments, a GFET 820 further comprises an encapsulant (e.g., $Al_2O_3$) that encapsulates the source-drain edge contacts 825. In some embodiments, the encapsulant (e.g., $Al_2O_3$) is applied to the source-drain edge contacts 825 using photomask photolithography. Accordingly, embodiments provide that the electrodes (source-drain edge contacts 825) are encapsulated so that the graphene layer 824 provides the only electrical connection with the perovskite composition 810.

In some embodiments, the technology relates to fabricating a plurality (e.g., at least 20, 25, 30, 35, 40, 45, 50, 55, 60, 65, 70, 75, 80, 85, 90, 95, 100, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, or more) of GFET chips (e.g., approximately 1 cm×1 cm) that each comprises a pixel array; and depositing perovskite onto the graphene channels of each GFET chip to form a plurality of perovskite-graphene pixels (e.g., sensors). Next, in some embodiments, the perovskite-graphene GFET chips are placed onto chip carriers attached to printed circuit boards (PCB) with customized read-out electronics (e.g., a readout integrated circuit (ROIC) such as a high-speed counting ASIC (e.g., a Medipix3RX read-out board) or a multi-channel analyzer (MCA) ASIC) to provide a completed device (e.g., a detector).

Figure 10:
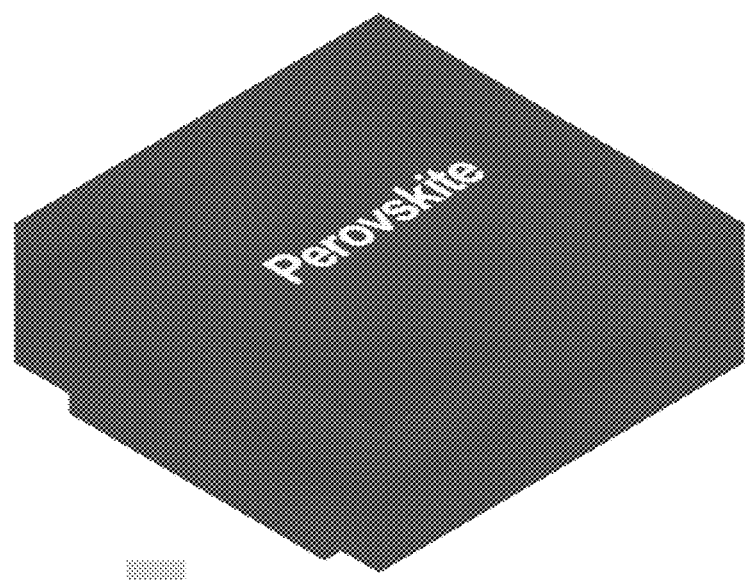
FIG. 10 shows a method of producing a perovskite-graphene direct conversion sensor comprising depositing a perovskite composition directly on a graphene surface
Figure 10:
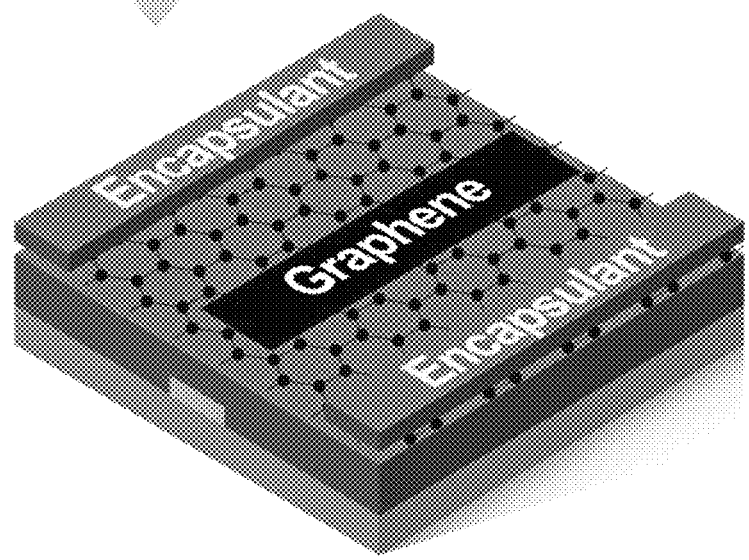

In some embodiments, e.g., as shown in FIG. 10, the technology provides methods for producing 1000 a perovskite-graphene direct conversion sensor. In some embodiments, methods for producing 1000 a perovskite-graphene direct conversion sensor comprise depositing 1010 a perovskite composition directly on a graphene surface. In some embodiments, depositing 1010 a perovskite composition directly on a graphene surface comprises growing a crystal on the graphene surface. In some embodiments, the graphene surface is provided by a GFET comprising a graphene surface.

Figure 11A:
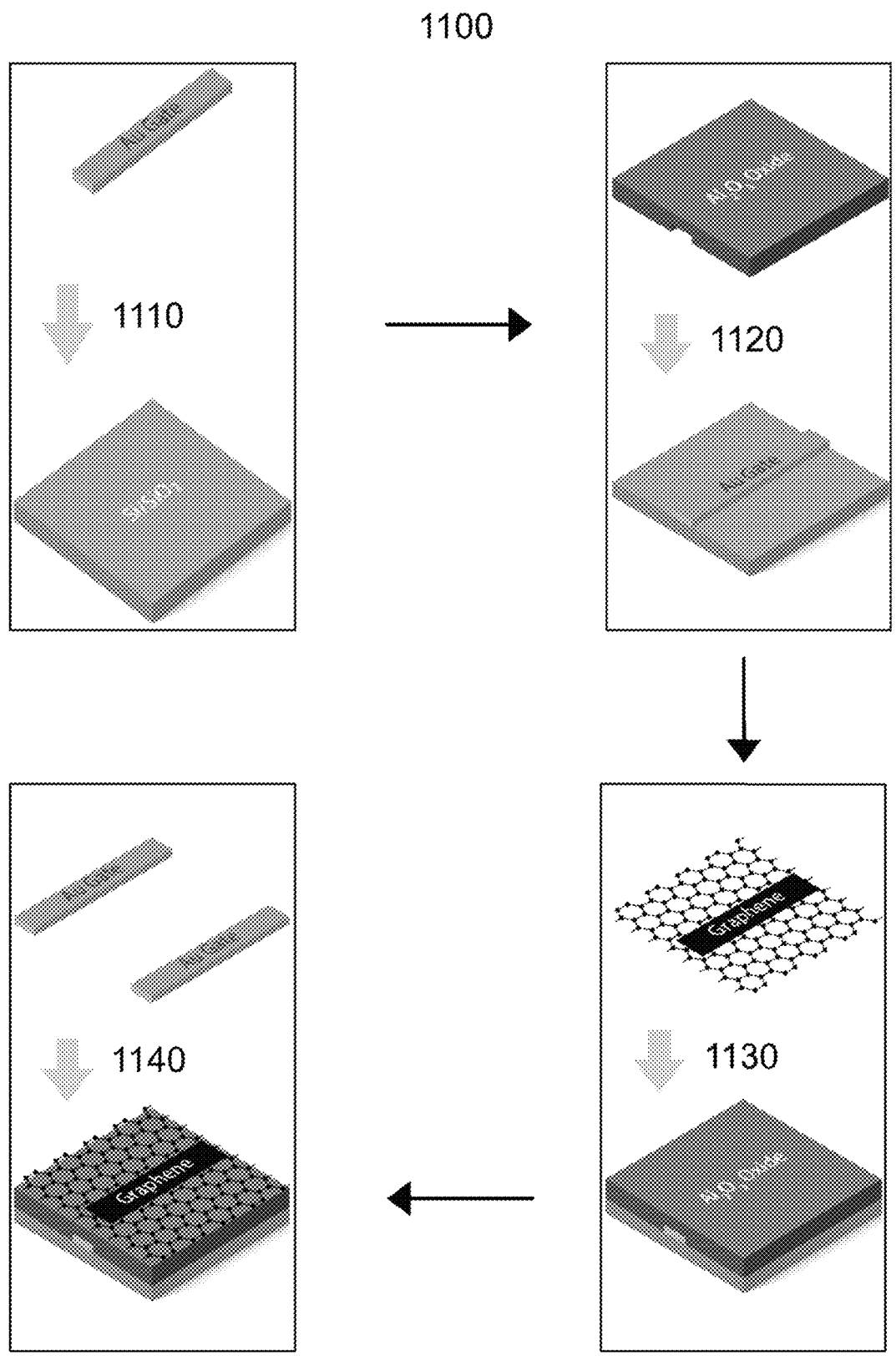
FIG. 11A and FIG. 11B show a method of producing a GFET comprising a graphene surface.

In some embodiments, e.g., as shown in FIG. 11A, methods for producing 1000 a perovskite-graphene direct conversion sensor comprise producing 1100 a GFET comprising a graphene surface. In some embodiments, methods for producing 1100 a GFET comprising a graphene surface comprise placing 1110 a back-gate (e.g., an Au or Cr/Au back-gate) on a substrate (e.g., a substrate comprising a silicon wafer covered with a layer of $SiO_2$ (e.g., a 90-nm thick layer of $SiO_2$)). In some embodiments, placing a back-gate on a substrate comprises electrically isolating a plurality of back-gates from each other (e.g., using optical lithography and metallization of Cr/Au via thermal/e-beam evaporation to create an array of back-gates electrically isolated from one another). In some embodiments, methods for producing 1000 a perovskite-graphene direct conversion sensor (e.g., comprising producing 1100 a GFET comprising a graphene surface) further comprise depositing 1120 a gate dielectric (e.g., comprising a thin film of $Al_2O_3$) on the back-gate and substrate. In some embodiments, depositing a gate dielectric comprises use of atomic layer deposition. In some embodiments, methods for producing 1000 a perovskite-graphene direct conversion sensor (e.g., comprising producing 1100 a GFET comprising a graphene surface) further comprise exposing the back-gate contacts (e.g., using optical lithography and wet etching of the dielectric to expose the back-gate contacts). In some embodiments, methods for producing 1000 a perovskite-graphene direct conversion sensor (e.g., comprising producing 1100 a GFET comprising a graphene surface) further comprise depositing 1130 graphene and/or patterning graphene on the dielectric surface. In some embodiments, methods for producing 1000 a perovskite-graphene direct conversion sensor (e.g., comprising producing 1100 a GFET comprising a graphene surface) comprise using optical lithography and etching (e.g., $O_2$ reactive ion etching) to produce channels in the graphene. In some embodiments, methods for producing 1000 a perovskite-graphene direct conversion sensor (e.g., comprising producing 1100 a GFET comprising a graphene surface) comprise producing 1140 contacts (e.g., source-drain edge contacts) on the graphene. In some embodiments, producing contacts (e.g., source-drain edge contacts) on the graphene comprises using optical lithography and metallization of Cr/Au via thermal/e-beam evaporation.

Figure 11B:
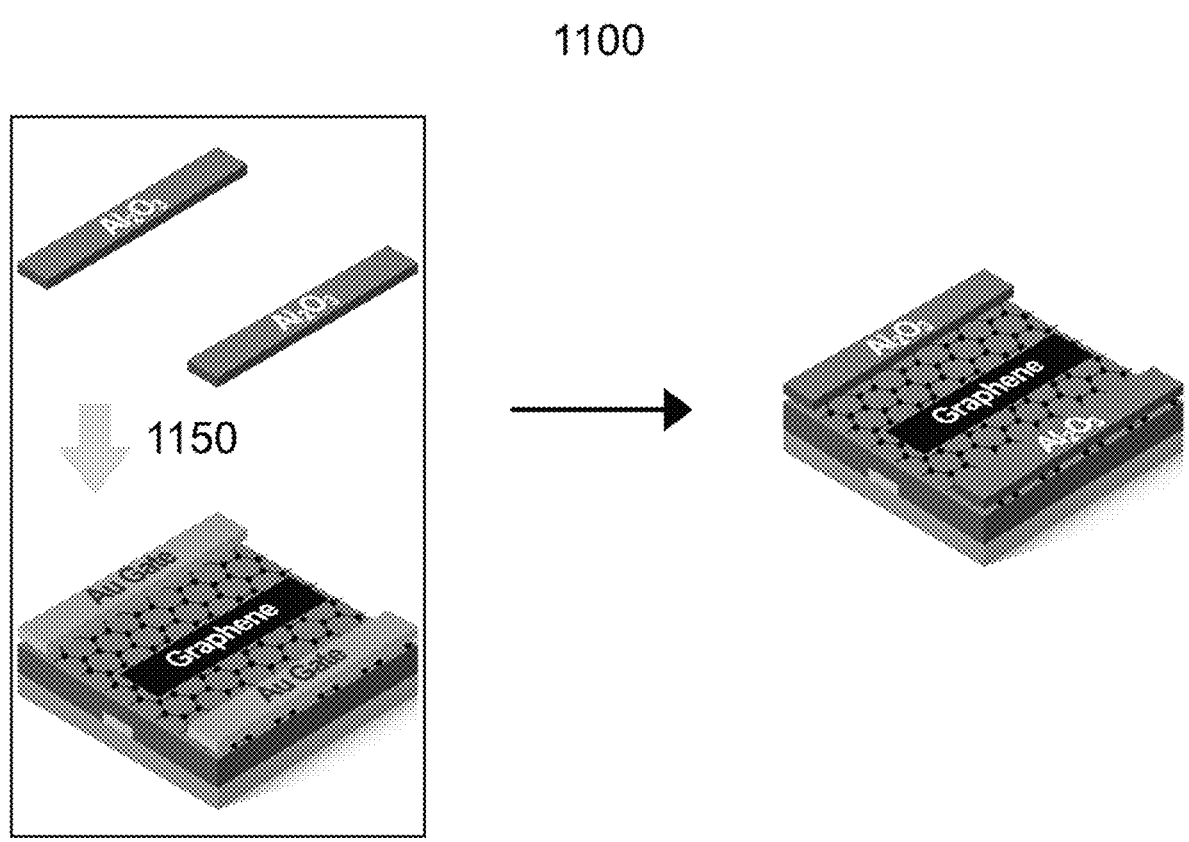

In some embodiments, e.g., as shown in FIG. 11B, methods for producing 1000 a perovskite-graphene direct conversion sensor (e.g., comprising producing 1100 a GFET comprising a graphene surface) comprise encapsulating 1150 the contacts (e.g., source-drain edge contacts) in an encapsulant (e.g., $Al_2O_3$). In some embodiments, encapsulating 1150 the contacts (e.g., source-drain edge contacts) in an encapsulant (e.g., $Al_2O_3$) comprises using photomask photolithography. Encapsulating the contacts (e.g., source-drain edge contacts) isolates the contacts (e.g., source-drain edge contacts) from the perovskite composition subsequently applied so that the graphene layer provides the only electrical connection with the perovskite composition. Encapsulating the contacts (e.g., source-drain edge contacts) minimizes and/or eliminates diffusion of metal from the contacts (e.g., source-drain edge contacts) into the perovskite material; thus, performance of the sensor is maximized over time.

In some embodiments, methods for producing 1000 a perovskite-graphene direct conversion sensor comprise producing an array of GFET chips and dicing the array of GFET chips into a plurality of GFET chips comprising a graphene surface. In some embodiments, methods for producing 1000 a perovskite-graphene direct conversion sensor comprise attaching a chip carrier or a field programmable gate array (FPGA) to a GFET. In some embodiments, methods for producing 1000 a perovskite-graphene direct conversion sensor comprise attaching (e.g., soldering) a printed circuit board (PCB) to a GFET. In some embodiments, methods for producing 1000 a perovskite-graphene direct conversion sensor comprise wire bonding the GFET electrodes to the PCB. In some embodiments, the PCB comprises connections (e.g., BNC connections) for attachment to external components.

Figure 11C:
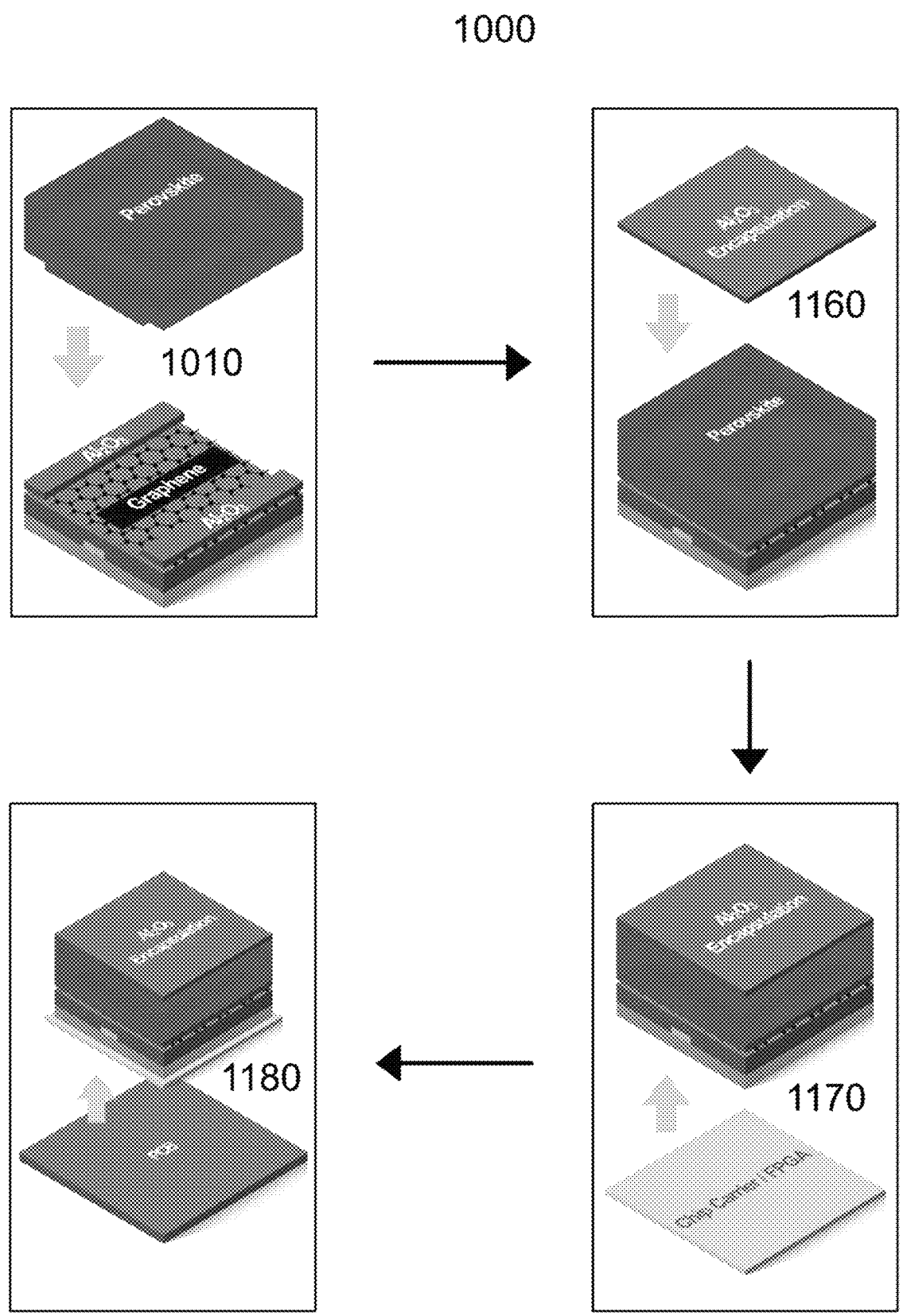
FIG. 11C shows a method for producing a perovskite-graphene direct conversion sensor comprising depositing perovskite directly onto a GFET chip.

In some embodiments, e.g., as shown in FIG. 11C, methods for producing 1000 a perovskite-graphene direct conversion sensor further comprise depositing 1010 perovskite directly onto a GFET chip. In some embodiments, depositing perovskite directly onto a GFET chip comprises using a hot-casting technique to provide crystal layer growth of perovskite on the GFET, e.g., as described in U.S. Pat. No. 10,770,239, which is incorporated herein by reference. In particular, using hot-casting deposition provides a single perovskite crystal or a perovskite composition comprising nearly single-crystalline quality promotes growth of thick layers of perovskite.

In some embodiments, methods for producing 1000 a perovskite-graphene direct conversion sensor comprise depositing polycrystalline films of perovskite on graphene using spin coating, doctor blade coating, tape casting, or an inverse temperature method. In some embodiments, methods for producing 1000 a perovskite-graphene direct conversion sensor comprise patterning the perovskite (e.g., using laser scribing) to isolate the perovskite over each graphene pixel (e.g., to reduce charge sharing effects). In some embodiments, methods for producing 1000 a perovskite-graphene direct conversion sensor comprise patterning the perovskite (e.g., using laser scribing) to expose the conductive pads (source, drain, and gate) of each pixel (e.g., to provide a contact that is structured to be wire-bonded to a chip carrier).

In some embodiments, e.g., as shown in FIG. 11C, methods for producing 1000 a perovskite-graphene direct conversion sensor comprise depositing 1160 a protection layer (e.g., $Al_2O_3$ or a polymer (e.g., PMMA)) on the perovskite. In some embodiments, methods for producing 1000 a perovskite-graphene direct conversion sensor comprise attaching 1170 a chip carrier or a FPGA to a GFET of a perovskite-graphene direct conversion sensor. In some embodiments, methods for producing 1000 a perovskite-graphene direct conversion sensor comprise attaching 1180 (e.g., soldering) a printed circuit board (PCB) to a GFET of a perovskite-graphene direct conversion sensor. In some embodiments, methods comprise wire bonding the GFET electrodes to the PCB. In some embodiments, the PCB comprises connections (e.g., BNC connections) for attachment to external components.

Figure 12:
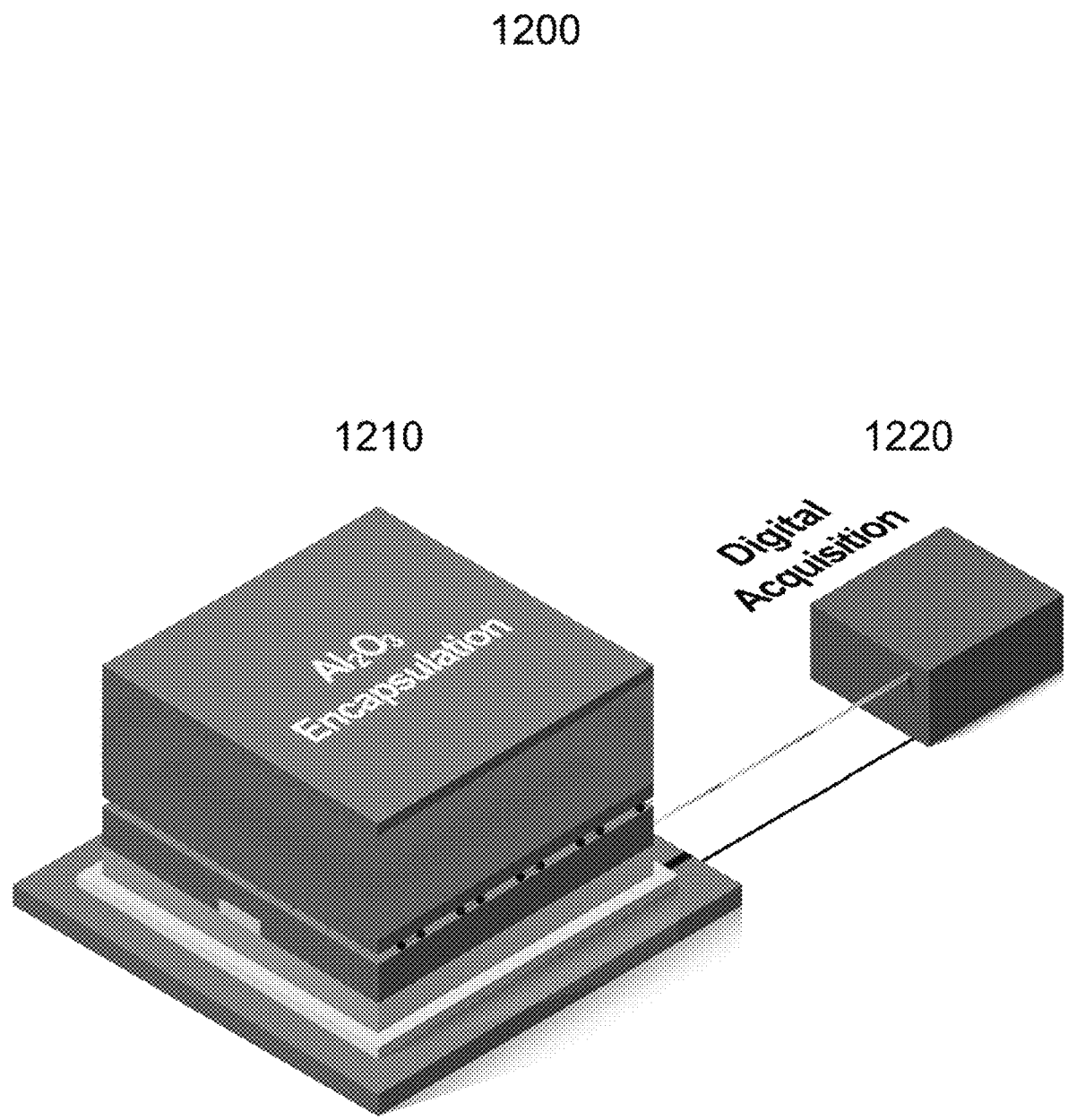
FIG. 12 shows a system comprising a perovskite-graphene direct conversion sensor and an external digital acquisition component.

In some embodiments, e.g., as shown in FIG. 12, methods comprise electrically connecting a perovskite-graphene direct conversion sensor 1210 to an external data acquisition component 1220, e.g., a digital acquisition component. The technology is not limited in the type of digital acquisition component used, e.g., embodiments provide that the digital acquisition component may be based on a large-area integrated circuit or active matrix array (AMA) such as AMA flat panel imagers (AMFPIs). In this configuration the pixel acquisition signal is multiplexed to a digitizer and then to a computer where the images can be viewed and/or using a wireless digital device with a screen that can remotely connect. The AMPFI image scanning control is controlled by the computer and/or readout board user interface that houses the x-ray sensor/detector. It is also possible to control remotely thru a wireless connection.

In the case of the perovskite photon counting sensor, the readout signal is first collected at the ASIC. The ASIC may be bump-bonded to the perovskite sensor, the perovskite sensor may be grown directly from the silicon ASIC, or the ASIC may be attached to the perovskite using a chip carrier on which the perovskite is directly grown. The ASIC is connected to an x-ray camera, which in turn may be connected to a CT scanner. Images and information can be viewed at a connected computer, or at the interface controller of the CT scanner, or any digital device that can make a wireless remote connection.

Systems

In some embodiments, the technology relates to systems comprising a perovskite sensor (e.g., a perovskite-graphene direct conversion sensor or a perovskite photon-counting sensor). For example, e.g., as shown in FIG. 12, embodiments provide systems 1200 comprising a perovskite-graphene direct conversion sensor 1210 and an external data acquisition component 1220, e.g., a digital acquisition component.

In some embodiments, systems comprise a source and a detector comprising a perovskite sensor (e.g., a perovskite-based photon-counting sensor or a perovskite-based energy integrating sensor as described herein). In some embodiments, systems further comprise an object to be imaged (e.g., a patient). In some embodiments, the object to be imaged is placed between the source and detector comprising a perovskite sensor (e.g., a perovskite-based photon-counting sensor or a perovskite-based energy integrating sensor as described herein). In some embodiments, systems comprise x-rays produced by the source, passing through and/or being attenuated by the object, and detected by the detector. In some embodiments, systems comprise an anti-scatter device (e.g., placed between the object and the detector).

In some embodiments, systems comprise an imaging display structured to display an image of the object. In some embodiments, systems comprise software comprising instructions for receiving x-ray intensity and/or energy information from the detector, converting the intensity and/or energy information into an image, and providing the image on a display. In some embodiments, systems comprise software comprising instructions for receiving electric signals from a detector and converting the electric signals into x-ray intensity and/or energy information. For example, in some embodiments, systems comprise software providing instructions for a method comprising receiving a signal from a detector, measuring the intensity of x-ray photons of one or more energies, calculating an intensity ratio of a first intensity of x-ray photons detected by the detector to a second intensity of x-ray photons produced by the source, and displaying an image using one or more intensity ratios.

Some embodiments of systems comprise a computer system, e.g., a computer and software encoding instructions for the computer to perform, e.g., to control data acquisition and/or analytical processes for processing data.

In various embodiments, a computer system includes a bus or other communication mechanism for communicating information and a processor coupled with the bus for processing information. In various embodiments, the computer system includes a memory, which can be a random access memory (RAM) or other dynamic storage device, coupled to the bus, and instructions to be executed by the processor. Memory also can be used for storing temporary variables or other intermediate information during execution of instructions to be executed by the processor. In various embodiments, the computer system can further include a read only memory (ROM) or other static storage device coupled to the bus for storing static information and instructions for the processor. A storage device, such as a magnetic disk or optical disk, can be provided and coupled to the bus for storing information and instructions.

In various embodiments, the computer system is coupled via the bus to a display, such as a cathode ray tube (CRT) or a liquid crystal display (LCD), for displaying information to a computer user. An input device, including alphanumeric and other keys, can be coupled to the bus for communicating information and command selections to the processor. Another type of user input device is a cursor control, such as a mouse, a trackball, or cursor direction keys for communicating direction information and command selections to the processor and for controlling cursor movement on the display. This input device typically has two degrees of freedom in two axes, a first axis (e.g., x) and a second axis (e.g., y), that allows the device to specify positions in a plane.

In some embodiments, steps of the described methods are implemented in software code, e.g., a series of procedural steps instructing a computer and/or a microprocessor to produce and/or transform data as described above. In some embodiments, software instructions are encoded in a programming language such as, e.g., BASIC, C, C++, C#, Objective-C, Java, MATLAB, Mathematica, Ruby, Perl, Object Pascal, PHP, Python, Swift, Scala, Common Lisp, Smalltalk, or R.

In some embodiments, one or more steps or components of acquiring a signal by an x-ray sensor, converting a signal into energy and/or intensity (e.g., a photon count) information, and/or displaying an image are provided in individual software objects connected in a modular system. In some embodiments, the software objects are extensible and portable. In some embodiments, the objects comprise data structures and operations that transform the object data. In some embodiments, the objects are used by manipulating their data and invoking their methods. Accordingly, embodiments provide software objects that imitate, model, or provide concrete entities, e.g., for numbers, shapes, data structures, that are manipulable. In some embodiments, software objects are operational in a computer or in a microprocessor. In some embodiments, software objects are stored on a computer readable medium.

Although the disclosure herein refers to certain illustrated embodiments, it is to be understood that these embodiments are presented by way of example and not by way of limitation.

EXAMPLES

Example 1—Perovskite-Graphene Energy Integrating X-Ray Sensor

During the development of embodiments of the technology provided herein, a perovskite-graphene energy integrating x-ray sensor ("pixel") was constructed and tested. A monolayer graphene channel was produced using chemical vapor deposition (CVD). The channel was 100-micron by 100-micron and included encapsulated planar edge contact electrodes. The graphene channel was formed on top of 90-nm silicon oxide, which was formed on top of 500-micron thick silicon. A layer of solution-processed $MAPbI_3$ perovskite approximately 10-micron thick was spin-casted on top of the graphene channel. Seeding, nucleation, and growth of the perovskite occurred directly on the graphene lattice and produced a seamless interface between the graphene and perovskite.

Figure 5:
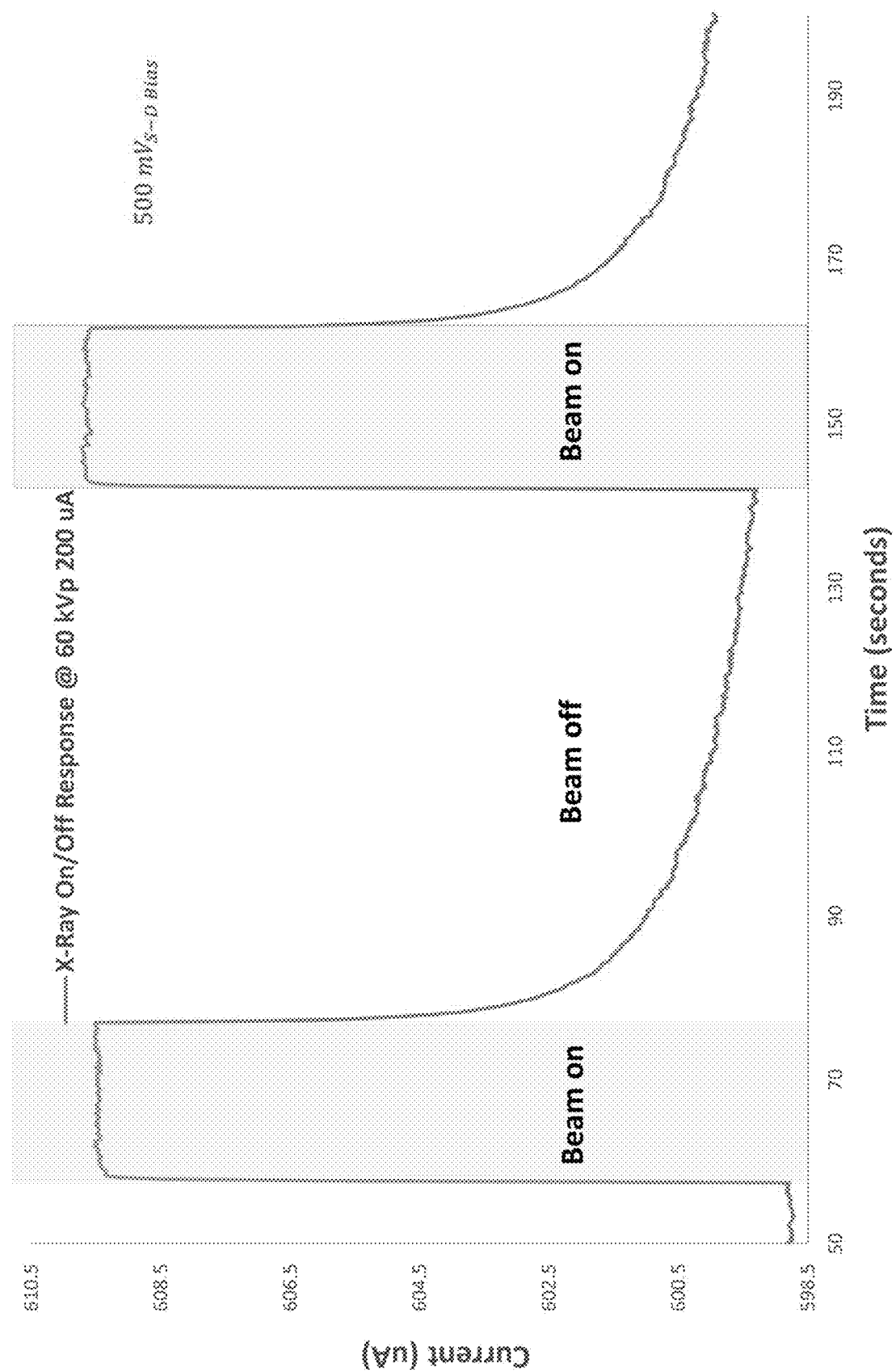
FIG. 5 is a plot showing the x-ray response of a perovskite-graphene sensor as described herein operating in energy operating mode.

Experiments were conducted to test the response of the perovskite-graphene sensor pixel. The perovskite-graphene sensor pixel was tested using a cone beam geometry x-ray tube operating at 60 kVp of tube voltage and 200 micro-amp of tube intensity, placing the source aperture at 3 cm from the perovskite-graphene sensor, and applying 500 mV to the source-drain charge collection bias in planar configuration (e.g., a photoconductor with photoconductive gain). Under these experimental conditions, data were collected indicating that the perovskite-graphene sensor material generated approximately 10 micro-amps of photocurrent. See FIG. 5. 10 micro-amps of photocurrent corresponds to a sensitivity of $6 \times 10^3$ $\mu C \times cm^{-2} \times R^{-1}$ to Mo-K$\alpha$ 17-keV photons under the experimental conditions (x-ray tube setting of 60 kVp, 200 μA, and 500 mV bias).

Further, the data collected from these experiments indicated that the photocurrent response displayed a linear gain from 10 mV to 1 V of source drain bias applied (2 micro-amps to 36 micro-amps, respectively). In addition, the data collected indicated that the perovskite-graphene detector photocurrent response displayed a linear gain from 100 micro-amp to 200 micro-amp of x-ray tube current, and displayed a linear gain in photocurrent from 25 kVp to 60 kVp. The largest photocurrent response signal detected was a 32 micro-amp current produced by the perovskite-graphene sensor material when a 1-V source-drain bias was applied to an x-ray tube setting of 60 kVp and 200 micro-amp and the source aperture was placed 3 cm from the perovskite-graphene detector. This response is equivalent to a response photocurrent density of 320 milli-amp per square cm.

Additional data for the perovskite-graphene direct conversion sensor are provided in Table 1. In particular, Table 1 provides data characterizing the detection sensitivity of a perovskite-graphene sensor comprising $MAPbI_3$ deposited directly on graphene structure and tested with molybdenum (Mo) K$\alpha$ characteristic x-rays produced in a standard cone beam geometry, comprising 17.4 keV photons at a dose rate of 180 mGy×second$^{-1}$, using a 1-V bias.

TABLE 1

Sensor imaging sensitivity

| Author | K-alpha Photon Energy (keV) | Material | Design | Thickness (μm) | Bias Voltage (V) | Sensitivity $\left(\dfrac{\mu C}{cm^2 \times R}\right)$ |
|---|---|---|---|---|---|---|
| Kabir [29] | 20 | a-Se | P | 200 | 2,000 | 0.24 |
| Kabir [29] | 20 | CZT | P | 300 | 75 | 2.55 |
| Yakunin [32] | 8 | MAPbI$_3$(Poly) | P | 60 | 80 | 2.5 |
| Wei [30] | 8 | MAPbBr$_3$(SC)/Si | D | 150 | −7 | 210 |
| Wei [30] | 8 | MAPbBr$_3$(SC)Si | D | 2,000 | −1 | 3.2 |
| Kairos Sensors [this work] | 17.4 | MAPbI$_3$(Poly)·G | P | 10 | 1 | $1.8 \times 10^4$ |

Divide Roentgen units by 0.00877 to convert to Gy$_{air}$

Table 1 provides data for sensors comprising amorphous selenium (a-Se), cadmium zinc telluride (CZT), perovskites (MAPbI$_3$ and MAPbBr$_3$/Si), and an embodiment of the perovskite-graphene sensor described herein comprising MAPbI$_3$ deposited directly on graphene structure ("Kairos Sensors"). Table 1 provides test data collected for conventional sensors as reported in the literature and test data collected for the perovskite-graphene sensor described herein during the development of embodiments of the technology. In Table 1, "SC" is a single crystal, "Poly" is polycrystalline, "Si" is silicon, and "G" is graphene; and the design column indicates a photoconductor ("P") or a diode ("D") design. Sensitivity units are provided in μC and indicated the micro-Coulomb photo response measured for a given active detector area. "R" is the x-ray exposure rate applied in Roentgen.

As shown in Table 1, the data indicated that the perovskite-graphene sensor described herein had a sensitivity of $2.1 \times 10^6$ μC×cm$^{-2}$×Gy$_{air}$ without external amplification. This detector provided an improvement in sensitivity of at least 4 orders of magnitude (e.g., 10,000×) relative to conventional detectors [20].

Example 2—Perovskite Sensor Simulation

Figure 6:
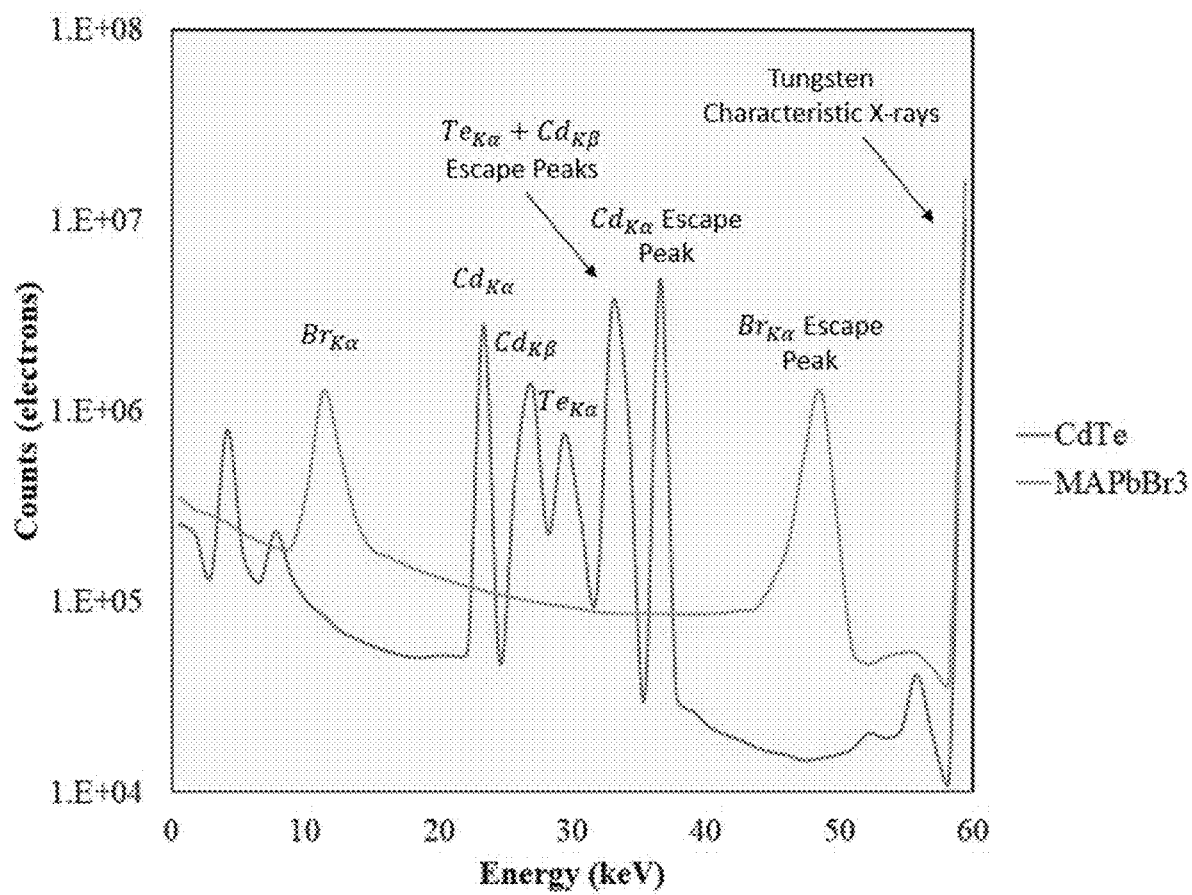
FIG. 6 is a plot showing the simulated spectral response of a conventional sensor and a perovskite sensor material described herein.

During the development of embodiments of the technology provided herein, experiments were conducted to model the spectral response of a perovskite sensor material described herein. In particular, a GATE simulation modeled the energy spectrum produced by the sensor material MAPbBr$_3$ for x-ray detection and the fluence of tungsten characteristic x-rays was simulated to represent a standard CT head-and-neck procedure. In the simulation, data were collected at energy channels used for material identification (e.g., 20-45 keV). As shown in FIG. 6, conventional sensor technologies (e.g., CdTe) produce in-sensor fluorescence that corrupts spectral efficiency within the energy channels used for material identification and thus reduces specificity accuracy of identifying materials. In particular, CdTe produces approximately 13 million fluorescence electrons throughout the 23-37 keV energy channels. In contrast, methylammonium lead tribromide (MAPbBr$_3$) produces no fluorescence photons for any energy channels within the 20-45 keV range.

Furthermore, when using singular energies of 25 keV and 35 keV for the observed energy channels, data collected from the simulation indicated that MAPbBr$_3$ identified adipose tissue and cortical bone with 80% and 98% accuracy, respectively, compared to the NIST mass attenuation coefficients for the given energies. Moreover, data from the simulation indicated that MAPbBr$_3$ provided 100% specificity for identifying the negative K-edge vector for the contrast agent iodine. In contrast, a GATE simulation of CdTe sensor material was modeled to observe identification of adipose tissue. Data collected during the simulation of the conventional sensor material indicated an accuracy of approximately 12%. Thus, the accuracy of material identification using the conventional technology was 68% less accurate than the material identification using the perovskite sensor material due to the spectral corruption of in-sensor fluorescence photons created by the characteristic x-rays from the tungsten anode of the x-ray tube.

Example 3—Full CT Spectrum Sensor Simulation

Figure 7:
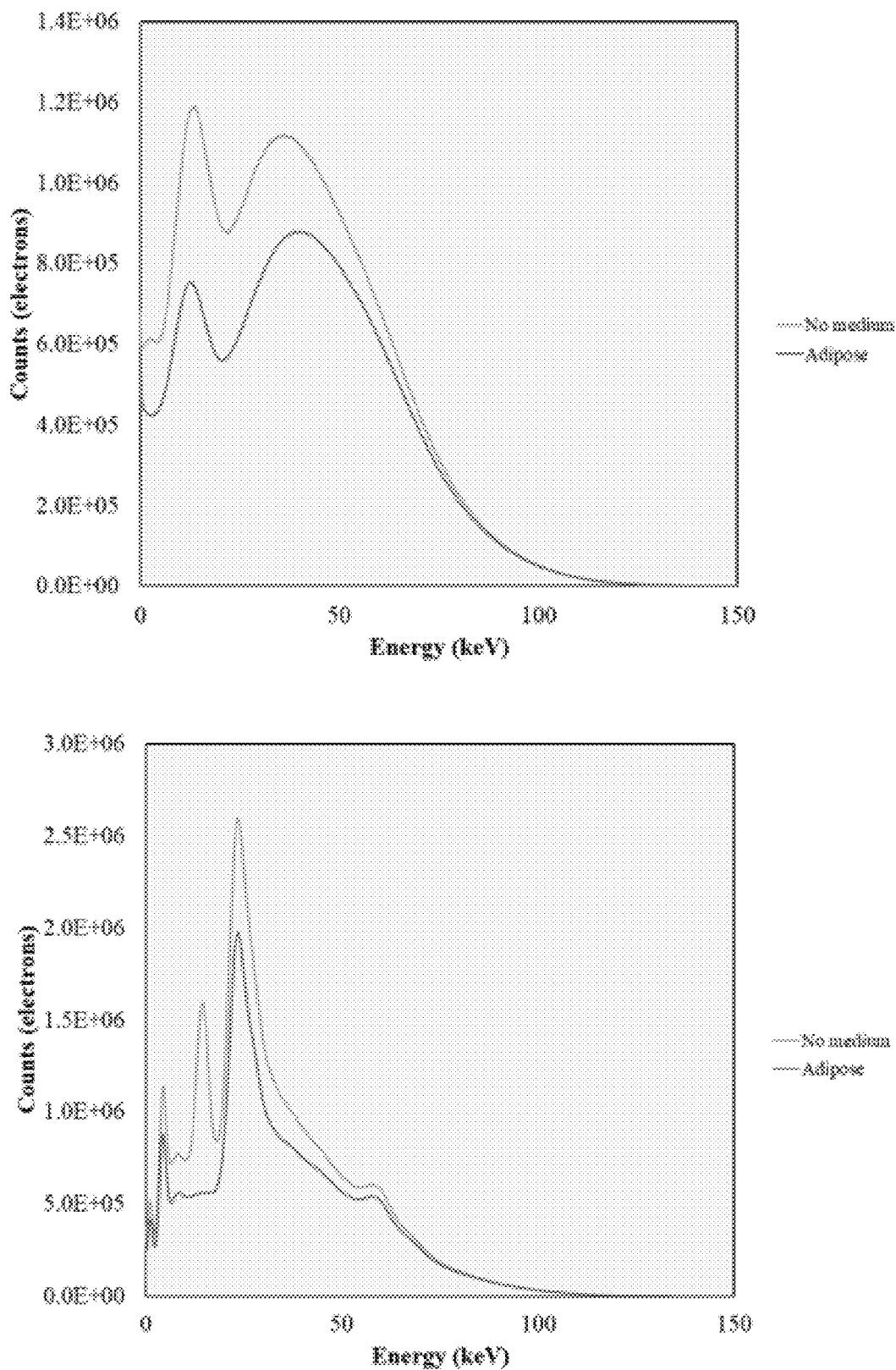
FIG. 7 is a pair of plots showing the results of simulations performed to model the energy spectrum detected for a CT scan using a $MAPbBr_3$ sensor material (FIG. 7, top) and a conventional CdTe sensor material (FIG. 7, bottom). In each plot, the top (lighter, gray) curve is the energy spectrum for the "No medium" reference simulation and the bottom (darker, blue) curve is for the "Adipose" experimental simulation.

During the development of embodiments of the technology described herein, experiments were conducted to model the whole energy spectrum detected for a CT scan using a MAPbBr$_3$ sensor material (FIG. 7, top) and a conventional CdTe sensor material (FIG. 7, bottom). Simulations were performed using TASMICS simulation package to model photon counts for each energy channel in the spectrum and the GATE simulation package was used to model the photon counts. In the simulations, a 2.5-mm thick aluminum filter was used to block low energy (e.g., 15 keV) photons from the x-ray source and thus reduce the simulated radiological dose to a patient. The resulting data were plotted to show the difference in sensor read-out from a CT scan (1.1 Specific Air Kerma—mGy) over the energy spectrum from 1 to 120 keV. In FIG. 7, the "No medium" curve represents the reference pixel with no material attenuation between the beam and the sensor, and the "Adipose" curve represents 5 cm of adipose tissue placed between the beam and the sensor. As shown in FIG. 7, 12 keV and 48 keV fluorescence peaks of the MAPbBr$_3$ sensor were detected (FIG. 7, top) using an energy resolution of 15 keV for the MAPbBr$_3$ detector. Further, 23 keV and 37 keV fluorescence peaks of the CdTe sensor were detected (FIG. 7, bottom) using an energy resolution of 5 keV for the conventional detector.

By comparing the "No medium" and "Adipose" spectra for the MAPbBr$_3$ and conventional CdTe sensors, the data indicated that the MAPbBr$_3$ sensor provided a high level of sensitivity (A) for identifying adipose tissue (FIG. 7, top). In comparison, the conventional CdTe sensor provided minimal sensitivity for identifying adipose tissue. Furthermore, the data (FIG. 7, top) indicated that the MAPbBr$_3$ sensor did not produce detectable fluorescence in the diagnostic energy range used to identify soft tissue (15-45 keV). Accordingly, the MAPbBr$_3$ perovskite sensor technology provides photon counts in at least two energy channels that can be used to measure the difference in attenuation for adipose tissue for at least two energies, thus providing a diagnostic radiology imaging technology having high specificity for identifying adipose tissue (FIG. 7, top). In contrast, the CdTe sensor has limited energy channels for measuring differences in attenuation. For example, the high fluorescence detected in the 15-25 keV range by the conventional sensor for the "No medium" reference (FIG. 7, bottom) decreases and/or eliminates the sensitivity of energy channels in the 15-25 keV range for material identification. Additionally, the data indicated a poor signal separation (A) at energies of 25 keV and greater for the conventional sensor (FIG. 7, bottom), thus further limiting the sensitivity of detecting adipose tissue with the conventional CdTe sensor.

Example 4—Multi-Pixel Perovskite-Graphene Direct Conversion Sensor Design and Testing A pixel array comprising multiple perovskite-graphene direct conversion sensors ("pixels") is designed and tested. In particular, a 3×3 pixel array is designed and tested to optimize thickness, composition, and pixel and/or pitch dimensions; to minimize and/or eliminate charge sharing between pixels, and to identify dose rates that maximize sensitivity. Experimental data are collected to optimize the composition and thickness of perovskite that maximizes detector performance (e.g., for mammography x-ray energies).

Figure 13:
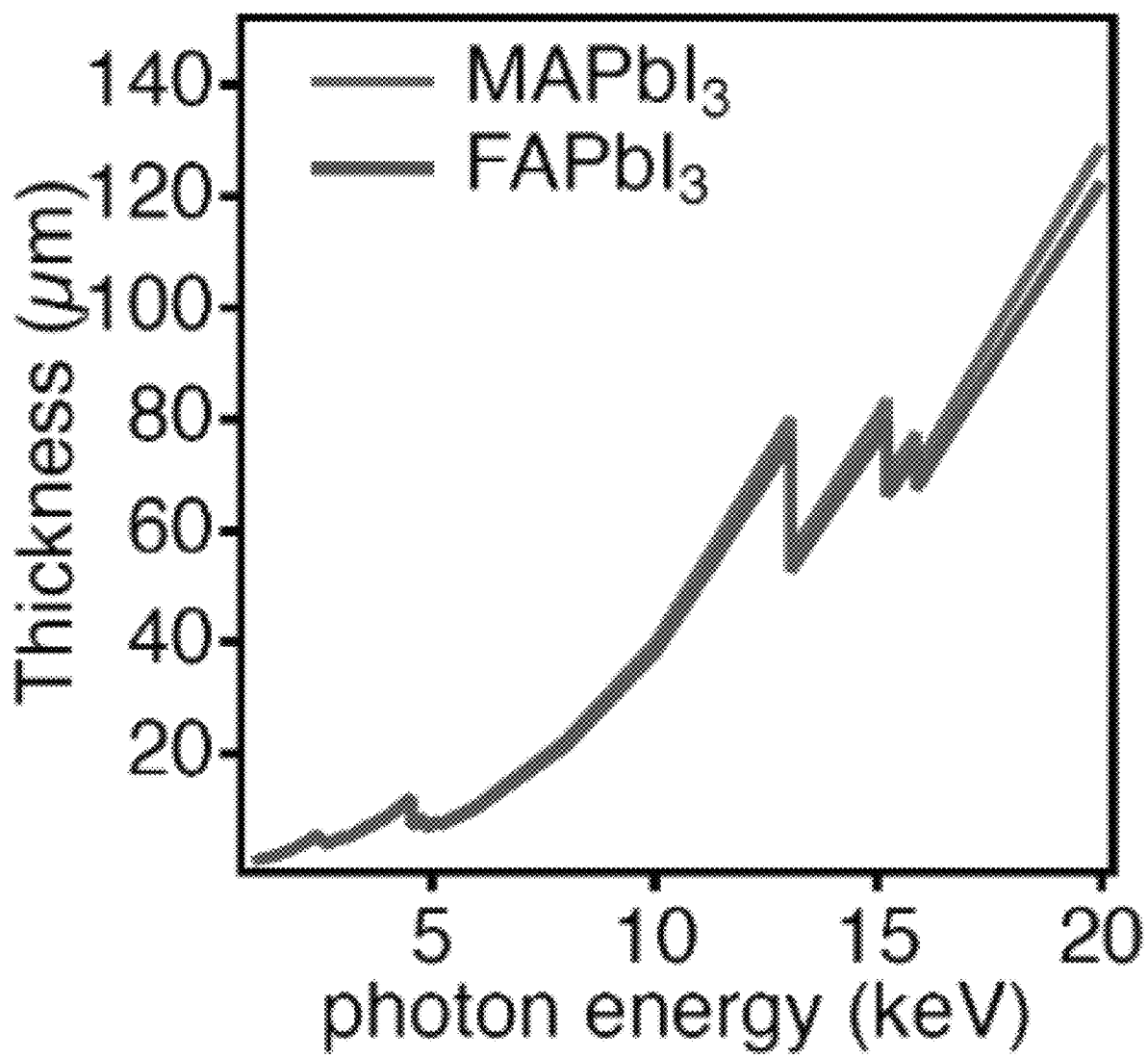
FIG. 13 is a plot showing perovskite thickness that attenuates 90% of photons as a function of photon energy. Data were produced using the NIST XCOM calculator.

During the development of embodiments of the technology provided herein, perovskite attenuation was calculated as a function of photon energy and the data indicated that a thickness of approximately 120 µm perovskite (e.g., comprising MAPbI$_3$ or FAPbI$_3$) provides 90% attenuation for typical mammography Mo-Kα photon energies of approximately 17 keV [44], [45]. FIG. 13. Further, the diffusion lengths of the perovskite compositions are between 10-1000 µm [46]-[48]. Accordingly, design of the pixel array comprising multiple perovskite-graphene direct conversion sensors comprises a perovskite composition having a thickness of 100 to 1000 µm (e.g., 50 to 500, 100 to 500, 100 to 400, 100 to 300, or 100 to 200 µm).

Pixelating perovskite sensor contact pads with standard photolithography procedures presents challenges because of solvent incompatibility that causes insufficient and/or unusable spatial resolution for medical imaging [13]-[36]. Accordingly, embodiments of the technology provided herein grow the perovskite directly on a pre-patterned graphene lattice, which allows for perovskite contact pad pixilation without using photolithography. The perovskite-graphene direct conversion sensors ("pixels") comprise finely featured pixels and thus provide improved spatial resolution relative to conventional sensors that detect an x-ray signal without the perovskite material contacting with the electrodes. The electrodes are encapsulated and thus isolated from the perovskite material, which eliminates and/or minimizes metal diffusion that can degrade the perovskite performance or create ion drift associated with sensor polarization.

Additionally, most previous perovskite designs have utilized a diode configuration, which provides low sensitivity and requires a significant bias, resulting in high power consumption and a low signal-to-noise ratio [13]-[36]. In contrast, embodiments of the technology provided herein have a sensitivity at least 2 orders of magnitude better than conventional perovskite sensors and operate with significantly less bias (e.g., approximately 1 V) [13]-[36].

Fabrication is performed according to method embodiments of the technology described herein. See, e.g., FIG. 10, FIG. 11A, FIG. 11B, FIG. 11C, and FIG. 12. In particular, 48 graphene-field-effect-transistors (GFET) chips (1 cm×1 cm), each having a 3×3-pixel array, are fabricated. Perovskite is deposited onto the graphene channels of the GFET chips to form perovskite-graphene pixels. The perovskite-graphene GFET chips are placed onto chip carriers attached to printed circuit boards (PCB) with customized read-out electronics (e.g., a high-speed counting ASIC (e.g., a Medipix3RX read-out board) or a multi-channel analyzer (MCA) ASIC) to provide a completed detector device.

In particular, each graphene pixel has a pair of source/drain electrodes for applied bias and charge collection and a third electrode for independent modulation of each pixel. The graphene pixels have programmable gain and a uniform pixel response. Graphene chips are manufactured by Graphenea Inc. using a customized process based on 4-inch graphene wafer technology. The fabrication process starts with an array of Au back-gates on top of a 4-inch Si wafer covered by a 90 nm thick layer of SiO$_2$. Optical lithography and metallization (Cr/Au via thermal/e-beam evaporation) are used to create an array of back-gates electrically independent from one another. An Al$_2$O$_3$ thin film is deposited via atomic layer deposition (ALD), which will serve as a gate dielectric. Optical lithography and wet etching of the Al$_2$O$_3$ are used to expose the back-gate contacts.

The next step is graphene deposition and patterning, where graphene is transferred on the Al$_2$O$_3$ surface. Optical lithography and etching via O$_2$ reactive ion etching are used to define the graphene channels. Finally, the graphene contacts are provided by optical lithography and metallization (Cr/Au via thermal/e-beam evaporation) to create the array of source-drain edge contacts. The wafer is diced into GFET chips ready for perovskite deposition.

Perovskite is deposited directly onto the GFET chips at Los Alamos National Laboratory (LANL). The perovskite composition directly affects the x-ray absorption and the mean diffusion length, thus setting the maximum sensitivity of the detector. Accordingly, perovskite structures are used that are known to deliver high performance for x-ray detection (e.g., methylammonium (MA) lead triiodide [75] and formamidinium (FA) lead triiodide [76]). Specifically, LANL uses a hot-casting technique described in U.S. Pat. No. 10,770,239, which is incorporated herein by reference, to improve the crystal layer growth. A hot-casting deposition promotes the crystallinity to achieve near single-crystalline quality and thick layer growth appropriate for absorbing x-rays. In some fabrications, polycrystalline films are deposited onto GFETS using spin coating, doctor blade coating, tape casting, or an inverse temperature method, which allow deposition of thin films and films as thick as 50 µm over a large area (e.g., on the order of a square centimeter). Perovskite patterning is performed using laser scribing to isolate the perovskite over each graphene pixel and thus reduce charge sharing effects. The patterning process is also used to expose the conductive pads (source, drain, and gate) of each pixel, thus providing them for wire-bonding to the chip carrier. A protection layer (e.g., Al$_2$O$_3$ or PMMA) is deposited on the completed detector to minimize performance degradation. This final step completes the fabrication process for the perovskite-graphene GFET chip. Forty-eight perovskite-graphene GFET chips are attached to chip carriers and then soldered onto PCBs. The chip carrier and PCB are provided with BNC connections ready for 'plug-andplay' measurements. Wire bonding from the pixel electrodes to the PCB will complete the fabrication process.

Twenty-four of the detectors are tested at the University of Utah for electrical and x-ray characterization. The other 24 detectors are tested independently by MARS Bioimaging for comparison with the results from the University of Utah. In particular, experiments are conducted to test perovskite composition (e.g., MAPbI$_3$ and FAPbI$_3$), thickness (e.g., 10 µm and 50 µm), pixel size (e.g., 10×10 µm$^2$, 100×100 µm$^2$, and 500×500 µm$^2$), and two different pitches (e.g., 50 µm and 500 µm). Accordingly, these experiments test 4 variables on 24 detectors.

Experiments are conducted on four detectors (two comprising MAPbI$_3$ and two comprising FAPbI$_3$) having 10 µm or 50 µm perovskite thickness, with 10×10 µm$^2$ pixels, and 50 µm pitch. Experiments are conducted on four detectors (two comprising MAPbI$_3$ and two comprising FAPbI$_3$) having 10 µm or 50 µm perovskite thickness, with 10×10 µm$^2$ pixels, and 500 µm pitch. Experiments are conducted on eight detectors (two comprising MAPbI$_3$ and two comprising FAPbI$_3$) having 10 µm or 50 µm perovskite thickness, with 100×100 µm$^2$ pixels, and 50 µm pitch. Experiments are conducted on eight detectors (two comprising MAPbI$_3$ and two comprising FAPbI$_3$) having 10 µm or 50 µm perovskite thickness, with 500×500 µm$^2$ pixels, and 50 µm pitch.

The graphene quality and thickness are characterized by optical microscopy analysis and Raman spectroscopy at Graphenea Inc. Perovskite quality and thickness are characterized by photoluminescence spectroscopy, scanning electron microscopy, and x-ray diffraction at LANL labs. Electrical properties (e.g., bulk resistivity and charge carrier mu-tau product) are measured via time-resolved microwave conductivity (TRMC). Material characterization methods are performed on at least one pixel of the perovskite-GFET chip for each of the 48 detectors.

Electrical characterization is performed by Graphenea Inc. and includes data describing mobility, Dirac point spread, and carrier density. After perovskite deposition and PCB integration, electrical characterization of the completed detectors is performed at the University of Utah. At least one pixel of each of the 24 perovskite-graphene GFET chips is tested. In particular, the graphene resistance of at least one pixel of each of the 24 perovskite-graphene GFET chips is measured by applying a bias between the drain and source electrodes and measuring the drain current. Transfer curves are measured by applying a gate voltage while measuring the drain current. Crossgate effects are measured via the drain current from one of the detector pixels while applying a gate voltage to the adjacent pixels.

The expected perovskite composition is be confirmed via X-ray diffraction. I-V curves indicate graphene resistance behavior.

Perovskite mu-tau product is expected to be $1\times10^{-3}\times$ cm$^2\times$V$^{-1}$. The average graphene mobility is expected to be 1100 cm$^2\times$V$^{-1}\times$s$^{-1}$.

To perform experiments to measure the photocurrent as a function of photon energy for the detectors, photon energy dependence is measured for the 24 detectors by applying a 100-mA x-ray tube current and measuring the response photocurrent of the detector when applying a tube voltage setting of 20, 40, or 60 keV to each detector. Thus, 72 photon energy dependence measurements are conducted. These measurements provide the X-ray sensitivity response as a function of photon energy. The peak sensitivity iz quantified using an ion chamber to measure the exposure rate.

To perform experiments to measure the photocurrent as a function of photon intensity, the intensity dependence of the 24 detectors is measuring using a tube voltage setting of 40 keV and measuring the response photocurrent when applying 200, 100, or 50 mA to each detector. Thus, 72 intensity dependence measurements are conducted.

To perform experiments to measure sensitivity as a function of exposure rate, the detector configuration that provides the most sensitivity from the photon energy and intensity measurements is assessed for exposure rates of approximately 1 µGy, 10 µGy, 100 µGy, 1 mGy, 10 mGy, 100 mGy, and 1 Gy per second to identify the maximized sensitivity for a given exposure rate. These measurements are done on one detector for a total of seven measurements.

To perform experiments for x-ray characterization, a specialized chamber is mounted on a beamline with motion control to provide precise positioning of the sample within the x-ray beam. For x-ray characterization, the on-and-off ratio and the material stability (polarization) is monitored for 4,000 seconds using ten sets of an on period (5 seconds) and off period (5 seconds) and providing a rest period of 60 seconds between each set (five measurements on one detector). The monoenergetic beam is approximately 20 keV in photon energy, the beam spot size is approximately 500×500 µm$^2$, and the flux is between $10^3$ to $10^{10}$ photons×cm$^{-2}\times$second$^{-1}$. Additionally, one measurement from each pixel in the 3×3 array from one detector measures the rise/fall time. On the same detector, a focused beam is placed onto the center pixel, and the surrounding pixels are independently measured to check for charge sharing.

At an exposure rate of 100 µGy × second$^{-1}$, the expected sensitivity is $1\times10^5$ µC×cm$^{-2}\times$R$^{-1}$ using the optimized perovskite composition, thickness, and pixel/pitch dimensions. The rise time is expected to approximately 10-50 of milliseconds and the recovery time is expected to be approximately 0.01 to 0.05 milliseconds (when reversing the source-drain polarity to reset the detector's response). Polarization is expected to be negligible and pixel charge sharing is not expected, which is consistent with the perovskite-graphene tested during experiments described herein (e.g., as described in Example 1).

Example 5—Multi-Pixel Perovskite Photon Counting Sensor Design and Testing

A perovskite x-ray (APeX) sensor is designed and tested. The APeX sensor replaces conventional cadmium and tellurium direct conversion materials in a sensor for spectral imaging. The APeX sensor is not limited to pitch distances that minimize k-fluorescence effects, thus providing a technology for high resolution spectral detectors for improved identification of tissues and materials.

As shown in FIG. 6, simulation results indicated no methylammonium or lead x-ray fluorescence from methylammonium lead tribromide perovskite (MAPbBr$_3$). The bromide Ka and Ka-escape peaks are at 12 keV and 48 keV, thus leaving an extensive range of energies between approximately 12 keV and 48 keV that is not affected by k-fluorescence. Accordingly, the methylammonium lead tribromide perovskite (MAPbBr$_3$) provides improved material identification relative to conventional sensors that have decreased sensitivity in this energy region due to in-sensor fluorescence of conventional sensor materials. Additionally, the patient dose is reduced because pixels with a pitch size smaller than 100 microns are provided in the sensor without suffering spectral distortion from k-fluorescence. As a result, x-ray count rates are improved by two orders of magnitude relative to conventional sensors [49] due to the small pixel effect [50]. Accordingly, The APeX sensor improves spectral efficiency for superior diagnostic accuracy, reduces the cost relative to traditional cadmium and tellurium-based sensors by an order of magnitude, increases detector count rates (e.g., to meet the flux rate requirements of CT applications), reduces patient scan times, enhances spatial resolution, and reduces radiological dose to the patient.

Figure 14:
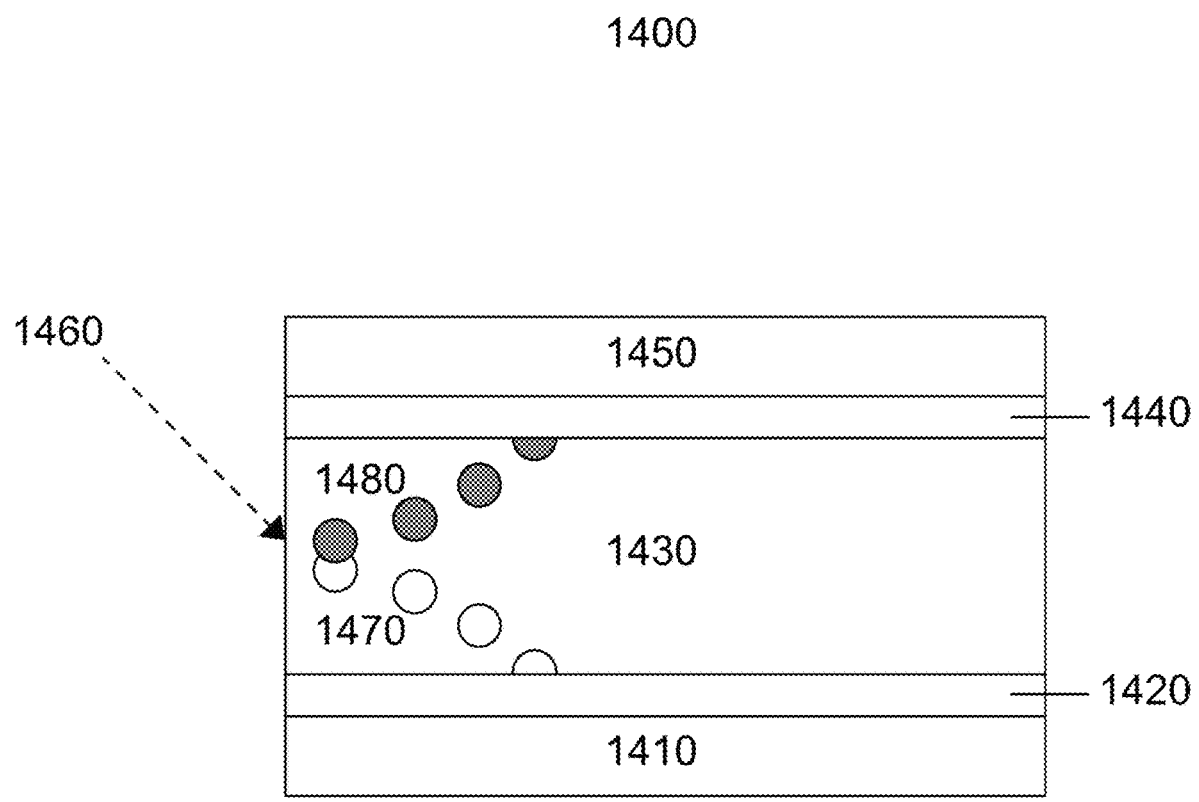
FIG. 14 is a schematic drawing showing a side view of a perovskite pixel.

The APeX sensor comprises a compositionally engineered perovskite material that minimizes and/or eliminates fluorescence within energy channels that are used for medical imaging (e.g., in the range of approximately 10 keV to 50 keV). A sensor was designed as shown in FIG. 14 to provide a sensing pixel. As shown in FIG. 14, the pixel 1400 comprises a lead electrode 1410, an N-interlayer 1429, a perovskite composition 1430, a P-interlayer 1440, and a gold electrode 1450. The pixel comprises reversed-biased electrodes, which produces a depleted region in the volume of the sensor, where the dark current is reduced to a minimum. An incident x-ray 1460 ionizes of an electron-hole pair, and the hole 1470 and electron 1480 charges are collected at the lead electrode 1410 and gold electrode 1450, respectively. In addition, the single-pixel perovskite sensor technology is used to make a pixelated sensor comprising a large array of contact pads ready for bump-bonding via fine-feature (few tens of microns) shadow mask techniques. Surface optimization techniques are used to reduce the leakage and lower the noise of the perovskite sensor. Further, the single-pixel sensor is attached to a high-speed counting ASIC (e.g., the Medipix3RX read-out board).

Single-crystal perovskite sensors comprising pixelated electrodes are fabricated. A solution-based method is used to grow MAPbBR$_3$ single-crystal perovskite x-ray sensors. In particular, solution-based methods and growth condition control can reproducibly produce a large size of MAPbBR$_3$ single-crystal perovskite x-ray sensors (e.g., 14×14×2 mm) [51]. During the development of embodiments of the technology described herein, data collected during experiments indicated that adding 5% of chlorine in the precursor decreases defect density and suppresses voltage-induced instability [52].

These fabrication methods are used to grow 14×14×2 mm single perovskite (MAPbBr$_3$) crystals and polish the surface for electrode deposition. The metal electrodes in a 100×100 pixelated array are (110×110 μm$^2$ with 110 μm pitch) are deposited through a shadow mask by a vacuum deposition method. After growth and fabrication, the devices are characterized by current-voltage and impedance spectroscopy to measure the physical characteristics of the sensor (e.g., dark conductivity, dielectric constant, and defect density) that are important for single-photon counting. The targeting dark resistivity is much greater than $1\times10$ ohm×cm$^{-1}$ in a diode to output clean pulse signals [53], [54].

In addition to electrical characterization, the sensors are characterized using optical spectroscopy (e.g., UV-vis absorption spectroscopy and photoluminescence spectroscopy) to confirm the material composition and crystal quality.

To fabricate highly sensitive single-pixel prototype MAPbBr$_3$ sensors, the surface charge recombination rate is reduced to minimize surface recombination that significantly contributes to the saturation current (or dark current) and/or reduces the sensitivity of the sensors. During the development of embodiments of the technology provided herein, data from experiments indicated that the MAPbBr$_3$ surface can be passivated to reduce the leakage current by oxygen using UV-ozone treatment. Accordingly, a UV-ozone treatment is used to passivate the MAPbBr$_3$ surface [30]. To collect the x-ray generated carriers effectively from the MAPbBr$_3$ layer, both p-type and n-type layers are formed on the MAPbBr$_3$ surface (FIG. 14). Considering the carrier concentration and the mobility of the p- and n-type semiconductors and processing compatibility, p-type NiO$_x$ and n-type TiO$_2$ are used to form the sensor (FIG. 14). To fabricate prototype devices, pulsed laser deposition is used to grow metal oxide layers and e-beam evaporation is used to deposit metal contacts. Pulsed laser deposition provides a powerful technique to grow metal oxide films at relatively low temperatures with well-controlled metal-oxygen stoichiometry, which provides control of the work function and doping density near the interface. Furthermore, the use of pure oxygen during the growth of metal oxide films may provide advantages for surface passivation as discussed above.

A thin-film encapsulation technology is used to encapsulate the sensor device. Specifically, sputtering is used to deposit a dense Al$_2$O$_3$ layer to prevent the device from direct exposure to the environment and thus provide environmental stability to the MAPbBr$_3$ material and hole and/or electron transport layers.

Perovskite sensors are attached by bump-bonding to a Medipix3RX ASIC. Upon material characterization, a dark resistivity of $1\times10^9$ ohm×cm$^{-1}$ is expected.

The perovskite sensors are used to obtain 3D CT images of test phantoms and excised biological samples in a MARS Bioimaging Ltd. research CT scanner. These images are compared against 3D images obtained by MARS Bioimaging Ltd. using CdTe and CZT sensors for material identification and quantification (e.g., using density as an identifying characteristic). "Material" in this context refers to biological materials (e.g., water, lipid, and calcium), contrast materials (e.g., iodine and gadolinium), and implant materials (e.g., as plastic, steel, and titanium).

The perovskite sensors with pixelated contact pads are low-temperature solder-bump bonded to Medipix3RX ASICs via a low-temperature bump-bonding process (approximately 80° C.) [55], using facilities available to MARS Bioimaging Ltd.

Once the perovskite sensor is connected to the Medipix3RX ASIC, a bias voltage of 50 mV×μm$^{-1}$ is applied across the sensor and the dark-current/leakage current is measured.

The peroskite-Medipix3RX modules are placed in a MARS Bioimaging Ltd. small-bore CT research scanner. A series of x-ray images is processed with standard iterative reconstruction algorithms to obtain 3D CT images of test phantoms and excised biological samples. A 100-mm diameter phantom comprising several different materials (adipose, calcium, bone equivalent) is placed inside the MARS Bioimaging Ltd. CT scanner with the perovskite-Medipix3RX camera and compared with a conventional CdTe sensor.

Accordingly, working perovskite-Medipix read-out modules are attached to MARS Bioimaging Ltd. read-out electronics ready for installation into the MARS Bioimaging Ltd. CT scanner. A bias voltage of 50 mv×μm$^{-1}$ is applied across the perovskite sensor, and a dark current/leakage current of approximately 100 nA×cm$^{-2}$ is expected for a 2-mm thick perovskite sensor. The perovskite sensors are expected to be approximately 50% more accurate than CdTe in measuring the density (e.g., g×mL$^{-1}$) of lipid, calcium, and bone equivalent to the NIST known density values. The perovskite sensor performance is expected to produce images with comparable, or better, 3D calcium maps in units of g×mL$^{-1}$.

An oxygen plasma treatment is used to provide increased passivation of the MAPbBr$_3$ surface, e.g., if a high dark current conductivity is observed on the perovskite crystal. Oxygen plasma treatment may be provided in two rounds of testing to provide a feedback loop to optimize each round of devices being tested. A silver epoxy bump-bonding method is used if the low-temperature bump-bonding process decreases the perovskite sensor expected electrical characteristics. The silver epoxy bump-bonding method provides the advantage of not using increased temperature to connect the sensor contact pads to the ASIC.

All publications and patents mentioned in the above specification and provided in the References section below are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

REFERENCES

[1] T. Schulman, "Si, CdTe and CdZnTe radiation detectors for imaging applications," Dissertation, Department of Physics, University of Helsinki, 2006.

[2] G. F. Knoll, "Radiation Detection and Measurement," 4th ed. 2010.

[3] S. M. Arnab and M. Z. Kabir, "Impact of charge carrier trapping on amorphous selenium direct conversion avalanche X-ray detectors," J. Appl. Phys., vol. 122, no. 13, 2017.

[4] S. M. Arnab and M. Z. Kabir, "A Novel Amorphous Selenium Avalanche Detector Structure for Low Dose Medical X-Ray Imaging," IEEE Trans. Radiat. Plasma Med. Sci., vol. 4, no. 3, pp. 319-326, 2019.

[5] D. C. Hunt, K. Tanioka, and J. A. Rowlands, "X-ray imaging using avalanche multiplication in amorphous selenium: Investigation of intrinsic avalanche noise," Med. Phys., vol. 34, no. 12, pp. 4654-4663, 2007.

[6] J. B. Frey, G. Belev, O. Tousignant, H. Mani, L. Laperriere, and S. O. Kasap, "Dark current in multilayer stabilized amorphous selenium based photoconductive x-ray detectors," J. Appl. Phys., vol. 112, no. 1, pp. 1-10, 2012.

[7] J. R. Scheuermann, A. H. Goldan, O. Tousignant, S. Léveillé, and W. Zhao, "Low dose digital X-ray imaging with avalanche amorphous selenium," Med. Imaging 2015 Phys. Med. Imaging, vol. 9412, no. 1, p. 94120E, 2015.

[8] M. J. Yaffe and J. G. Mainprize, "Detectors for digital mammography," Technol. Cancer Res. Treat., vol. 3, no. 4, pp. 309-324, 2004.

[9] W. M. Shelly Lille, "Chapter 15 Creating the Digital Image," Mammographic Imaging A Pract. Guid., pp. 326-357, 2018.

[10] H. Huang and S. Abbaszadeh, "Recent Developments of Amorphous Selenium-Based X-Ray Detectors: A Review," IEEE Sens. J., vol. 20, no. 4, pp. 1694-1704, 2020.

[11] X. Qian, "Fundamentals of digital mammography," Phys. Mammographic Imaging, pp. 3-10, 2012.

[12] J. R. Scheuermann, A. Howansky, M. Hansroul, S. Léveillé, K. Tanioka, and W. Zhao, "Toward Scintillator High-Gain Avalanche Rushing Photoconductor Active Matrix Flat Panel Imager (SHARP-AMFPI): Initial fabrication and characterization," Med. Phys., vol. 45, no. 2, pp. 794-802, February 2018.

[13] D. Panneerselvam, "Evaluation of organic perovskite photoconductors for x-ray imaging detectors Dhilippan Mamsapuram Panneerselvam A Thesis the Department of Electrical and Computer Engineering," Concordia University, 2017.

[14] L. Basiricò, A. Ciavatti, T. Cramer, P. Cosseddu, A. Bonfiglio, and B. Fraboni, "Direct X-ray photoconversion in flexible organic thin film devices operated below 1 v," Nat. Commun., vol. 7, 2016.

[15] F. Maddalena et al., "Inorganic, Organic, and Perovskite Halides with Nanotechnology for High-Light Yield X- and γ-ray Scintillators," Crystals, vol. 9, no. 2, p. 88, 2019.

[16] J. H. Heo, D. H. Shin, J. K. Park, D. H. Kim, S. J. Lee, and S. H. Im, "High-Performance Next-Generation Perovskite Nanocrystal Scintillator for Nondestructive X-Ray Imaging," Adv. Mater., vol. 30, no. 40, pp. 1-6, 2018.

[17] W. Pan et al., "Cs2AgBiBr6 single-crystal X-ray detectors with a low detection limit," Nat. Photonics, vol. 11, no. 11, pp. 726-732, 2017.

[18] Y. Li et al., "Scintillation Properties of Perovskite Single Crystals," J. Phys. Chem. C, vol. 123, p. acs.jpcc.9b05269, 2019.

[19] Y. Zhang et al., "Metal Halide Perovskite Nanosheet for X-ray High-Resolution Scintillation Imaging Screens," ACS Nano, 2019.

[20] M. Z. Kabir and S. Kasap, "Photoconductors for X-Ray Image Detectors," in Springer Handbook of Electronic and Photonic Materials, 2017, pp. 1125-1147.

[21] W. Wei et al., "Monolithic integration of hybrid perovskite single crystals with heterogenous substrate for highly sensitive X-ray imaging," Nat. Photonics, vol. 11, no. 5, pp. 315-321, 2017.

[22] S. Shrestha et al., "High-performance direct conversion X-ray detectors based on sintered hybrid lead triiodide perovskite wafers," Nat. Photonics, vol. 11, no. 7, pp. 436-440, 2017.

[23] S. Yakunin et al., "Detection of X-ray photons by solution-processed lead halide perovskites," Nat. Photonics, vol. 9, no. 7, pp. 444-449, 2015.

[24] S. Yakunin et al., "Detection of gamma photons using solution-grown single crystals of hybrid lead halide perovskites," Nat. Photonics, vol. 10, pp. 585-589, 2016.

[25] H. S. Gill et al., "Flexible perovskite based X-ray detectors for dose monitoring in medical imaging applications," Phys. Med., vol. 5, no. May 2016, pp. 20-23, 2018.

[26] F. Zhuge, P. Luo, and T. Zhai, "Lead-free perovskites for X-ray detecting," Sci. Bull., vol. 62, no. 22, pp. 1491-1493, 2017.

[27] N.-G. Park, "Halide perovskite photovoltaics: History, progress, and perspectives," MRS Bull., vol. 43, no. 7, pp. 527-533, 2018.

[28] H. Wei and J. Huang, "Halide lead perovskites for ionizing radiation detection," Nat. Commun., vol. 10, no. 1, pp. 1-12, 2019.

[29] D. N. Dirin, I. Cherniukh, S. Yakunin, Y. Shynkarenko, and M. V. Kovalenko, "Solution-Grown CsPbBr3 Perovskite Single Crystals for Photon Detection," Chem. Mater., vol. 28, no. 23, pp. 8470-8474, 2016.

[30] H. Wei et al., "Sensitive X-ray detectors made of methylammonium lead tribromide perovskite single crystals," Nat. Photonics, vol. 10, no. 5, pp. 333-339, 2016.

[31] Y. He et al., "High spectral resolution of gamma-rays at room temperature by perovskite CsPbBr3 single crystals," Nat. Commun., vol. 9, no. 1, p. 1609, 2018.

[32] Y. C. Kim et al., "Printable organometallic perovskite enables large-area, low-dose X-ray imaging," Nature, vol. 550, no. 7674, pp. 87-91, 2017.

[33] B. Náfrádi, G. Náfrádi, L. Forró, and E. Horváth, "Methylammonium Lead Iodide for Efficient X-ray Energy Conversion," J. Phys. Chem. C, vol. 119, no. 45, pp. 25204-25208, 2015.

[34] O. Nazarenko, S. Yakunin, V. Morad, I. Cherniukh, and M. V. Kovalenko, "Single crystals of caesium formamidinium lead halide perovskites: Solution growth and gamma dosimetry," NPG Asia Mater., vol. 9, no. 4, pp. e373-8, 2017.

[35] M. D. Birowosuto et al., "X-ray Scintillation in Lead Halide Perovskite X-ray Scintillation in Lead Halide Perovskite Crystals," Nat. Publ. Gr., no. November, pp. 87-100, 2016.

[36] V. B. Mykhaylyk, H. Kraus, and M. Saliba, "Bright and fast scintillation of organolead perovskite MAPbBr3 at low temperatures," Mater. Horizons, 2019.

[37] Q. Dong et al., "Electron-hole diffusion lengths >175 pm in solution-grown CH3NH3PbI3 single crystals," Science (80-)., vol. 347, no. 6225, pp. 967-970, February 2015.

[38] Y. Wang et al., "Hybrid Graphene-Perovskite Phototransistors with Ultrahigh Responsivity and Gain," Adv. Opt. Mater., vol. 3, no. 10, pp. 1389-1396, 2015.

[39] Y. Shao et al., "Stable Graphene-Two-Dimensional Multiphase Perovskite Heterostructure Phototransistors with High Gain," Nano Lett., vol. 17, no. 12, pp. 7330-7338, 201.

[40] P. H. Chang et al., "Ultrahigh responsivity and detectivity graphene-perovskite hybrid phototransistors by sequential vapor deposition," Sci. Rep., vol. 7, no. January, pp. 1-10, 2017.

[41] Y. Lee et al., "High-performance perovskite-graphene hybrid photodetector," Adv. Mater., vol. 27, no. 1, pp. 41-46, 2015.

[42] D. De Fazio et al., "High Responsivity, Large-Area Graphene/MoS2 Flexible Photodetectors," ACS Nano, vol. 10, no. 9, pp. 8252-8262, 2016.

[43] U. Sassi et al., "Graphene-based mid-infrared room-temperature pyroelectric bolometers with ultrahigh temperature coefficient of resistance," Nat. Commun., vol. 8, pp. 1-15, 2017.

[44] D. S. M. J. Berger, J. H. Hubbell, S. M. Seltzer, J. Chang, J. S. Coursey, R. Sukumar and K. O. Zucker, "XCOM: Photon Cross-section Database (Version 3.1), NIST Physical Measurement Laboratory," 2010. www.nist.gov/pml/xcom-photon-cross-sections-database.

[45] H. Wu, "X-ray Imaging: Mammography." radiologykey.com/x-ray-imaging-mammography/

[46] D. Shi et al., "Low trap-state density and long carrier diffusion in organolead trihalide perovskite single crystals," Science (80)., vol. 347, no. 6221, pp. 519-522, 2015.

[47] A. A. Zhumekenov et al., "Formamidinium Lead Halide Perovskite Crystals with Unprecedented Long Carrier Dynamics and Diffusion Length," 2016.

[48] E. Alarousu et al., "Ultralong Radiative States in Hybrid Perovskite Crystals: Compositions for Submillimeter Diffusion Lengths," J. Phys. Chem. Lett., vol. 8, no. 18, pp. 4386-4390, 2017.

[49] P. Zambon et al., "Spectral response characterization of CdTe sensors of different pixel size with the IBEX ASIC," Nucl. Instruments Methods Phys. Res. Sect. A Accel. Spectrometers, Detect. Assoc. Equip., vol. 892, no. February, pp. 106-113, 2018.

[50] O. Roberts, Solid-State Radiation Detectors: Technology and Applications, Devices, C. CRC Press, 2015.

[51] M. I. Saidaminov et al., "High-quality bulk hybrid perovskite single crystals within minutes by inverse temperature crystallization," Nat. Commun., vol. 6, no. May, pp. 1-6, 2015.

[52] J. T. Tisdale et al., "Methylammonium Lead Tribromide Single Crystal Detectors towards Robust Gamma-Ray Photon Sensing," Adv. Opt. Mater., vol. 8, no. 10, pp. 1-9, 2020.

[53] F. Liu et al., "The working principle of hybrid perovskite gamma-ray photon counter," Mater. Today, vol. 37, no. xx, pp. 27-34, 2020.

[54] S. Shrestha et al., "Role of the Metal-Semiconductor Interface in Halide Perovskite Devices for Radiation Photon Counting," ACS Appl. Mater. Interfaces, vol. 12, no. 40, pp. 45533-45540, 2020.

[55] Y. Liu et al., "Triple-Cation and Mixed-Halide Perovskite Single Crystal for High-Performance X-ray Imaging," Adv. Mater., vol. 33, no. 8, pp. 1-10, 2021.

I claim:

1. A direct conversion sensor comprising:
   a graphene;
   a perovskite provided directly on the graphene surface;
   a first electrode and a second electrode in electrical communication with the graphene; and
   an encapsulant that encapsulates the first electrode and the second electrode, thereby electrically isolating said first electrode and said second electrode from the perovskite,
   wherein the graphene is a continuous layer providing electrical communication between the first electrode and the second electrode; and
   the graphene provides the only electrical connection to the perovskite.

2. The direct conversion sensor of claim 1, wherein the direct conversion sensor is an energy integrating sensor.

3. The direct conversion sensor of claim 1, wherein a graphene field effect transistor comprises the graphene.

4. The direct conversion sensor of claim 1, wherein the perovskite is compositionally tuned to minimize and/or eliminate k-fluorescence from 20 to 140 keV.

5. The direct conversion sensor of claim 1, wherein the perovskite is a single crystal.

6. The direct conversion sensor of claim 3, wherein the graphene field effect transistor comprises a substrate; a back-gate; a gate dielectric, and said graphene, wherein the first electrode and the second electrode provide source-drain edge contacts.

7. The direct conversion sensor of claim 1, wherein said graphene is patterned.

8. The direct conversion sensor of claim 1, further comprising a protective layer provided over the perovskite.

9. The direct conversion sensor of claim 1, wherein a work function differential between the perovskite and graphene at the perovskite-graphene interface generates an internal field that moves electrons and/or holes.

10. The direct conversion sensor of claim 1, wherein said perovskite has a formula $ABX_3$, wherein A has no k-edge, B is a high-Z material, and X has a k-edge at an energy less than 60 keV.

11. The direct conversion sensor of claim 10, wherein X comprises a halide.

12. The direct conversion sensor of claim 10, wherein A comprises an organic cation, an inorganic cation, a methylammonium, a formamidinium, a cesium ion, a cadmium ion, or a rubidium ion, and/or combinations thereof.

13. The direct conversion sensor of claim 10, wherein B comprises lead or tin.

14. The direct conversion sensor of claim 1, wherein said perovskite comprises formamidinium lead tribromide ($FAPbBr_3$).

15. The direct conversion sensor of claim 1, wherein said perovskite comprises methylammonium lead triiodide ($MAPbI_3$).

16. The direct conversion sensor of claim 1, wherein the perovskite is 1 μm to 1 mm thick.

17. The direct conversion sensor of claim 1, wherein the perovskite has a thickness that varies less than 100 μm.

18. The direct conversion sensor of claim 1, wherein the direct conversion sensor provides a single pixel having dimensions of less than 500 μm×500 μm.

19. The direct conversion sensor of claim 1, further comprising a readout integrated circuit (ROIC).

20. A detector comprising an array of direct conversion sensors of claim 1.

21. The direct conversion sensor of claim 1, further comprising a substrate adjacent to the graphene.

* * * * *